United States Patent
Aklog et al.

(10) Patent No.: US 10,687,883 B2
(45) Date of Patent: Jun. 23, 2020

(54) CONTINUOUS FLOW BALLOON CATHETER SYSTEMS AND METHODS OF USE

(71) Applicant: PAVmed Inc., New York, NY (US)

(72) Inventors: Lishan Aklog, New York, NY (US); Brian J. deGuzman, Paradise Valley, AZ (US)

(73) Assignee: PAVmed Inc., New York, NY (US)

( * ) Notice: Subject to any disclaimer, the term of this patent is extended or adjusted under 35 U.S.C. 154(b) by 0 days.

(21) Appl. No.: 16/254,717

(22) Filed: Jan. 23, 2019

(65) Prior Publication Data
US 2019/0151007 A1    May 23, 2019

Related U.S. Application Data

(63) Continuation of application No. 15/067,148, filed on Mar. 10, 2016, now Pat. No. 10,213,245.
(Continued)

(51) Int. Cl.
*A61B 18/00* (2006.01)
*A61B 18/04* (2006.01)
(Continued)

(52) U.S. Cl.
CPC ...... *A61B 18/04* (2013.01); *A61B 2018/0022* (2013.01); *A61B 2018/00023* (2013.01);
(Continued)

(58) Field of Classification Search
CPC .......... A61B 18/04; A61B 2018/00255; A61B 2018/0022; A61B 2018/00577;
(Continued)

(56) References Cited

U.S. PATENT DOCUMENTS

| 5,190,539 A | 3/1993 | Fletcher et al. |
| 5,295,960 A | 3/1994 | Klihmad et al. |

(Continued)

FOREIGN PATENT DOCUMENTS

| EP | 0182689 | 12/1991 |
| WO | 2016145214 A1 | 9/2016 |

OTHER PUBLICATIONS

International Search Report and Written Opinion issued in International Application No. PCT/US2016/021804 dated Jul. 21, 2016.
(Continued)

*Primary Examiner* — Jaymi E Della
*Assistant Examiner* — Rachel A. Vierra
(74) *Attorney, Agent, or Firm* — Greenberg Traurig, LLP; Chinh H. Pham; Todd C. Basile

(57) ABSTRACT

Systems and methods for continuous infusion of a fluid, which may be heated, into a balloon catheter. A system for balloon inflation, the system comprising a catheter having an inflow lumen and an outflow lumen, a balloon positioned at a distal end of the catheter, the balloon being in fluid communication with the inflow and the outflow lumen, and an infusion device in fluid communication with the balloon through the inflow and outflow lumens, the infusion device configured for continuously circulating a fluid into and out of the balloon to maintain the balloon at a constant pressure and volume by matching a flow of the fluid into the balloon via the inflow lumen with a flow of the fluid out of the balloon via the outflow lumen in order to keep the balloon volume and pressure constant during an entire infusion.

14 Claims, 74 Drawing Sheets

Related U.S. Application Data

(60) Provisional application No. 62/131,217, filed on Mar. 10, 2015, provisional application No. 62/131,214, filed on Mar. 10, 2015.

(51) Int. Cl.
*A61M 25/10* (2013.01)
*A61M 1/00* (2006.01)

(52) U.S. Cl.
CPC .............. *A61B 2018/00255* (2013.01); *A61B 2018/00577* (2013.01); *A61B 2018/00714* (2013.01); *A61B 2018/00821* (2013.01); *A61B 2018/046* (2013.01); *A61M 1/00* (2013.01); *A61M 25/10181* (2013.11); *A61M 25/10182* (2013.11); *A61M 25/10184* (2013.11)

(58) Field of Classification Search
CPC ...... A61M 25/10181; A61M 25/10182; A61M 25/1018; A61M 25/10; A61M 2025/1072; A61M 1/00
See application file for complete search history.

(56) References Cited

U.S. PATENT DOCUMENTS

| | | |
|---|---|---|
| 5,342,301 A | 8/1994 | Saab |
| 5,344,402 A | 9/1994 | Crocker |
| 5,415,634 A | 5/1995 | Glynn et al. |
| 5,417,689 A | 5/1995 | Fine |
| 5,529,463 A | 6/1996 | Layer et al. |
| 5,954,665 A | 9/1999 | Ben-Haim |
| 6,123,712 A | 9/2000 | Di Caprio et al. |
| 6,159,227 A | 12/2000 | Di Caprio et al. |
| 6,190,355 B1 | 2/2001 | Hastings |
| 6,428,563 B1 | 8/2002 | Keller |
| 6,440,158 B1 | 8/2002 | Saab |
| 6,605,056 B2 | 8/2003 | Eidenschink et al. |
| 6,719,720 B1 | 4/2004 | Voelker |
| 6,776,771 B2 | 8/2004 | Van Moortegem |
| 7,147,619 B2 | 12/2006 | Lim et al. |
| 7,303,572 B2 | 12/2007 | Melsheimer et al. |
| 7,322,957 B2 | 1/2008 | Kletschka et al. |
| 7,708,753 B2 | 5/2010 | Hardet et al. |
| 7,935,077 B2* | 5/2011 | Thor .................. A61M 5/14232 604/67 |
| 8,652,190 B2 | 2/2014 | Stull |
| 9,757,535 B2 | 9/2017 | Rajagopalan et al. |
| 9,844,641 B2 | 12/2017 | Rajagopalan et al. |
| 10,213,245 B2 | 2/2019 | Aklog et al. |
| 10,232,143 B2 | 3/2019 | Rajagopalan et al. |
| 10,299,857 B2 | 5/2019 | Rajagopalan et al. |
| 10,349,998 B2 | 7/2019 | Levin et al. |
| 2003/0208156 A1 | 11/2003 | Pham et al. |
| 2004/0148004 A1 | 7/2004 | Wallsten |
| 2008/0156476 A1 | 7/2008 | Smission et al. |
| 2009/0054883 A1 | 2/2009 | Stolen et al. |
| 2009/0182317 A1 | 7/2009 | Bencini |
| 2010/0094270 A1 | 4/2010 | Sharma |
| 2012/0041412 A1 | 2/2012 | Roth et al. |
| 2012/0226230 A1 | 9/2012 | Gerrans et al. |
| 2013/0150881 A1 | 6/2013 | Wang et al. |
| 2013/0184791 A1 | 7/2013 | Wallsten |
| 2013/0345670 A1 | 12/2013 | Rajagopalan et al. |
| 2014/0180077 A1 | 6/2014 | Kluennekens et al. |
| 2014/0249563 A1 | 9/2014 | Malhi |
| 2014/0257097 A1* | 9/2014 | Bonnette .............. A61M 5/007 600/432 |
| 2014/0276585 A1 | 9/2014 | Gianotti |
| 2014/0277346 A1 | 9/2014 | Kanjickal et al. |
| 2014/0371736 A1 | 12/2014 | Levin et al. |
| 2015/0045825 A1 | 2/2015 | Caplan et al. |
| 2015/0081006 A1 | 3/2015 | Chuter et al. |
| 2015/0141987 A1 | 5/2015 | Caplan et al. |
| 2015/0148738 A1 | 5/2015 | Caplan et al. |
| 2015/0148742 A1* | 5/2015 | Satake .................. A61B 18/04 604/97.02 |
| 2016/0008050 A1 | 1/2016 | Rajagopalan et al. |
| 2016/0262823 A1 | 9/2016 | Aklog et al. |
| 2016/0354144 A1 | 12/2016 | Caplan et al. |
| 2017/0007324 A1 | 1/2017 | Kadamus et al. |
| 2017/0333122 A1 | 11/2017 | Rajagopalan et al. |
| 2018/0193078 A1 | 7/2018 | Rajagopalan et al. |
| 2018/0193590 A1 | 7/2018 | Rajagopalan et al. |
| 2018/0199983 A1 | 7/2018 | Aklog et al. |
| 2018/0199984 A1 | 7/2018 | Aklog et al. |
| 2018/0221622 A1 | 8/2018 | Rajagopalan et al. |
| 2020/0001047 A1 | 1/2020 | Rajagopalan et al. |
| 2020/0060758 A1 | 2/2020 | Rajagopalan et al. |
| 2020/0060942 A1 | 2/2020 | Rajagopalan et al. |

OTHER PUBLICATIONS

Extended European Search Report in European Application No. 16762527.6 dated Oct. 1, 2018.

\* cited by examiner

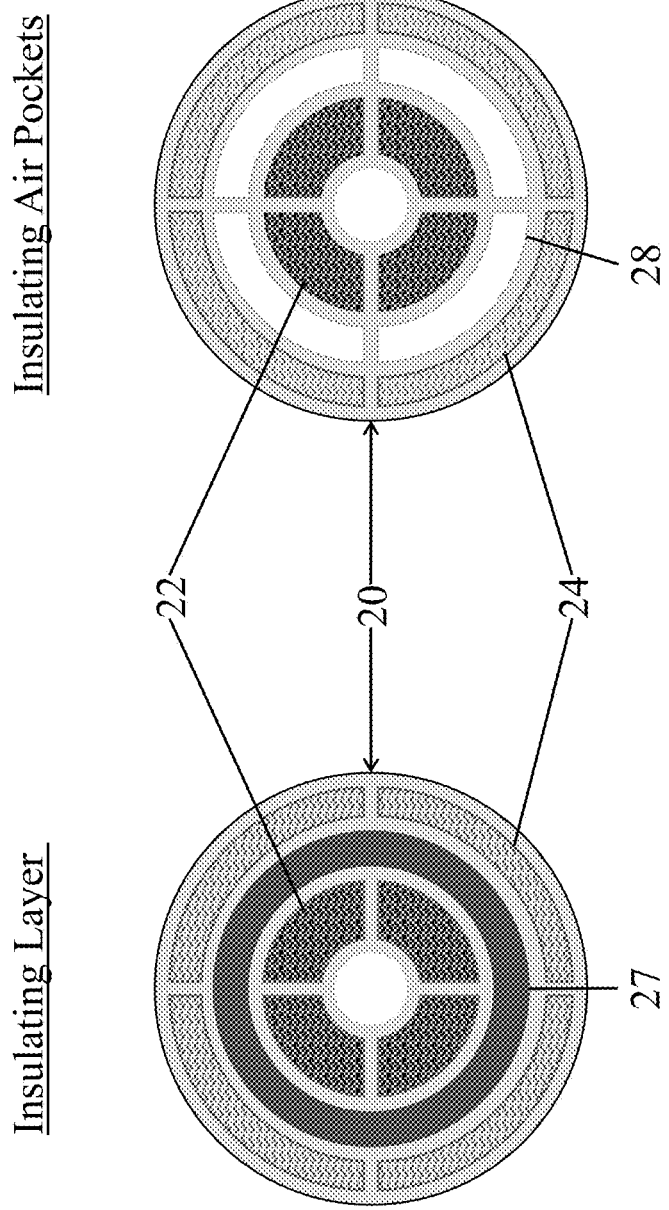

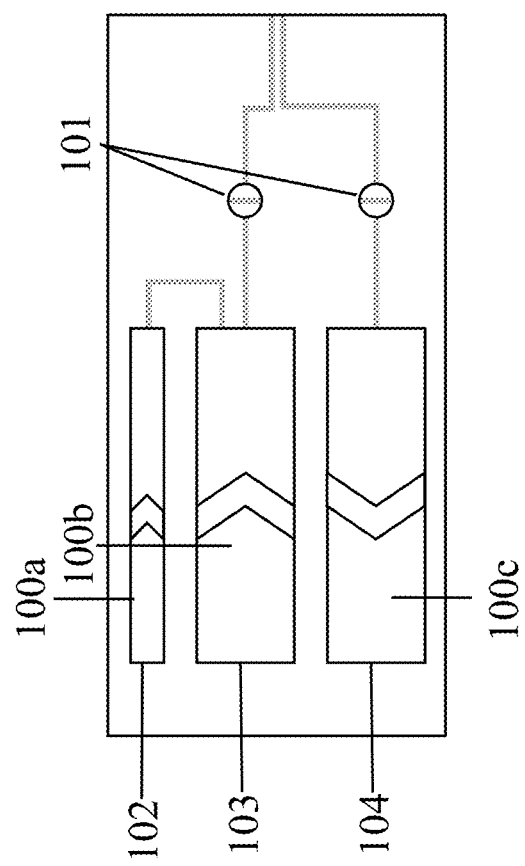

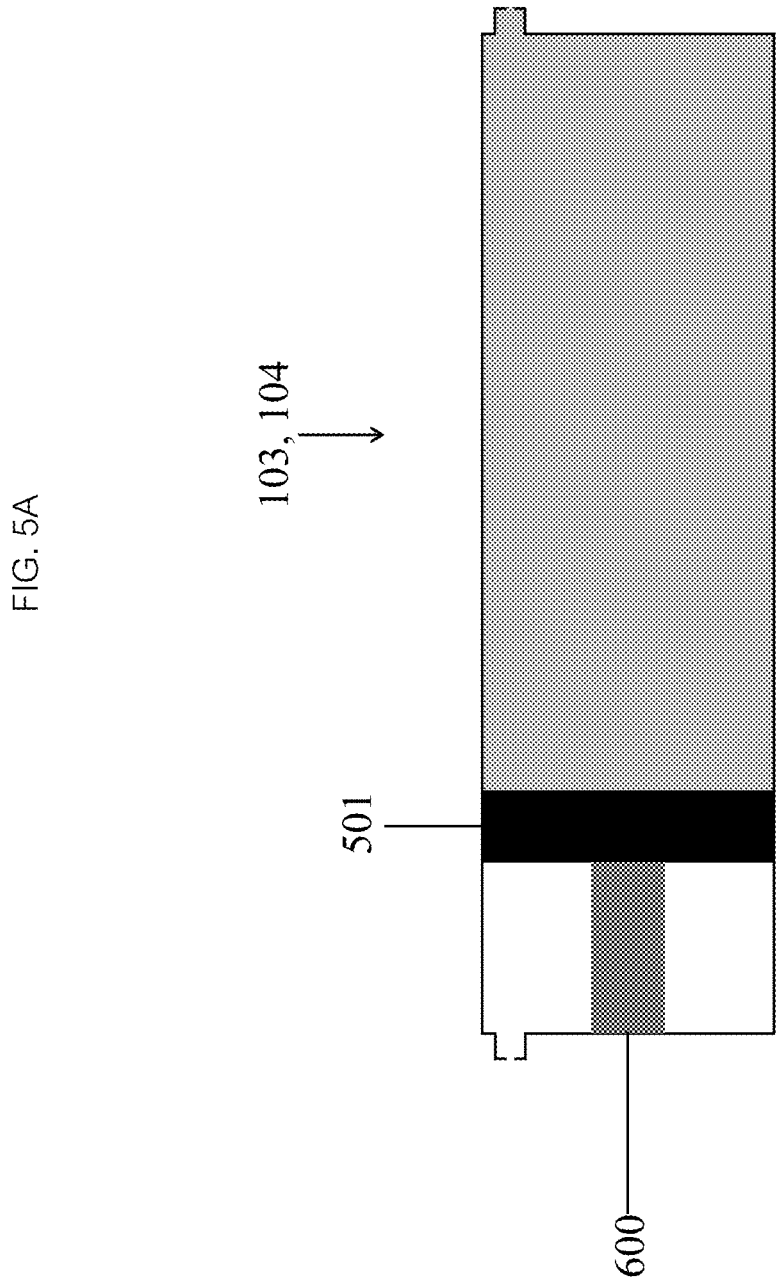

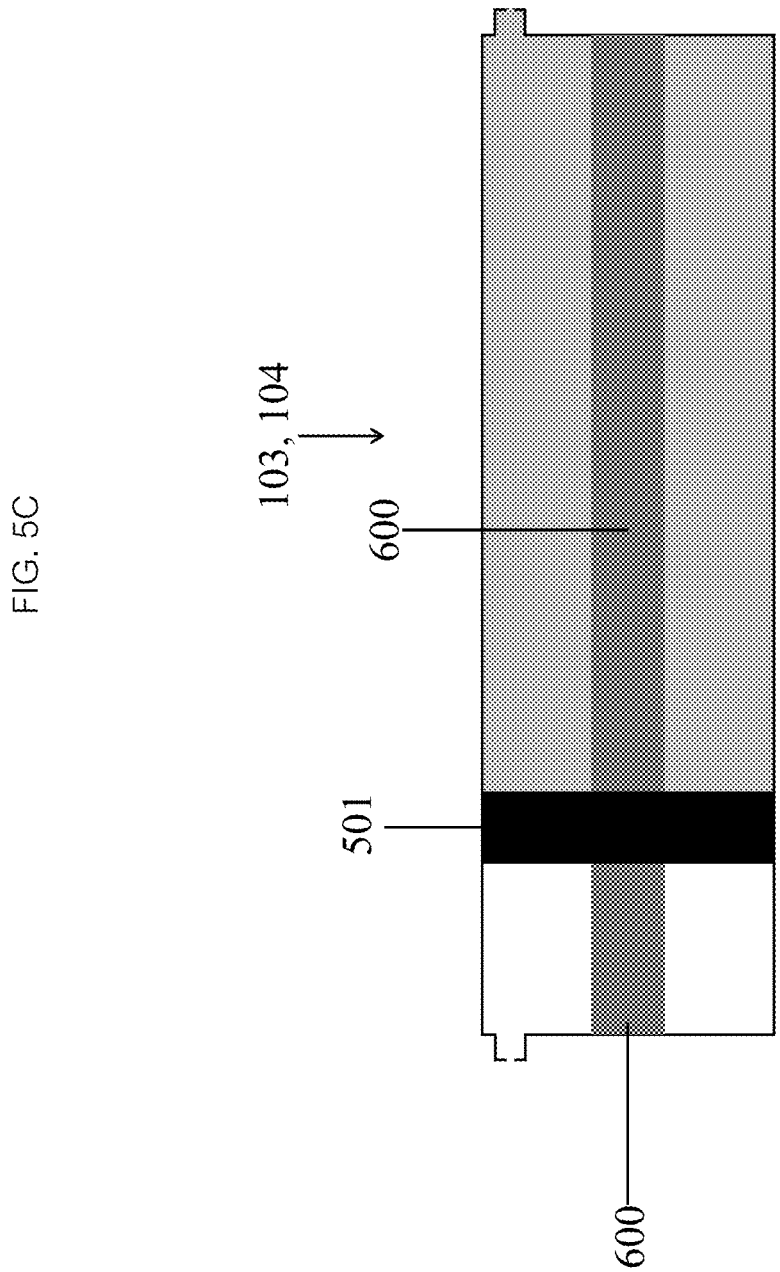

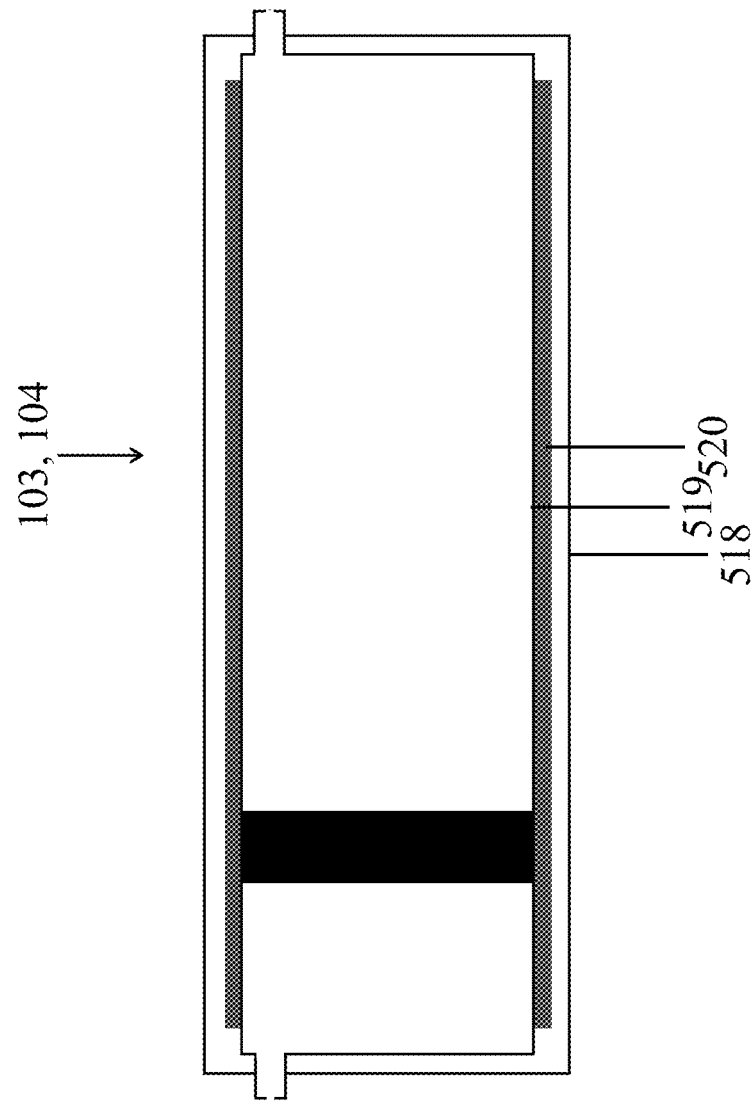

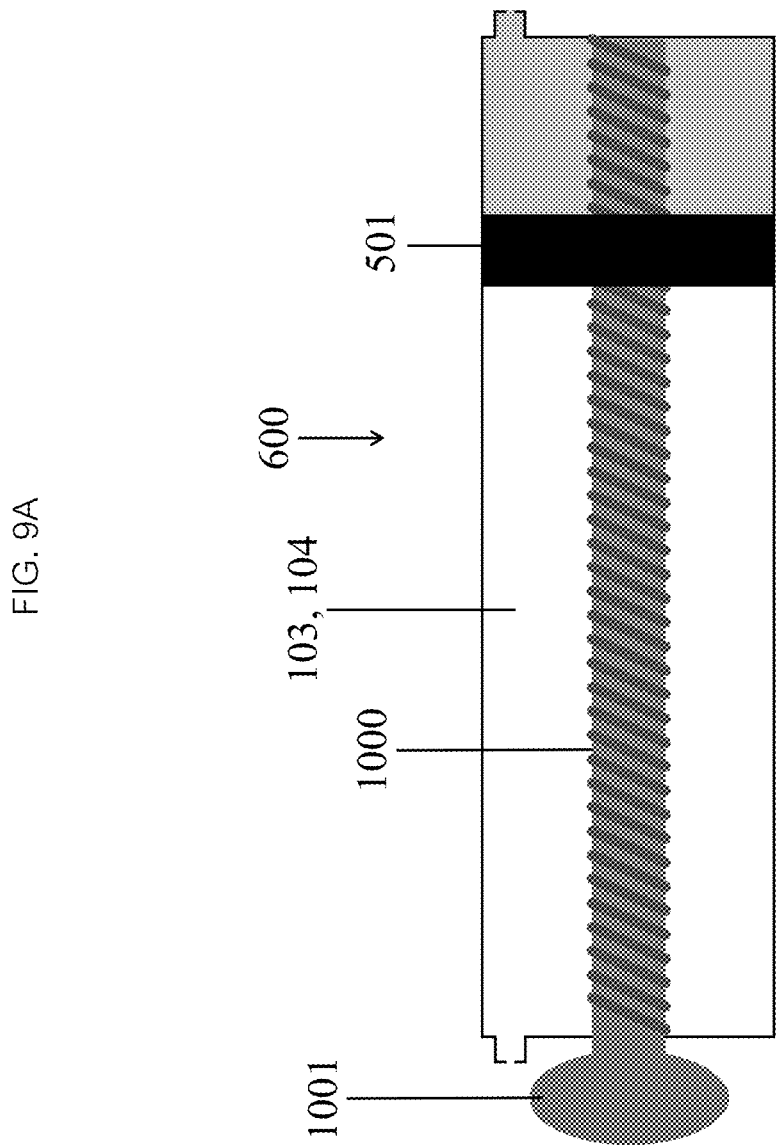

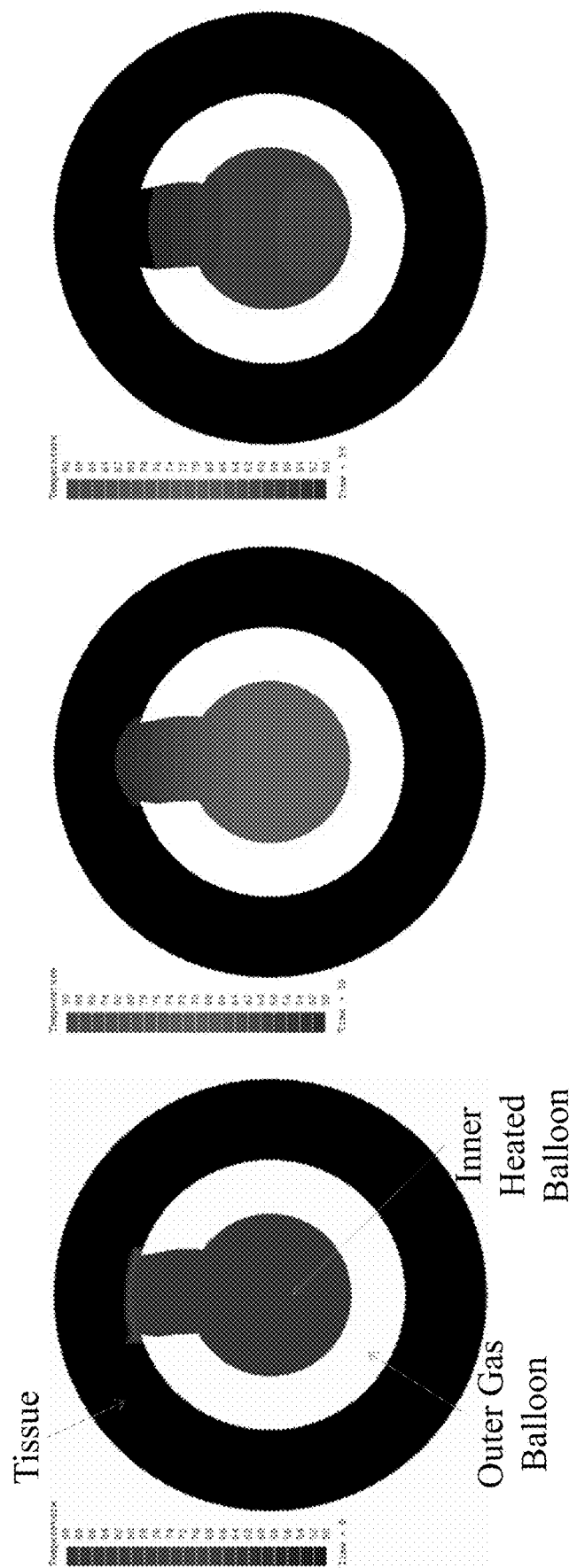
FIG. 20A1  FIG. 20A2  FIG. 20A3

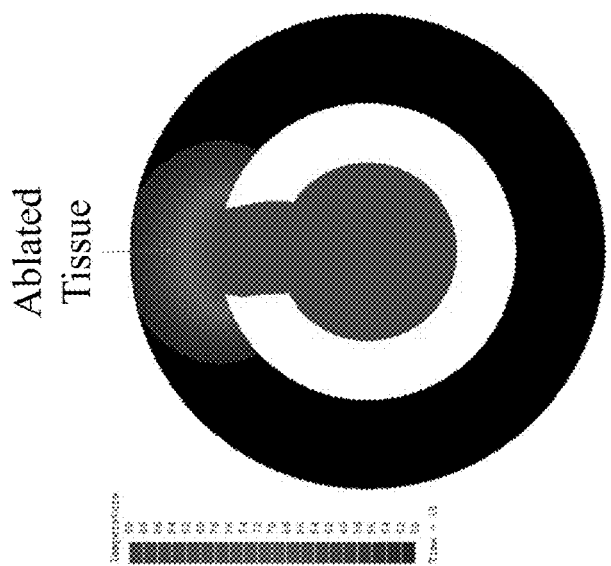
FIG. 20B3
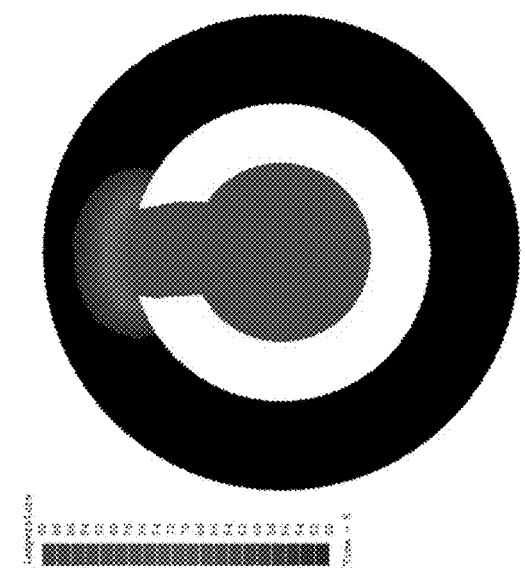
FIG. 20B2
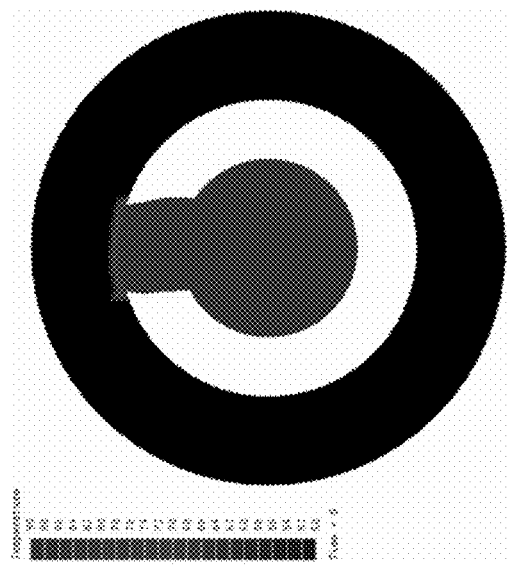
FIG. 20B1

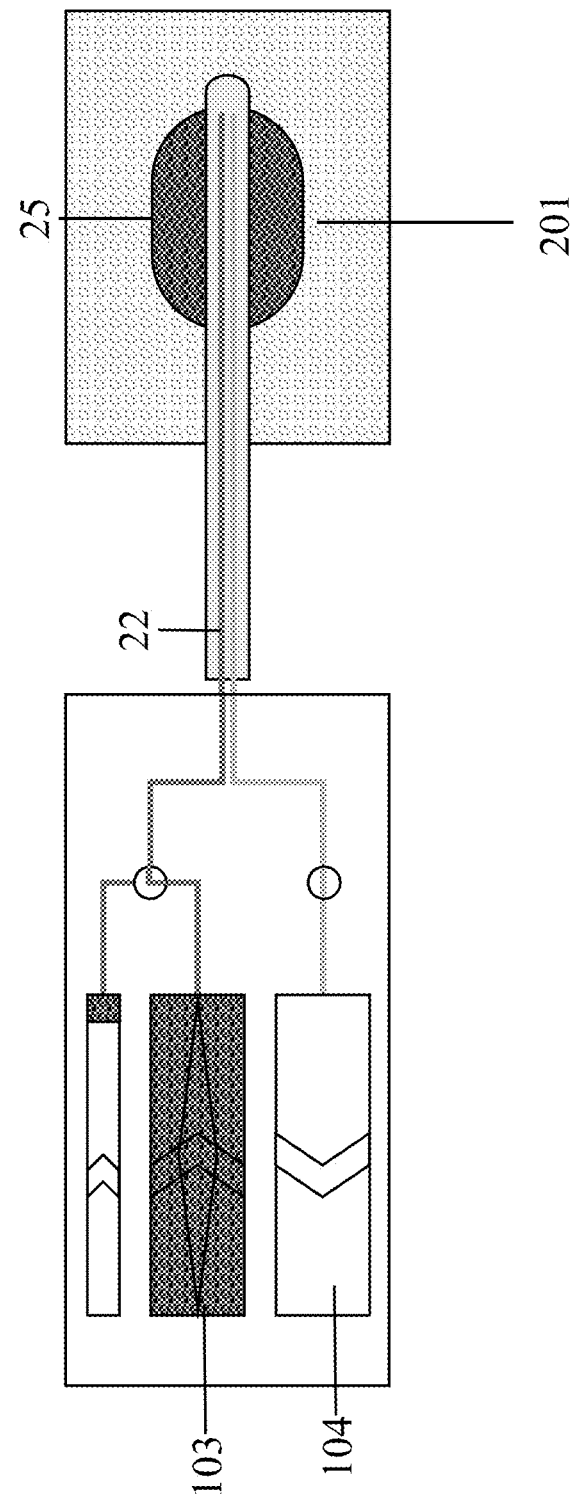

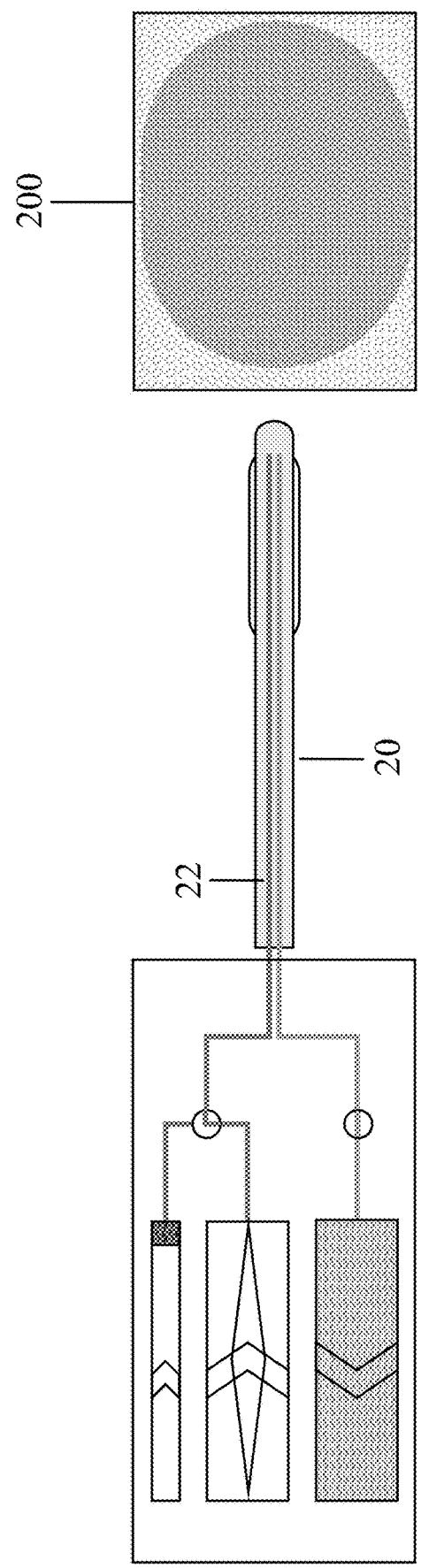

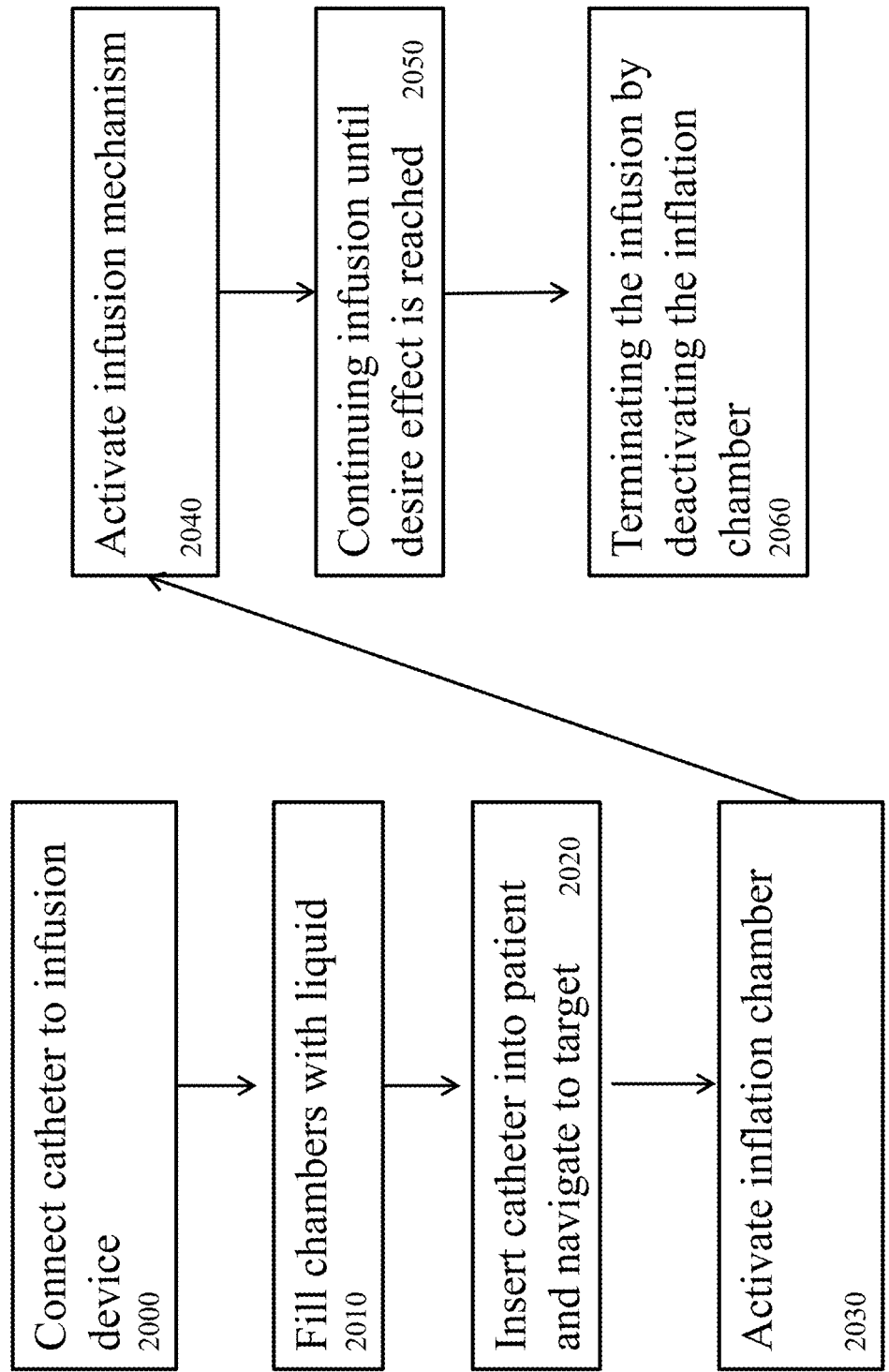

CONTINUOUS FLOW BALLOON CATHETER SYSTEMS AND METHODS OF USE

RELATED APPLICATIONS

This application is a continuation of U.S. application Ser. No. 15/067,148, filed Mar. 10, 2016, which claims the benefit of and priority to U.S. Provisional Application No. 62/131,214, filed on Mar. 10, 2015, and U.S. Provisional Application No. 62/131,217, filed on Mar. 10, 2015. All of these applications are incorporated herein by reference in their entireties.

FIELD

The disclosure relates generally to systems and methods for infusion or ablation target tissues with a balloon catheter.

BACKGROUND

Balloon catheters are used for a wide variety of medical applications including angioplasty, stent deployment, embolectomy and balloon occlusion of blood vessels. A standard balloon catheter has a catheter with at least one lumen, a compliant or non-compliant balloon positioned coaxially around and bonded to the catheter at or near its distal tip. At least one of the catheter lumens, the inflation lumen, has at least one orifice positioned within the balloon lumen such that this inflation lumen is in fluid communication with the inside of the balloon. The balloon is deployed by attaching a syringe or other infusion device to the proximal end of the catheter, so that it is in fluid communication with the catheter's inflation lumen, and injecting a volume of fluid (liquid or gas) through the inflation lumen into the balloon, inflating it to a given volume or pressure. The balloon is deflated by withdrawing the fluid from the balloon lumen through the catheter's inflation lumen back into the reservoir of the syringe or other infusion device. The catheter may have additional lumens such as a guidewire lumen to facilitate maneuvering of the catheter within the body, infusion lumens to infuse fluid out the distal tip of the catheter into the patient and monitoring lumens to monitor pressure, temperature or other parameters.

There are applications where it is desirable for the fluid which inflates the balloon to flow continuously into and out of the balloon while maintaining the balloon inflated at the desired volume and pressure. One such application would be thermal ablation balloon catheters which ablate tissue using hyper or hypothermia. Balloon catheters are useful in these applications because they can be designed to conform to the tissue to be ablated once positioned in the appropriate location. Another such application would be a drug delivery balloon catheter where the balloon serves as a reservoir for a drug to be delivered through its permeable wall.

Tissue ablation is performed throughout the body. It is frequently used to destroy abnormal tissue such as malignant tumors (e.g. liver, lung) or other non-malignant tissue (e.g. endometrial, prostatic). It is also frequently used to target structurally normal tissues for a specific therapeutic effect such as cardiac tissue ablation to treat arrhythmias and more recently renal nerve ablation ("renal denervation") to treat refractory hypertension.

Tissue ablation is most commonly performed by applying energy to the target tissue to cause irreversible cellular injury. Common energy sources for tissue ablation include radiofrequency, microwave, laser, ultrasound and cryo. Each source has its own specific characteristics, biophysical mechanism, advantages and disadvantages. All of these modalities, with the exception of cryo, ultimately act by increasing the tissue temperature to cytotoxic levels for a given period of time. Cellular injury is generally reversible below 46 C. Although there is some variability in thermal sensitivity among different tissues and cell types, irreversible cellular injury generally occurs after 60 minutes at 46 C and less than 5 minutes at 50 C.

Most clinical applications of thermal ablation have involved either large volumes of tissue (e.g. tumor ablation) or at least relatively thick tissues (e.g. cardiac ablation) where complete ablation of the target tissue is necessary for a successful therapeutic effect. Even a small volume of residual viable tissue can lead to clinical failure in the form of recurrent tumor growth, metastases from residual tumor or recurrent arrhythmias from residual pathways. For the ablation to be successful, the cells farthest from the energy source must reach the target cytotoxic temperature. The larger the distance from the energy probe to the border of the target tissue the more challenging the ablation, the more energy needs to be delivered and the higher the temperature near the probe needs to be. For example, RF ablation depends on electrical conductivity to generate heat but creating too much heat near the probe can generate charring which increases impedance and decreases the effective range of the ablation. A wide variety of technologies and techniques have been developed to accommodate the challenges of ablating across a large distances using RF (e.g. multi-electrode probes, cooling, irrigation and complex power algorithms). As a result, these tissue ablation modalities typically require a complex, external console to assure the precise amount of energy is delivered to the tissue to achieve the desired therapeutic effect. Simpler devices which use a "shotgun" approach may be ineffective or downright harmful.

The major limitation of standard balloon catheters in hyperthermic ablation applications is that the surrounding tissue serves as a powerful thermal sink. The temperature in the balloon may equilibrate with the surrounding tissue within a short period of time, shorter than the time necessary to perform the ablation, typically several minutes. For hypothermic (cryo) ablation the fluid temperature can be made so cold using liquid gases (e.g. argon, nitrogen) that the time required for the temperature to equilibrate is longer than the time it takes to ablate the tissue. For hyperthermic ablation, however, the options are more limited since the boiling temperature of most biocompatible fluids are only modestly above the temperature necessary to successfully ablate most tissues. Most tissue ablation is therefore performed using a fixed probe which is inserted into the tissue and attached to an external energy source (e.g. radiofrequency, microwave). The source continuously provides energy to the tissue as the heat dissipates into the surrounding tissue.

SUMMARY

In some embodiments in accordance with the present disclosure, a system for balloon inflation, the system comprising a catheter having an inflow lumen and an outflow lumen, a balloon positioned at a distal end of the catheter, the balloon being in fluid communication with the inflow and the outflow lumen, and an infusion device in fluid communication with the balloon through the inflow and outflow lumens. In some embodiments, the infusion device may be configured for continuously circulating a fluid into and out of the balloon to maintain the balloon at a constant pressure and volume by matching a flow of the fluid into the balloon via the inflow lumen with a flow of the fluid out of the balloon via the outflow lumen in order to keep the balloon volume and pressure constant during an entire infusion. In some embodiments, the infusion device may further comprise a heating mechanism to heat the fluid to generate a heated fluid in order to maintain a constant temperature in the balloon via the heated fluid. In some embodiments the balloon may be is divided by a plurality of septae into multiple compartments, the multiple compartments comprising a mixture of heated compartments and insulating compartments, the heated compartments configured to contain the heated fluid and the insulating compartments configured to contain an insulating fluid. In some embodiments a surface of the balloon overlying one or more of the heated compartments allows heat from the heated fluid to transfer to and ablate a target tissue adjacent to the surface of the one or more heated compartments, and a surface overlying one or more of the insulating compartments prevents heat from transferring to a tissue adjacent to the one or more insulating compartments, thereby protecting the tissue adjacent to the one or more insulating compartments from ablation.

In some embodiments, the infusion device may further comprise a reservoir being configured to hold the fluid, an inflow chamber being in fluid communication with the balloon via the inflow lumen, and an outflow chamber being in fluid communication with the balloon via the outflow lumen. In some embodiments the reservoir may further comprise a piston disposed therein and may be in fluid communication with the balloon such that the reservoir may be configured to inflate the balloon via the inflow lumen. In some embodiments, the reservoir may further comprise a heating mechanism configured to heat the fluid to generate a heated fluid in order to maintain a constant temperature in the balloon via the heated fluid. In some embodiments, the catheter may further comprise a lumen containing a monitoring device for monitoring a location and orientation of the catheter in relation to a target tissue.

In other embodiments in accordance with the present disclosure, a system for ablation of a target tissue comprising a balloon having one or more heated compartments and one or more insulating compartments, a heated fluid contained in the one or more heated compartments, and an insulation fluid contained in the one or more insulating compartments, wherein a distribution of the one or more heated compartments among the one or more insulating compartments is selected to provide a desired ablation pattern at a target tissue. In some embodiments, the one or more heated compartments may comprise an inner balloon, and the one or more insulating compartments may comprise an outer balloon, the inner balloon being configured to contain a heated fluid and to make a point of contact with a portion of the outer balloon in order to deliver heat from the heated fluid to the target tissue adjacent to the point of contact, the outer balloon being configured to contain an insulating fluid and to protect a tissue next to the target tissue from ablation. In some embodiments, the inner balloon may be configured to make more than one point of contact with the outer balloon, the more than points of contact defining an ablation pattern for the target tissue. In some embodiments, the insulating fluid may be a gas.

In another embodiment in accordance with the present invention, a method using a balloon catheter comprising first positioning a catheter at a site of a target tissue for a first process, the catheter comprising a balloon, then inflating the balloon to a first volume and pressure with a fluid, and then continuously circulating the fluid in and out of the balloon at a flow and a rate maintaining the first volume and pressure during the first process. In some embodiments the method may further comprise heating the fluid to generate a heated fluid, and ablating the target tissue with heat from the heated fluid. In some embodiments, in the step of positioning, the balloon may be configured to ablate the target tissue in a desired pattern via the heat from the heated fluid. In some embodiments, the method further comprises monitoring a location and orientation of the balloon relative to the target tissue. In some embodiments, the method further comprises terminating the first process by reversing the flow of the fluid. In some embodiments the catheter need not be repositioned, but in some embodiments the method further comprises repositioning the catheter to a different target site for a second process, and inflating the balloon to a second volume and pressure. In some embodiments, in the step of positioning, the balloon catheter may further comprise an infusion device in fluid communication with the balloon catheter. In some embodiments, after the positioning step, the method further comprises attaching an infusion device to the catheter, the infusion device configured to be in fluid communication with the catheter.

BRIEF DESCRIPTION OF THE DRAWINGS

FIG. 2B is a crop sectional view of a balloon catheter illustrating the various layers and lumens within the balloon catheter.

FIGS. 3A-C illustrate various configurations of an infusion device in accordance with an embodiment of the present disclosure.

FIGS. 5A-E illustrate various drive mechanisms placement for activating an embodiment of an infusion mechanism in accordance with the present disclosure.

FIGS. 5F and 5G illustrate various configurations/designs for an external heating element for heating fluid in the infusion device in accordance with the present disclosure.

FIGS. 6A-C, 7, 8, and 9A-9B illustrate various manual drive mechanisms for activating embodiments of the infusion mechanism in accordance with the present disclosure.

FIGS. 20A1-20A3, 20B1-B3 and 20C illustrate thermal FEA analysis results in connection with thermal ablation carried out in accordance with various embodiments of the present disclosure.

FIGS. 21I-S illustrate a method of operating an embodiment of an ablation balloon catheter system in accordance with of the present disclosure.

FIG. 22 depicts a flow chart of a method in accordance with the present disclosure of inflating a balloon catheter with an infusion device.

DETAILED DESCRIPTION

Figure 1:
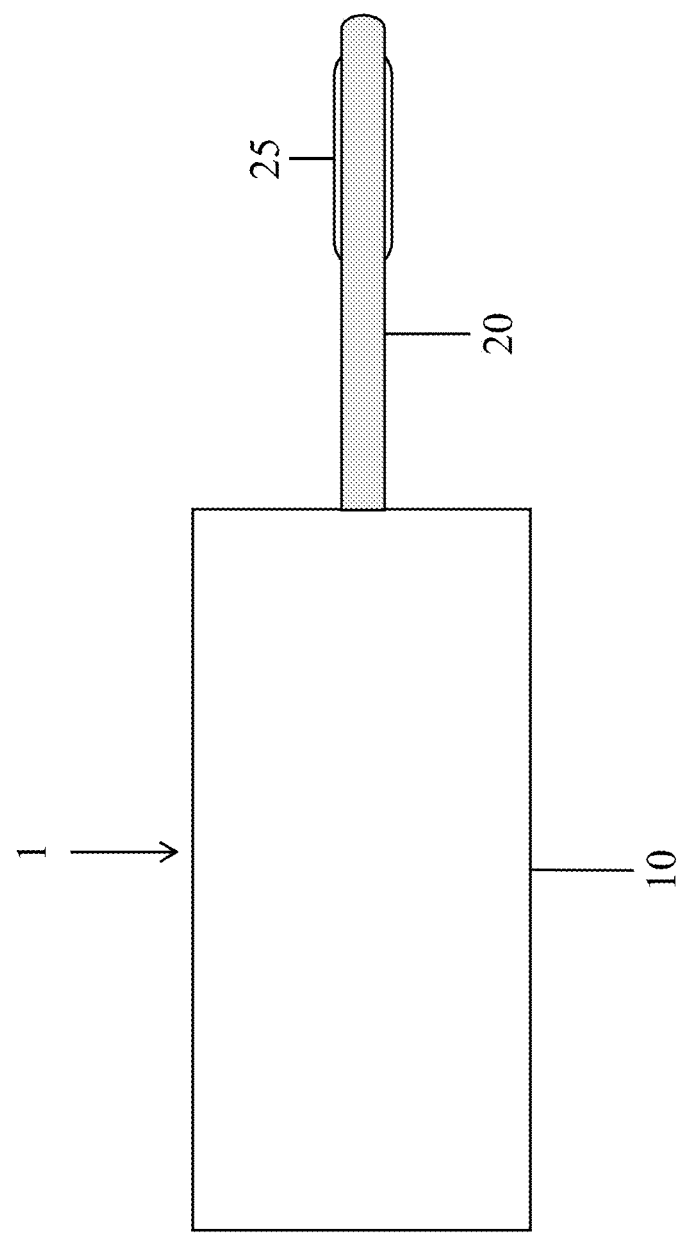
FIG. 1 illustrates a continuous flow balloon catheter system in accordance with an embodiment of the present invention.

There are applications where it is desirable for the fluid which inflates the balloon to flow continuously into and out of the balloon while maintaining the balloon inflated at the desired volume and pressure to assure continuous tissue contact. One such application would be thermal ablation balloon catheters which ablate tissue using hyper or hypothermia. In such applications the surrounding tissues serve as a heat sink which rapidly dissipates thermal energy from the balloon. A possible solution to the limitation of balloon catheters equilibrating with their surrounding tissues is to circulate a hot or cold fluid into and out of a balloon while maintaining the balloon at an inflation which is critical to assure tissue contact and thermal transfer into a target tissue. Maintaining such an equilibrium requires continuous flow with precise matching of flow into and out of the balloon. This is not possible with existing syringe-like disposable technologies since it requires continuous flow. Therefore, in accordance with the present disclosure, an embodiment of a system 1 with a continuous flow of a fluid into and out of a balloon catheter 20 may include at least two devices (see FIG. 1), the balloon catheter comprising a catheter 20 and a balloon 25, and an infusion device 10. The infusion device 10 may continuously drive or recirculate a fluid into and out of a reservoir, through the catheter 20, into and out of the balloon 25 while maintaining the balloon 25 inflated to a specified volume and pressure. In some embodiments, the fluid may be replenished or replaced for each given cycle. Alternatively, in some embodiments the fluid is recirculated or recycled. In some embodiments, the infusion device 10 may first heat the fluid (or liquid) to a target temperature, then continuously drive or recirculate the heated fluid from the reservoir, through the catheter 20, into and out of the balloon 25, and back into the reservoir while also maintaining the balloon 25 inflated to a specified volume and pressure.

Figure 2A:
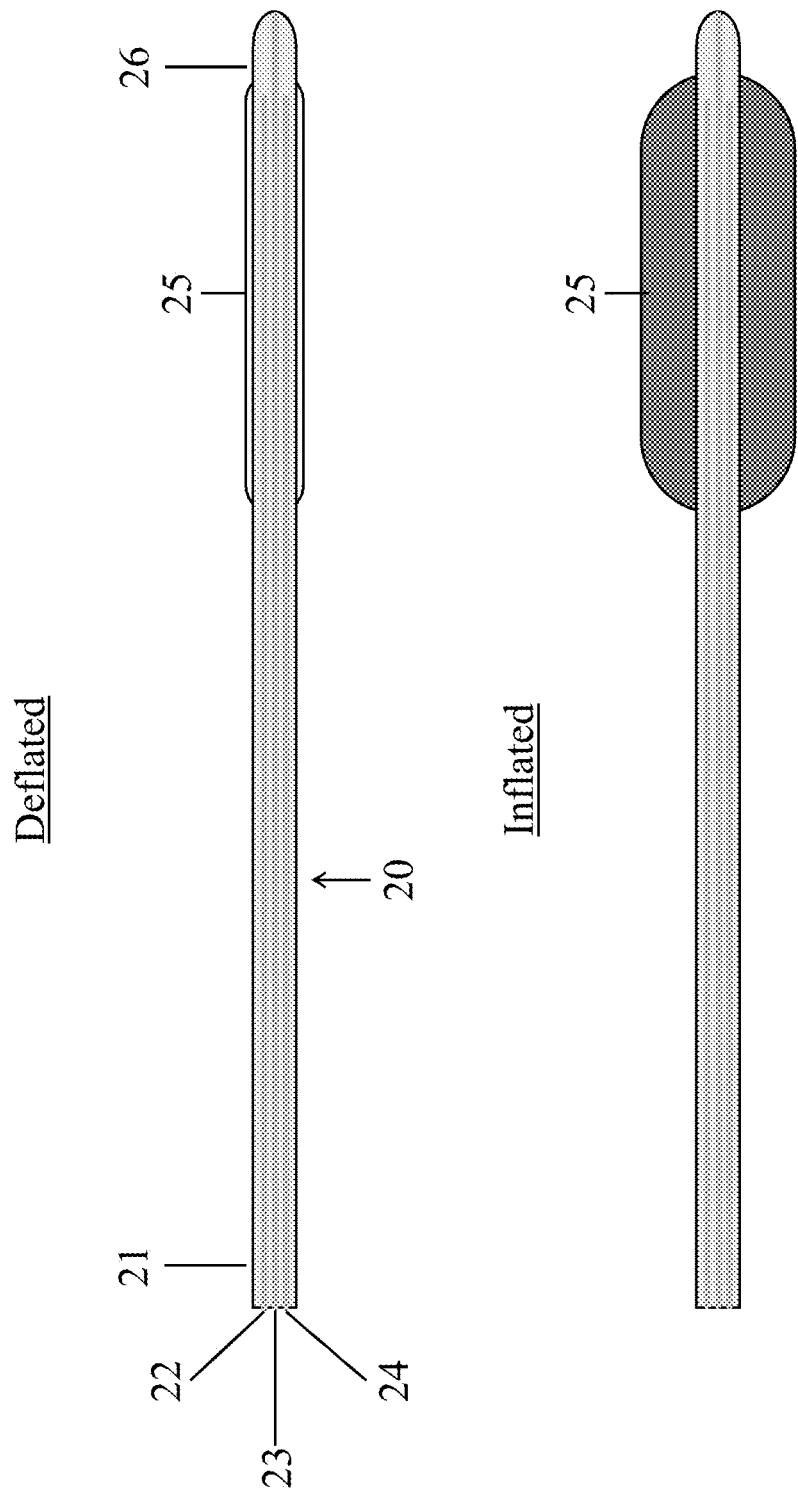
FIG. 2A illustrates a balloon catheter in accordance with an embodiment of the present disclosure.

The balloon catheter 20 (FIG. 2A) is an elongated tube having a proximal 21 and distal end 26, with a balloon 25 mounted at or near its distal end 26. The balloon 25 may be constructed of any compliant, semi-compliant or non-compliant material, typically a plastic such as polyurethane, nylon, polyethylene, PET or PEBAX. The catheter 20 may be made of similar materials and comprises at least two or more flow lumens 22-24, each in fluid communication with the balloon 25 through one or more distal orifices. When the system 1 is active, one or more inflow lumens 22 carries fluid into the balloon 25 and one or more outflow lumens 24 carries fluid out of the balloon 25. The system 1 can be designed so that flow of the fluid can be reversed with each flow lumen 22, 24 serving as either inflow 22 or outflow 24 depending on the direction of flow. In some embodiments, when the flow is reversed, the inflow lumen 22 will become the outflow lumen, and the outflow lumen 24 will become the inflow lumen. In some embodiments, the catheter 20 may contain additional lumens as desired for guidewires, infusion, monitoring, and other functionalities that may be directed via the additional lumens.

Figure 2C:
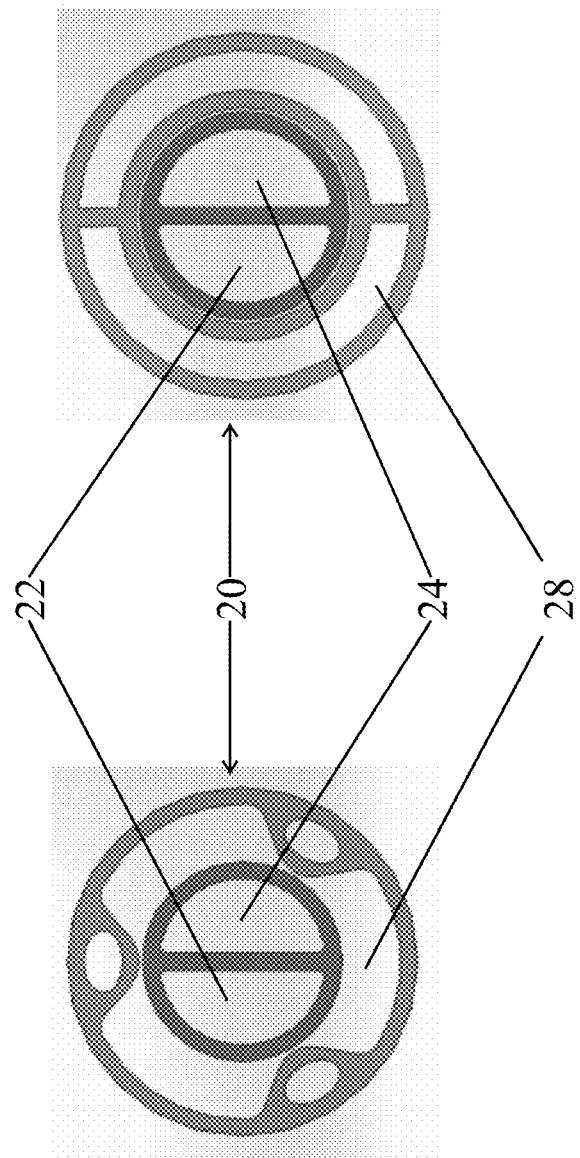
FIG. 2C and FIG. 2D are crop sectional views of a balloon catheter illustrating thermal insulation of flow lumens.
Figure 2D:
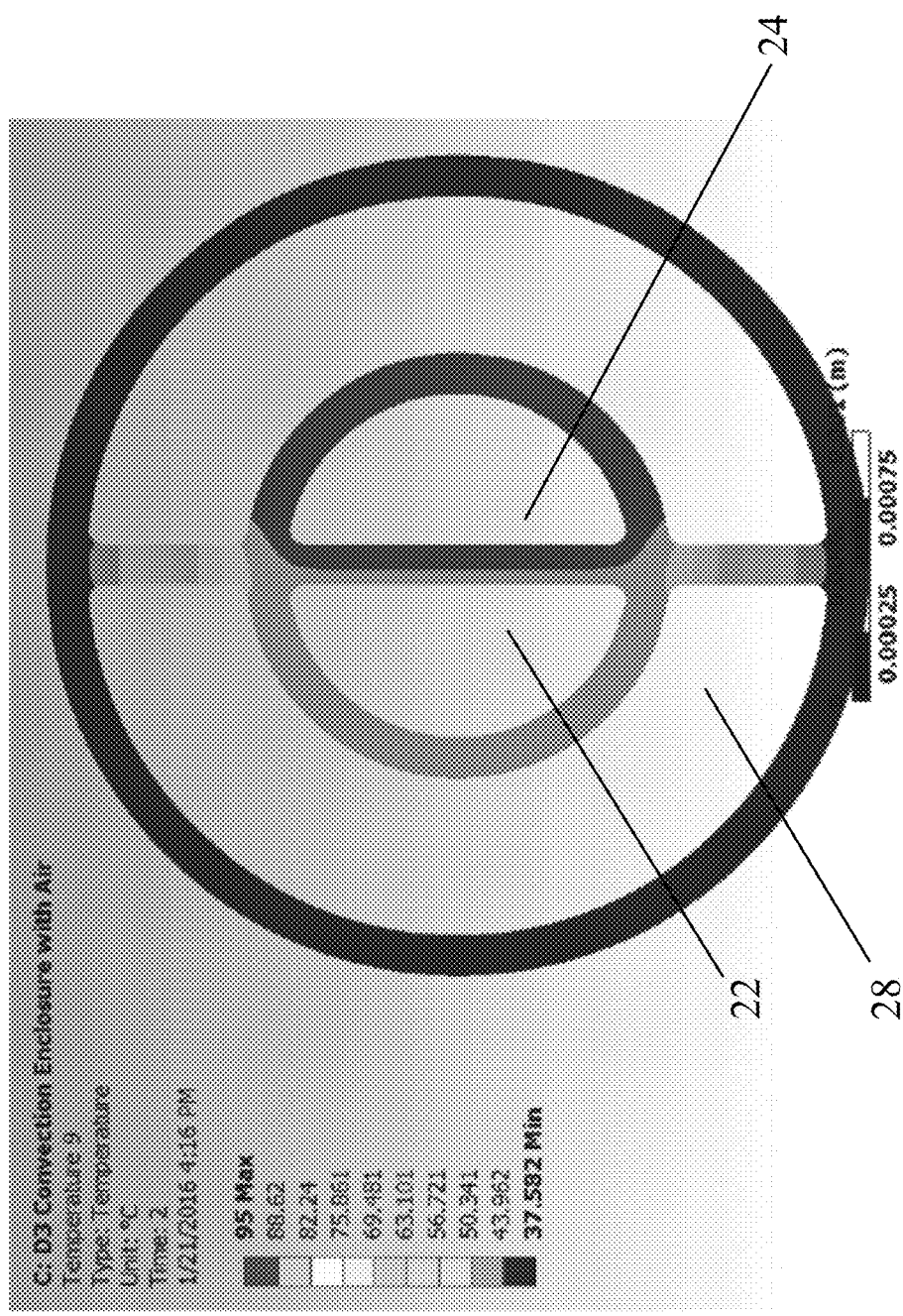

In some embodiments, as seen in FIGS. 2B and 2C, the one or more inflow lumens 22 may carry heated liquid into the balloon 25, and the one or more outflow lumens 24 may carry cooled liquid out of the balloon 25, with both sets of lumens configured to operate continuously. A spatial relationship of the lumens 22, 24 within the catheter 20 may be arranged to minimize a thermal transfer between the inflow and outflow liquid streams, and between these streams and a patient's blood and tissues. The catheter 20 may also have additional features to minimize thermal loss such as a thermal insulating material 27 or air pockets 28 (as seen in FIGS. 2C and 2D) surrounding the inflow lumens 22-24, such that the flow lumens 22, 24 are thermally insulated and may have different temperatures (as seen in FIG. 2D, where the inflow lumen 22 carrying heated fluid is at a different temperature than the outflow lumen 24).

Referencing FIG. 2 and FIGS. 3A-3C, in some embodiments the system 1 comprises an infusion device 10 having one or more fluids chambers 102-104 serving as fluid reservoirs. In some embodiments, the infusion device 10 may be connected to the proximal end 21 of the catheter 20 so that its fluid chambers 102-104 may be in fluid communication with the inflow and outflow lumens 22, 24 of the catheter 20 and the balloon 25. Each chamber 102-104 may communicate with the balloon 25 through its own lumen. In some embodiments, an inflation chamber 102 and inflow chamber 103 will each communicate with the balloon 25 through the same inflow lumen 22 while an outflow chamber 104 communicates through the outflow lumen 24. In some embodiments, each chamber 22-24 may have its own separate infusion device (not pictured).

In an embodiment, the fluid chambers 102-104 may include one inflation chamber 102, and two flow chambers 103, 104. The chambers 102-104 are generally elongate structures having proximal 105 and distal 106 ends, but can be of any shape. For the sake of consistency, the ends will be designated so that the distal end 106 of each chamber 102-104 communicates with the proximal end 105 of one or more of the catheter lumens 22-24. The chambers 102-104 generally possess axial symmetry with a cross sectional profile that is most commonly circular but can also be a more complex shape. The chamber walls may include a proximal wall, a distal wall and a contiguous radial wall extending between the proximal and distal wall. The chamber walls may be rigid and may be constructed of any material compatible with the fluid to be infused, including plastic (e.g. polycarbonate, polyethylene, PEEK, ABS, nylon), glass or metal (e.g. stainless steel, aluminum, copper, brass) or some combination thereof.

In some embodiments, the inflation chamber 102 may serve as a reservoir for fluid which will be infused through the inflow lumen 22 to inflate the balloon 25 to a desired pressure and volume. The flow chambers 103, 104 may serve as reservoirs for the fluid that will continuously flow through the balloon 25 following inflation to maintain the desired therapeutic effect (e.g., constant temperature, drug concentration, etc.). For consistency, the flow chambers 103, 104 will be designated based on the direction of fluid flow relative to the balloon 25, not the chamber. Thus, the inflow chamber 103 serves as a reservoir from which fluid can be infused into the inflated balloon 25, and the outflow chamber 104 may serve as a reservoir to receive fluid that flows out of the inflated balloon 25.

Each chamber 102-104 may have one or more ports 107 through which fluid flows into (inlet port) or out of (outlet port) the chamber 102-104. Each port 107 may be associated with a valve 101 to control flow through the port 107. Each chamber 102-104 may communicate with the balloon 25 through its own lumen. In some embodiments, the infusion device 10 may have a heating mechanism 108 to heat the liquid in the inflow chamber 103. In some embodiments, the heating mechanism 108 may heat the liquid in the inflation chamber 102 so that the initial inflation can be performed with heated liquid, and in other embodiments the heating mechanism 108 may heat the liquid in the outflow chamber 104 provided the system 1 has the ability to reverse flow of the fluid and recirculate the fluid.

Figure 3A:
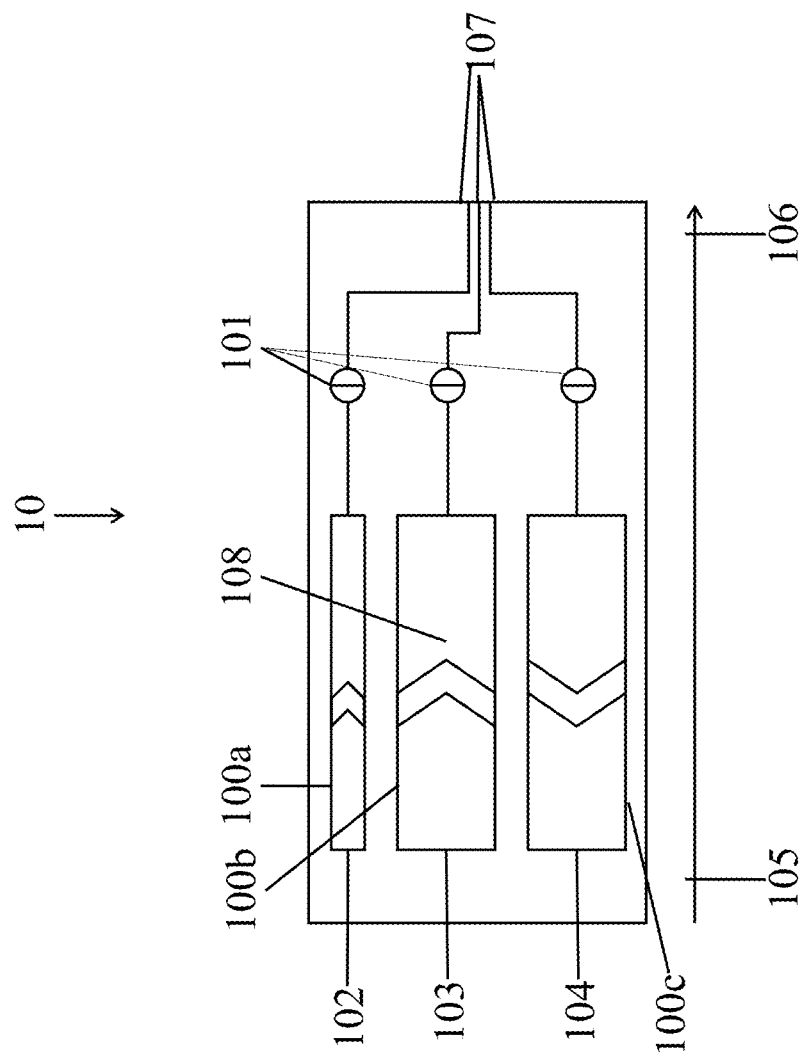
Figure 3B:
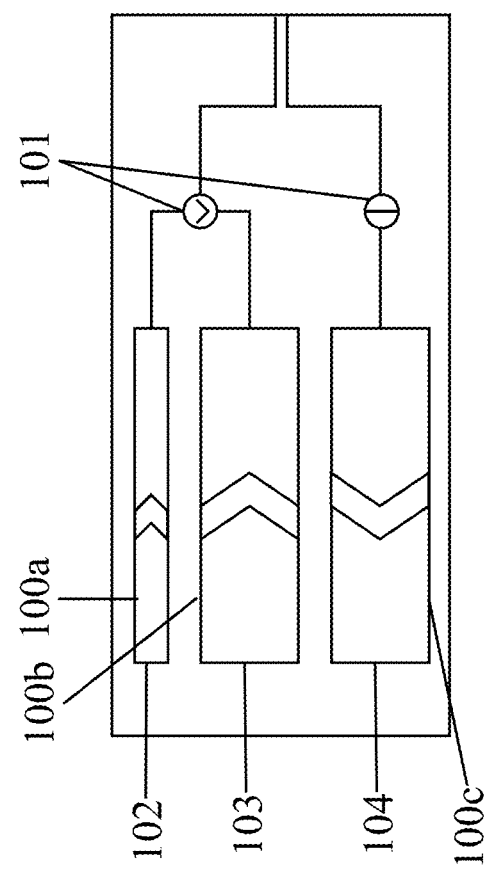

In some embodiments, as seen in FIG. 3B, the inflation chamber 102 and inflow chambers 103 will each communicate with the balloon 25 through the same inflow lumen 22, while the outflow chamber 104 communicates through the outflow lumen 25. In another embodiment, as seen in FIG. 3C, the inflation chamber 102 may flow into the inflow chamber 103. Each chamber 102-104 may have an infusion mechanism 100a-100c which drives fluid out of or back into the chamber 102-104 and one or more valves 101 to control the flow of fluid in and out of the chamber 102-104.

Figure 4A:
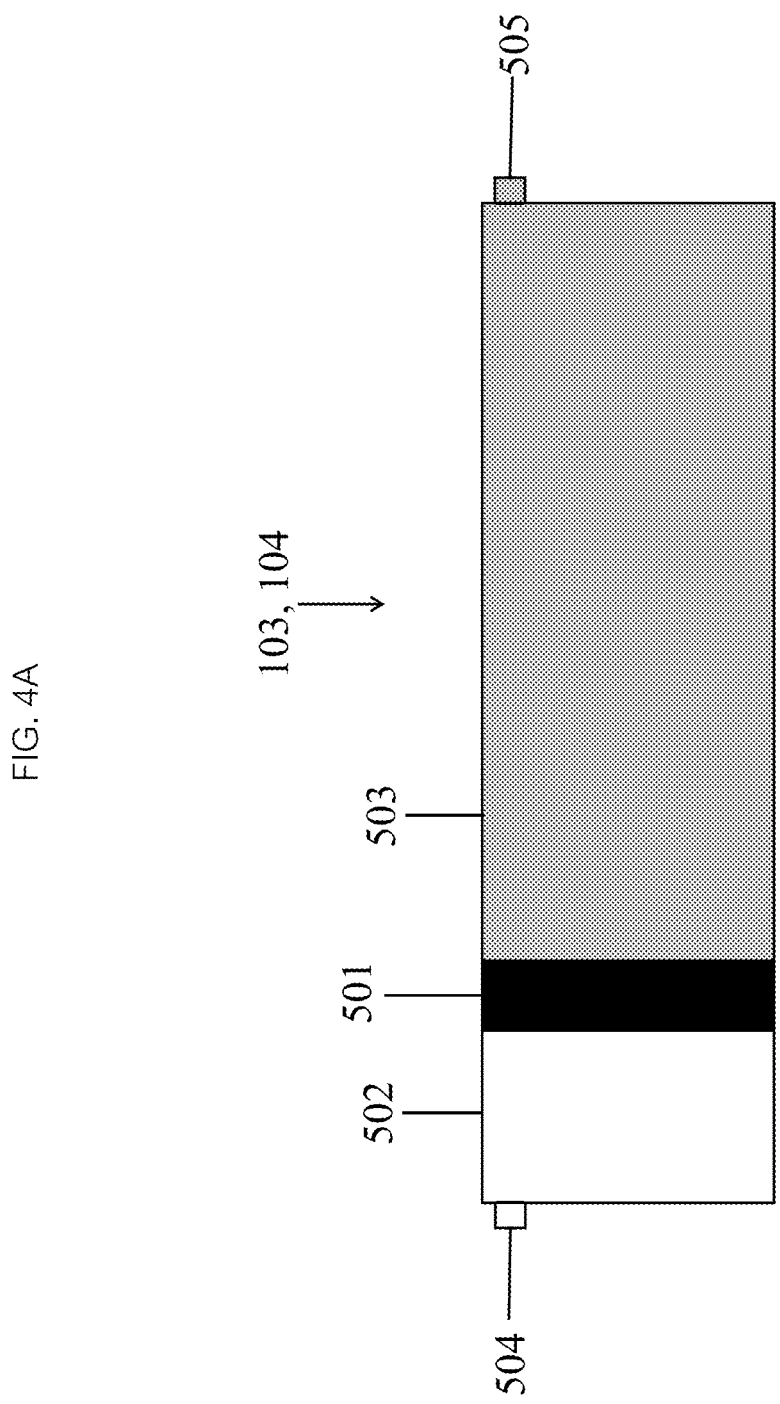
FIG. 4A illustrates an infusion mechanism for controlling fluid being dispensed from the infusion device, in accordance with an embodiment of the present disclosure.
Figure 4B:
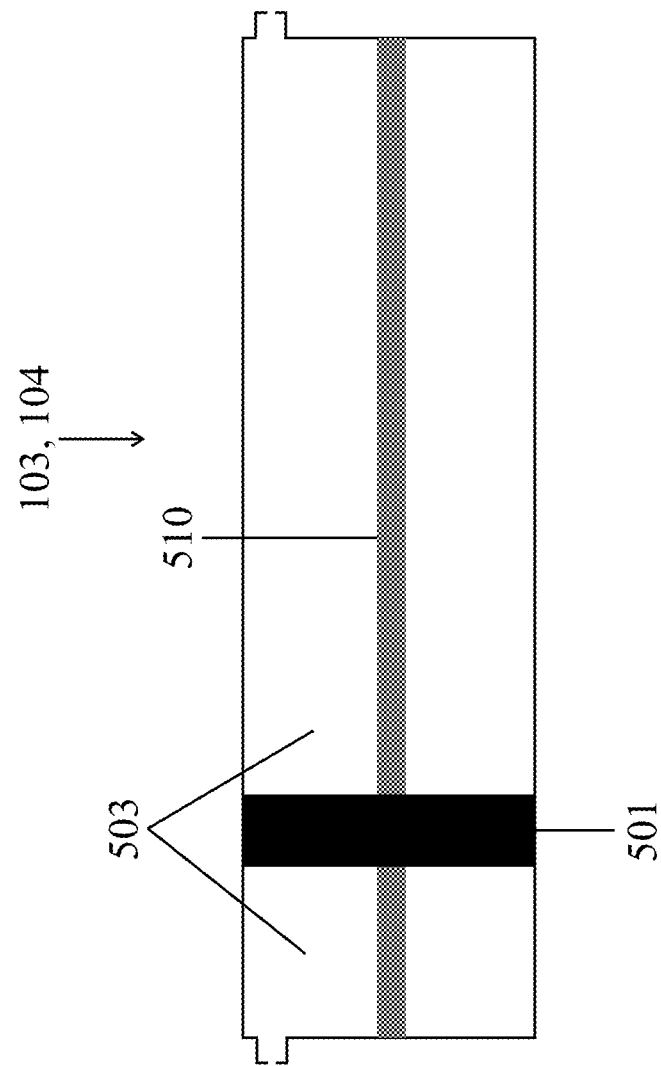
FIGS. 4B-E illustrate various configurations/designs for an internal heating element for heating fluids in the infusion device in accordance with the present disclosure.
Figure 4C:
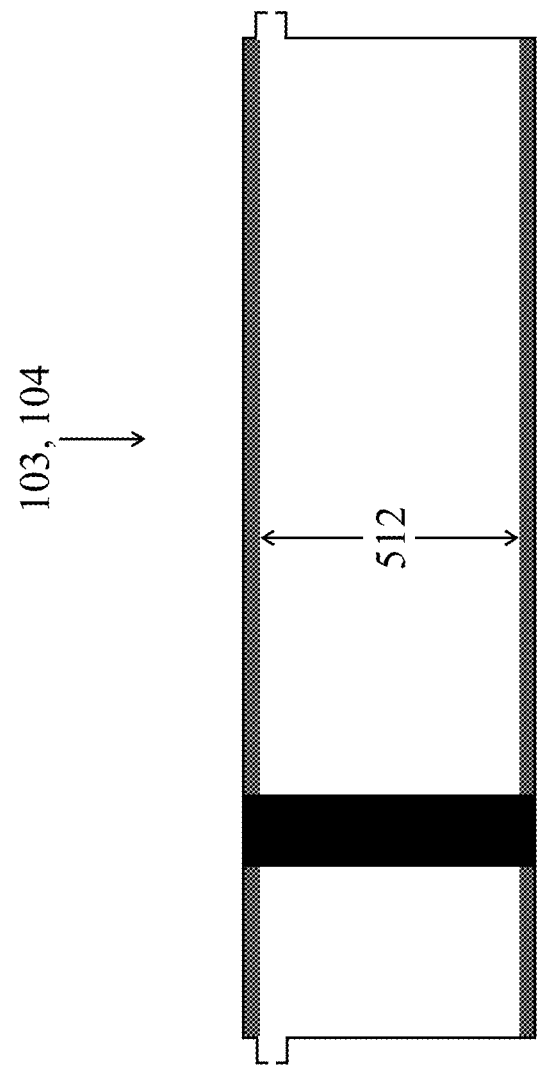
Figure 4D:
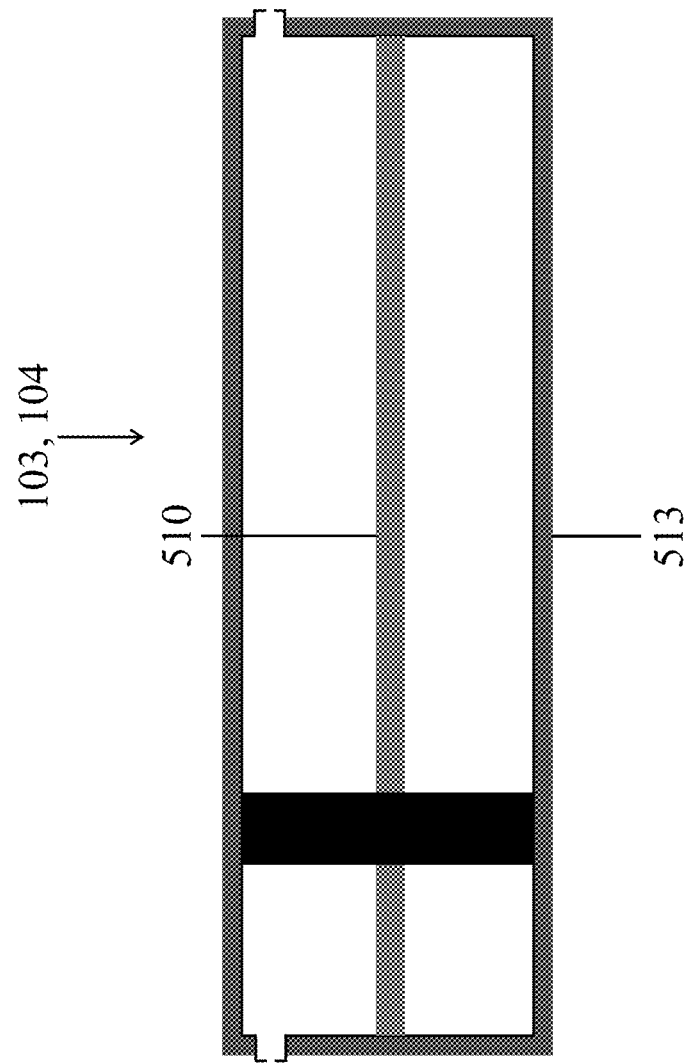
Figure 4E:
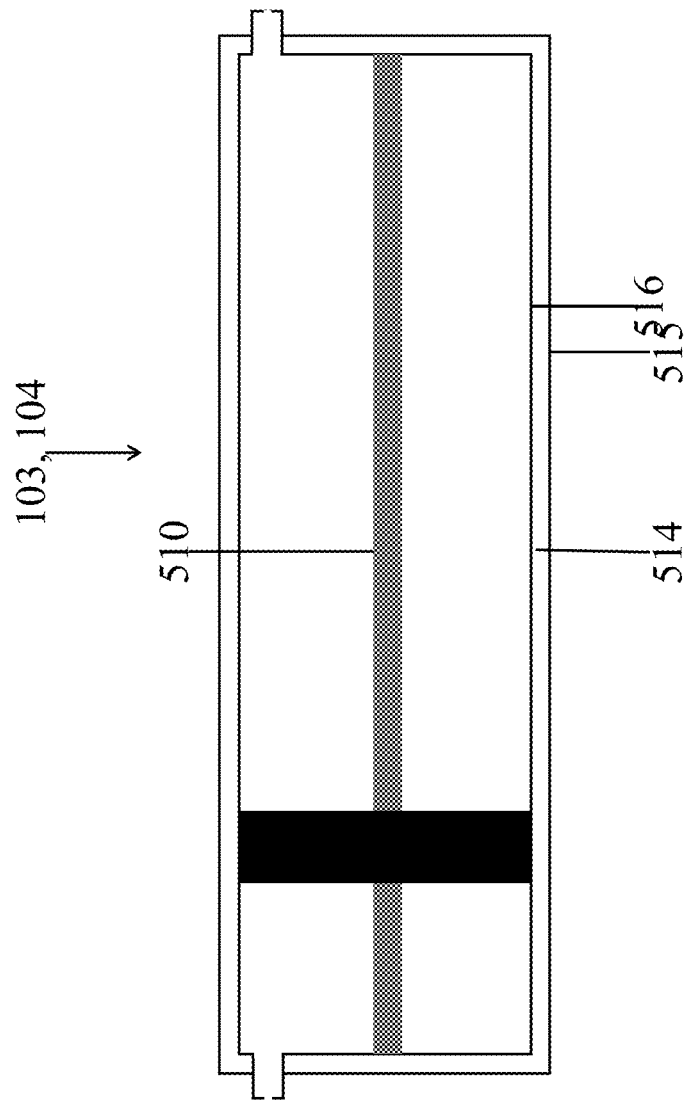

Referring now to FIGS. 4A and 5A, the infusion mechanism of each chamber 103, 104 may include a piston 501 which controls the volume of fluid in the chamber 103, 104 and an associated drive mechanism 600. The piston 501 may be a flat, discoid structure with the same cross sectional profile as the chamber 103, 104, and may divide the chamber 103, 104 into two sub-chambers, a fluid sub-chamber 503 and an air sub-chamber 502. Each sub-chamber 502, 503 may have one or more ports 504, 505. The piston 501 has two surfaces, orthogonal to the axis of the chamber 103, 104. An internal surface faces inside of the fluid sub-chamber 503 and can be exposed to the fluid within it while an external surface may be on an opposite side of the chamber 103, 104 and may be exposed to air outside the chamber 103, 104. In certain embodiments, the piston 501 may be shared with another chamber so that its external surface can be exposed to fluid in the other chamber, thereby eliminating the air sub-chamber 502 altogether. The piston 501 moves axially within the chamber 103, 104, decreasing or increasing the fluid sub-chamber's 503 volume, driving fluid out of or drawing fluid into the sub chamber 503. In order to form a fluid-tight seal against an inner chamber 103, 104 wall, the piston 501 may comprise a compliant, rubbery material (e.g., natural rubber, silicone) or a rigid material (e.g., plastic, metal) with a rubbery gasket. In some embodiments, the piston 501 may be passive, in other embodiments it may be active. The passive piston 501 moves along an axis of the chamber 103, 104 as fluid is driven into or out of the fluid sub-chamber 503 by the action of another chamber. The active piston may be connected to a drive mechanism 600 which exerts a mechanical force on the piston 501 and moves it along the axis of the chamber 103, 104.

In some embodiments, once the balloon 25 is inflated to the desired volume and pressure, the flow of liquid into and out of the balloon 25 is matched to keep the balloon 25 volume and pressure constant while continuously replenishing the heated liquid in the balloon 25, while at the same time withdrawing the liquid that is cooled by the patient. In some embodiments, the inflow 103 and outflow 104 chambers are mechanically linked via their drive mechanisms 600 so that each piston 501 has a movement that is equal and opposite to the other piston 501. As a result, a total volume of liquid in the inflow 103 and outflow 104 chambers remains constant throughout the infusion period.

In some embodiments, the inflation 102, inflow 103 and outflow 104 chambers may be discrete structures, communicating separately with the balloon catheter 20 inflow 22 and outflow 24 lumens. In some embodiments, two or more chambers may be combined into a single structure, sharing their pistons 501 and/or drive mechanisms 600. In some embodiments, the infusion device 10 may have a shared inflow/outflow chamber facilitating heating of the liquid in both chambers, permitting multiple infusion cycles. Another embodiment may comprise all three chambers in a single structure permitting all chambers, including the inflation chamber, to be heated with a single external heating element which allows the initial balloon 25 to be inflated using heated liquid, decreasing the ablation time.

Referring now to FIGS. 4B-4E, in some embodiments the infusion device comprises one or more heating elements 510. The heating element 510 may be internal, residing within one or more fluid chambers 103, 104. The internal heating element 510 may comprise probes, coils, wire, foil, thin film resistors 512 and thick film resistors. If internal heating elements 510 are utilized, all or portion of the chamber wall 515 may be insulated to minimize ambient heat loss (e.g., by using an insulating jacket 513 or by interposing a gas or vacuum 514 between an inner 516 and an outer chamber wall 515, similar to a thermos).

Figure 5B:
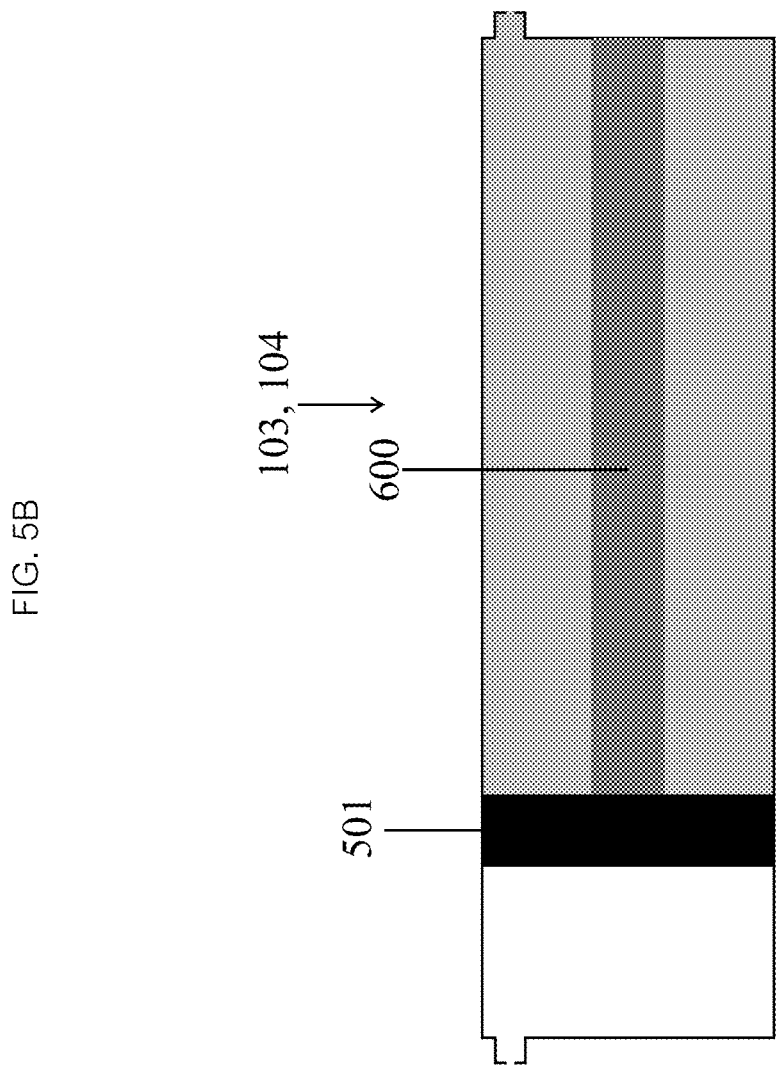
Figure 5D:
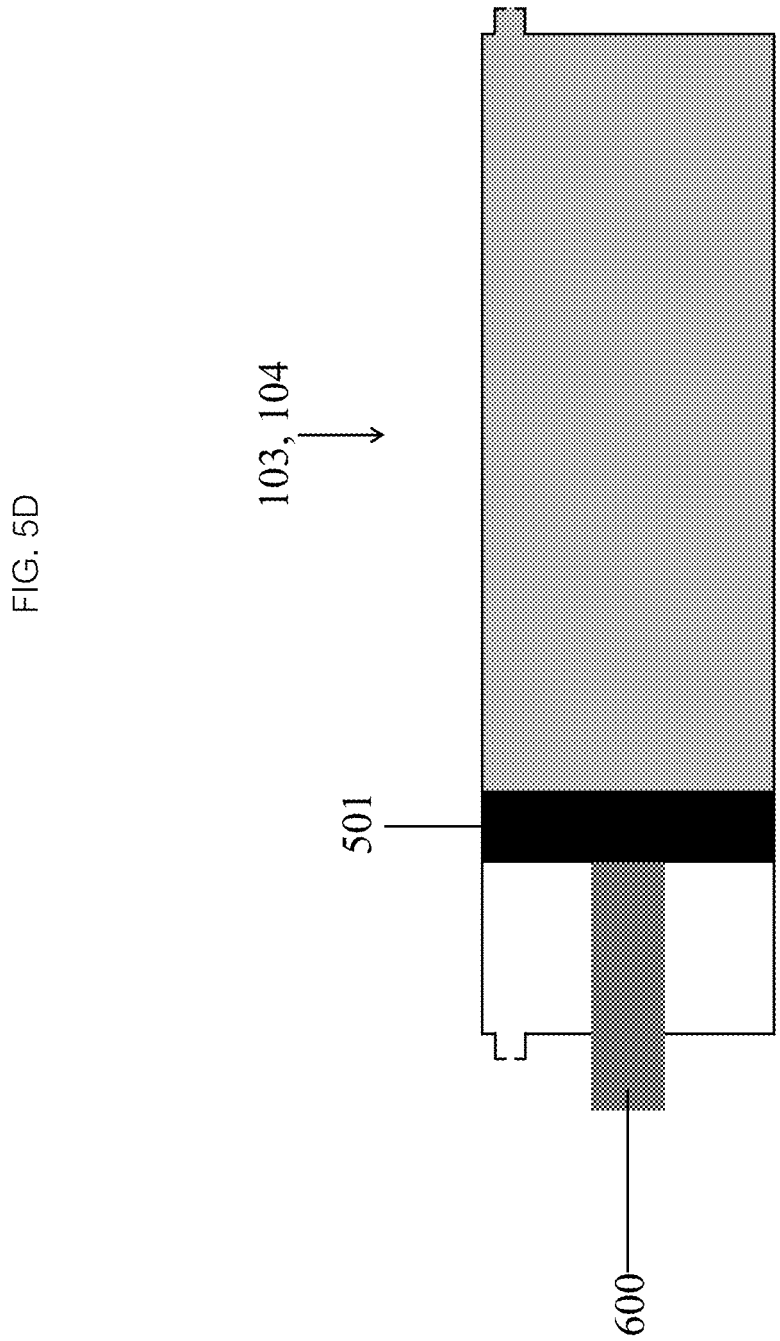
Figure 5E:
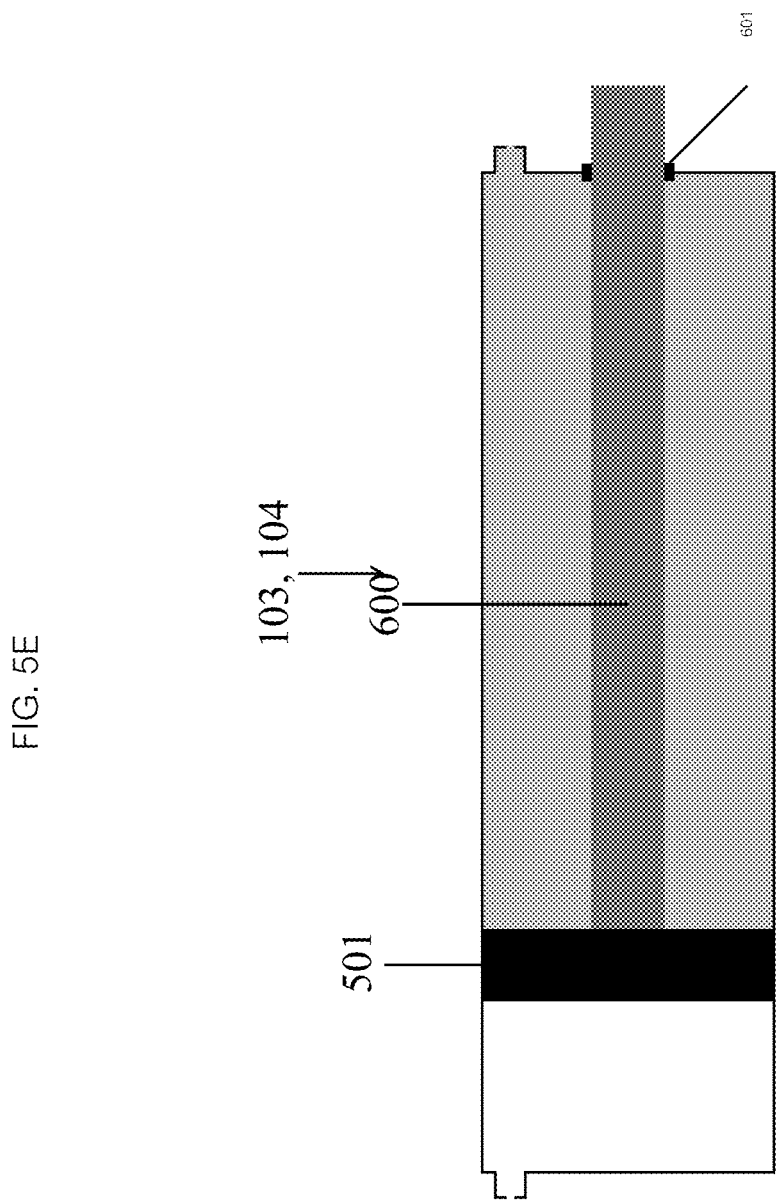
Figure 5F:
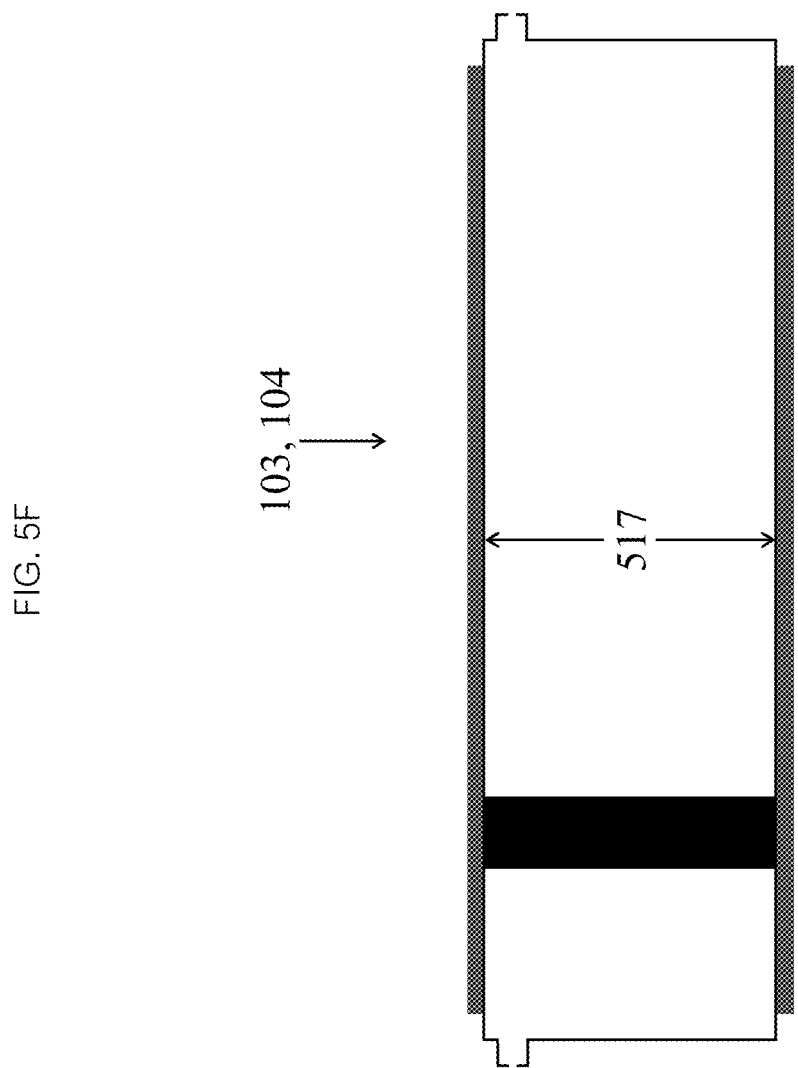

In some embodiments, referring to FIGS. 5F and 5G, the heating element 510 may also be external. In some embodiments, the heating element 510 may be in contact with the wall of an individual chamber 103, 104 or wrapped around one or more chambers. Such a heating element may be a heating jacket 517 in contact with at least a portion of the surface area of the chamber 103, 104. In some embodiments, a specific heating element 510 within the jacket 517 may comprise probes, coils, wire, foil, thin film resistors and thick film resistors. In some embodiments the chamber wall would be designed to maximize thermal transfer, through selection of a chamber wall material and thickness, and/or wrapping or coating the chamber wall with a material of high thermal conductivity. In some embodiments, the chamber 103, 104 may have an outer 518 and inner wall 519 separated by a gas or vacuum 520 to minimize ambient heat loss with the external heating residing within a space in contact with the inner wall.

Referring now to FIGS. 5A-E, in some embodiments the drive mechanism 600 (as seen in FIG. 5A) may be manual, powered by an operator through the manipulation of a mechanical actuator (not pictured), or alternatively, by an autonomous, passive mechanical or active electromechanical source. The drive mechanism 600 may extend across the chamber (as seen in FIG. 5C), be contained entirely within a sub-chamber (as seen in FIGS. 5A and 5B) or a portion may extend through an end wall of the sub-chamber (as seen in FIGS. 5D and 5E). If a portion of the drive mechanism 600 passes through the end wall of the fluid sub-chamber, it must pass through a gasketed port 601 to maintain a fluid seal. The drive mechanism 600 may be connected to the internal or external surface of the piston 501.

Figure 6A:
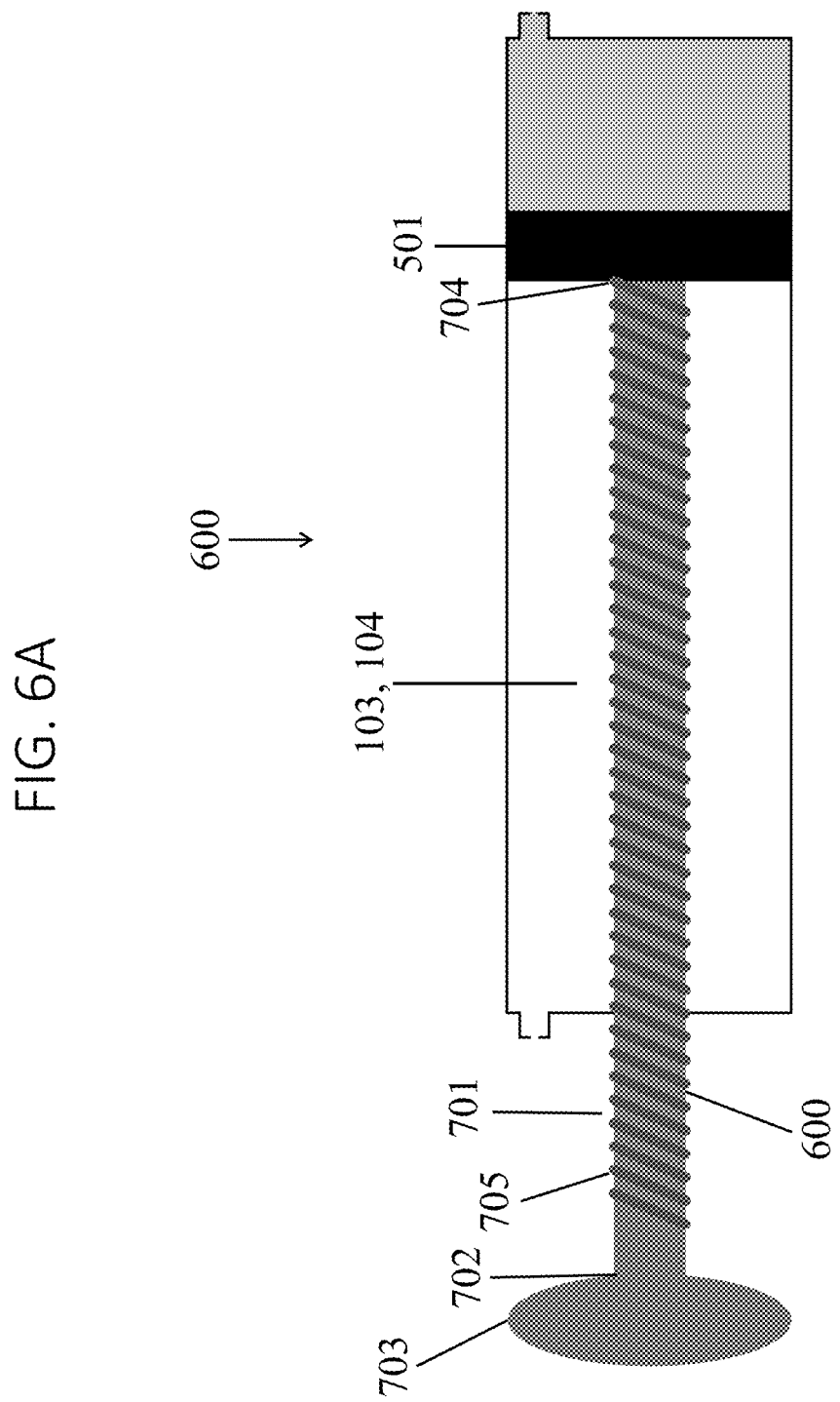
Figure 6B:
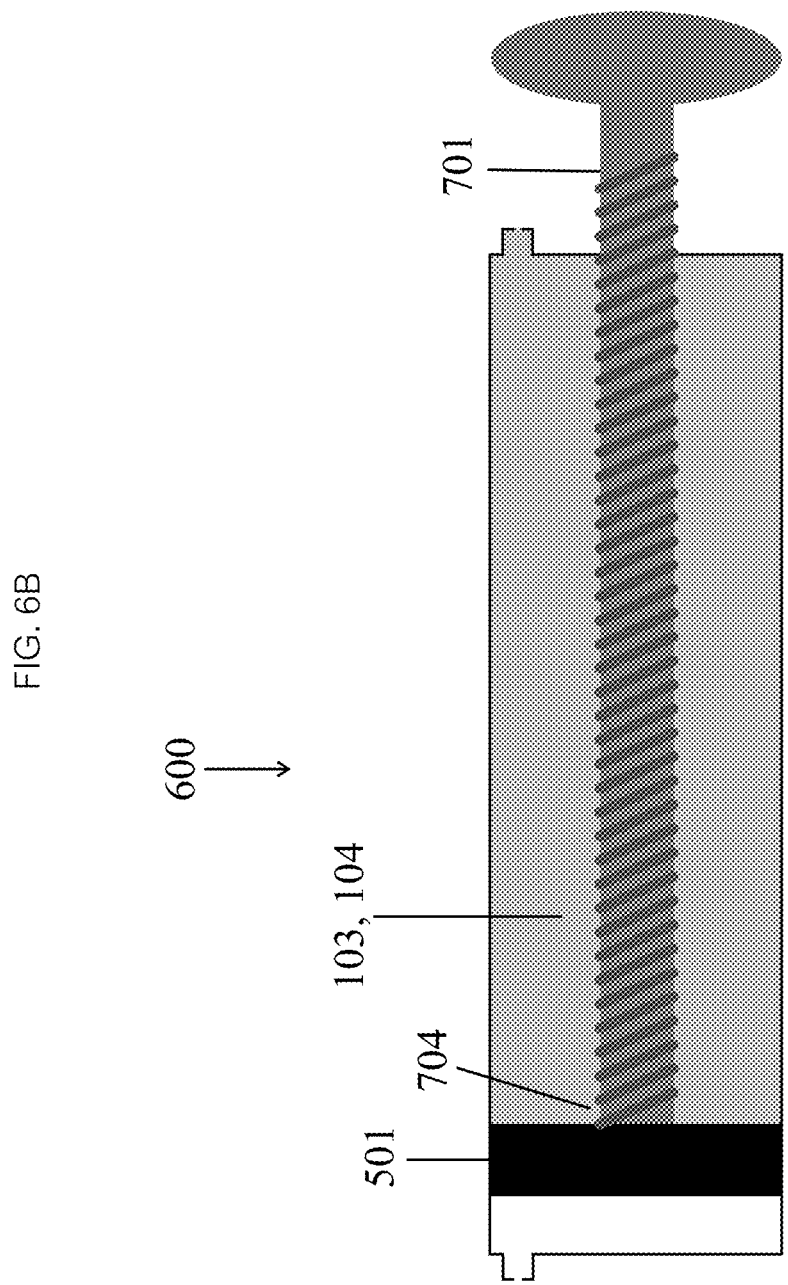
Figure 6C:
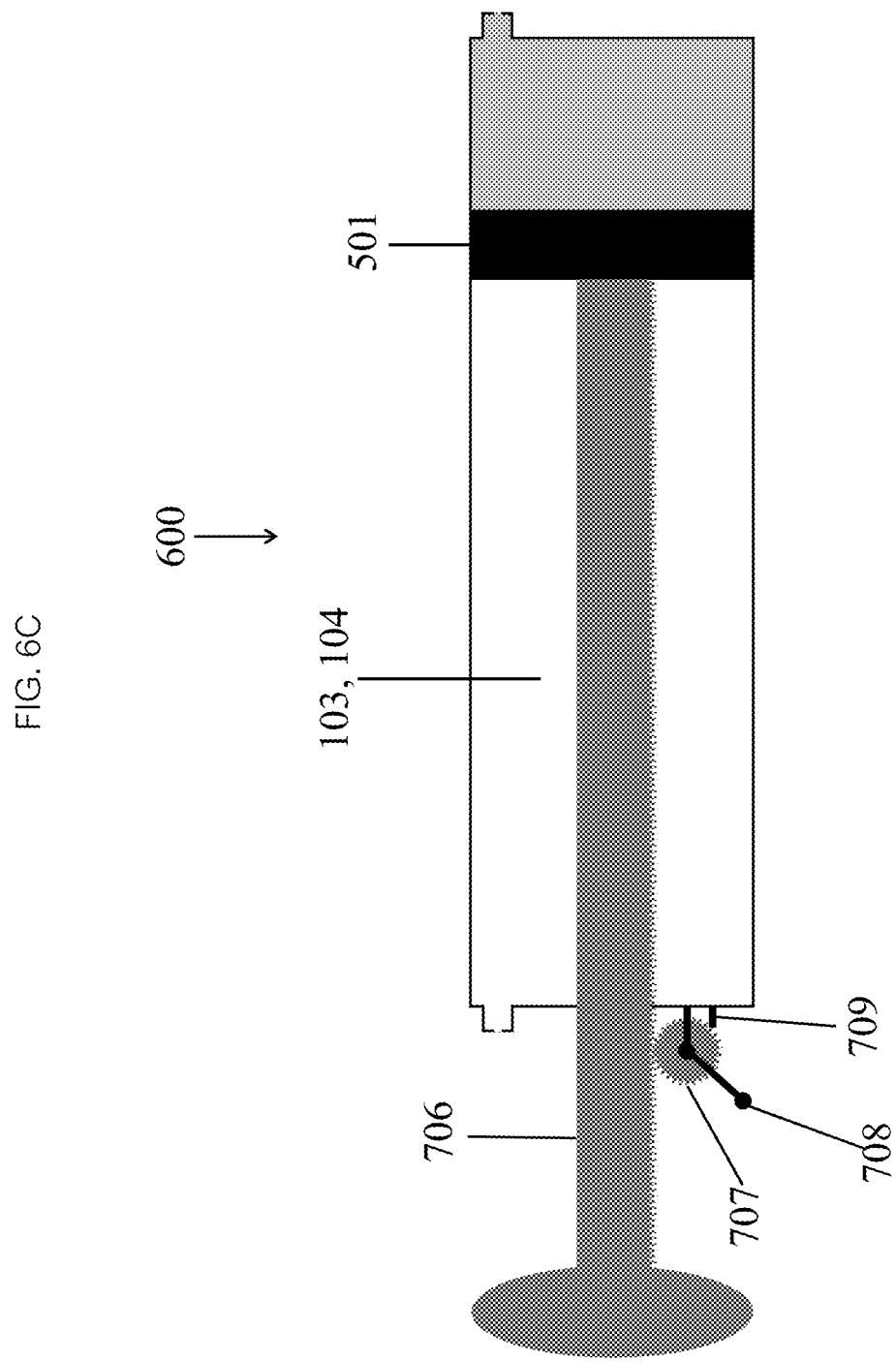
Figure 7:
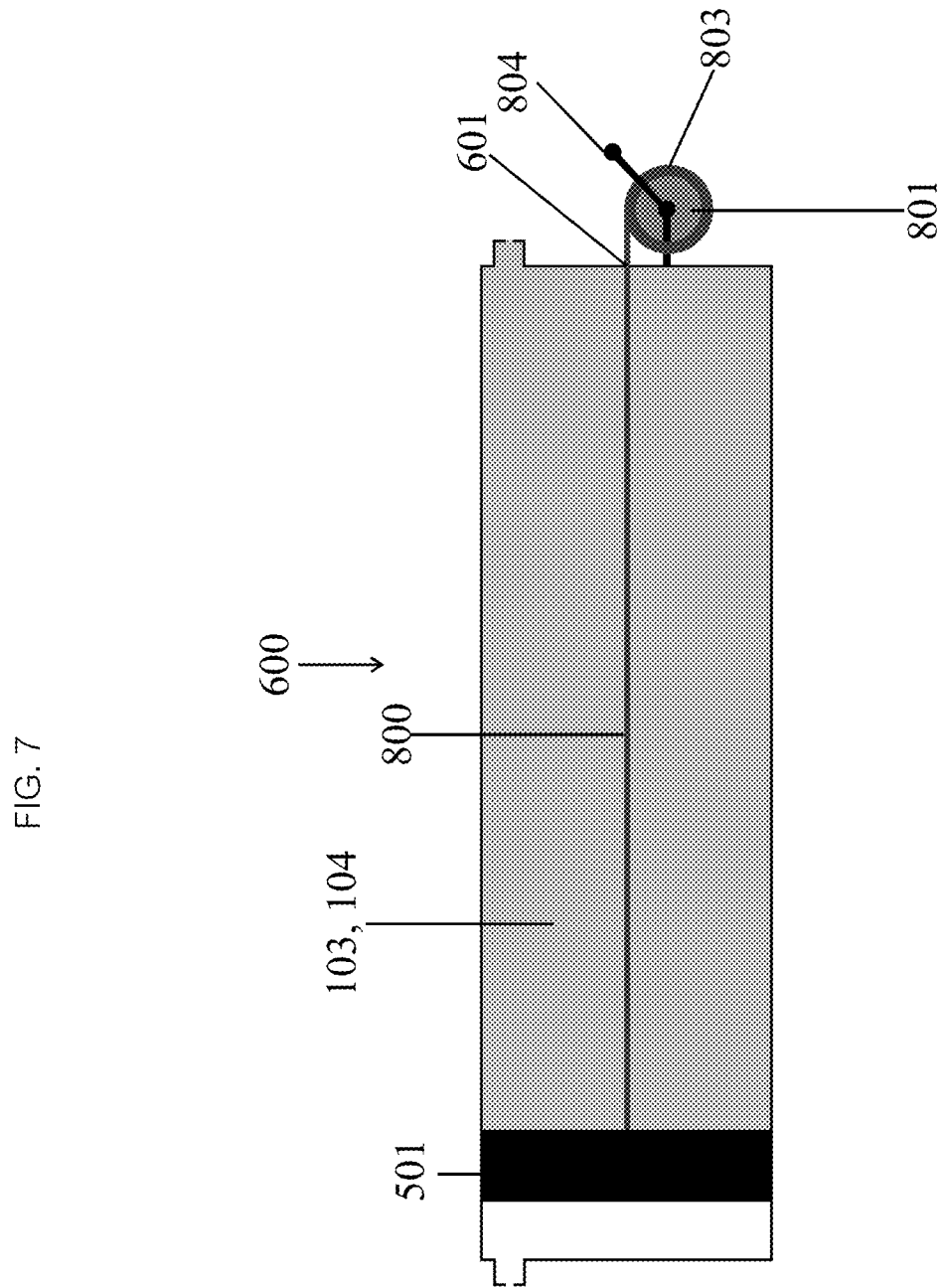

In some embodiments the manual drive mechanism 600 may comprise a syringe-like plunger (simple, threaded or ratcheted), a cable or cord attached to a crankshaft or knob-driven pulley (simple or ratcheted), a fixed length belt or chain attached to a crankshaft or knob-driven pulleys or gears, a lead (translation) screw. In some embodiments, a passive powered drive mechanism is based on a spring (e.g., compression, extension, or rotary drives). In some embodiments, an active powered drive mechanism may be based on an electric motor powering a cable/pulley, belt/chain or lead screw drive mechanism. Referring to FIG. 6A, the manual drive mechanism 600 may include a rigid rod 701, similar to a plunger in a standard syringe, whose proximal end 702 has a handle 703 which may facilitate axial movement of the rod 701 and whose distal end 704 is attached to the internal or external surface of the piston 501. In an embodiment where the distal end 704 is attached to the external surface (as seen in FIG. 7) of the piston 501, the drive mechanism 600 may function like the plunger in a standard syringe, moving the internal surface against the fluid in the chamber 103, 104. In some embodiments (as seen in FIG. 6B), the distal end 704 is attached to the internal surface of the piston 501, whereby it traverses the fluid chamber 103, 104 and exits through a gasketed port 601, moving the interior surface of the piston 501 against the fluid chamber 103, 104 in a "reverse syringe" fashion. In some embodiments, the operator manually advances or withdraws the rod 701, moving the piston 501 in either direction, driving fluid out of or drawing fluid into the chamber 103, 104. The rod 701 may have a threaded screw 705 or ratcheting mechanism 706 (as seen in FIG. 6C) which allows the piston 501 and rod 701 to maintain their position under pressure via the use of a ratchet lock 709, crankshaft 708 and gear 707.

Figure 6D:
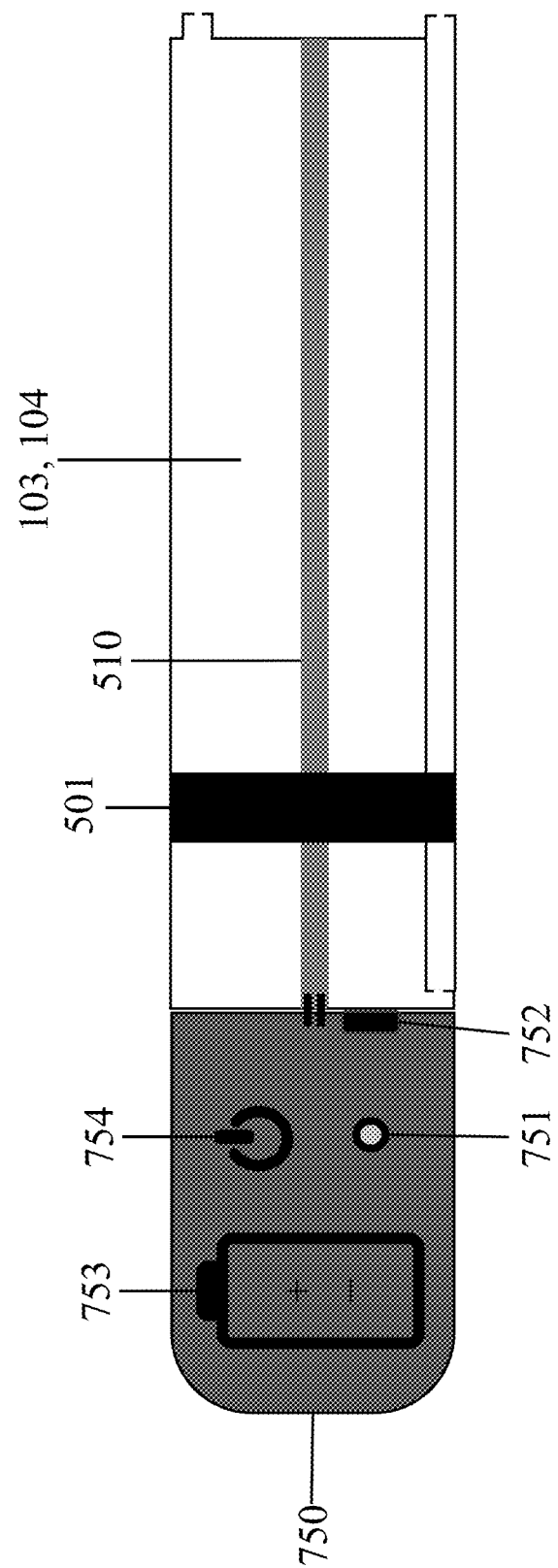
FIGS. 6D-E illustrate various models for controlling the heating element used in accordance with the present disclosure.
Figure 6E:
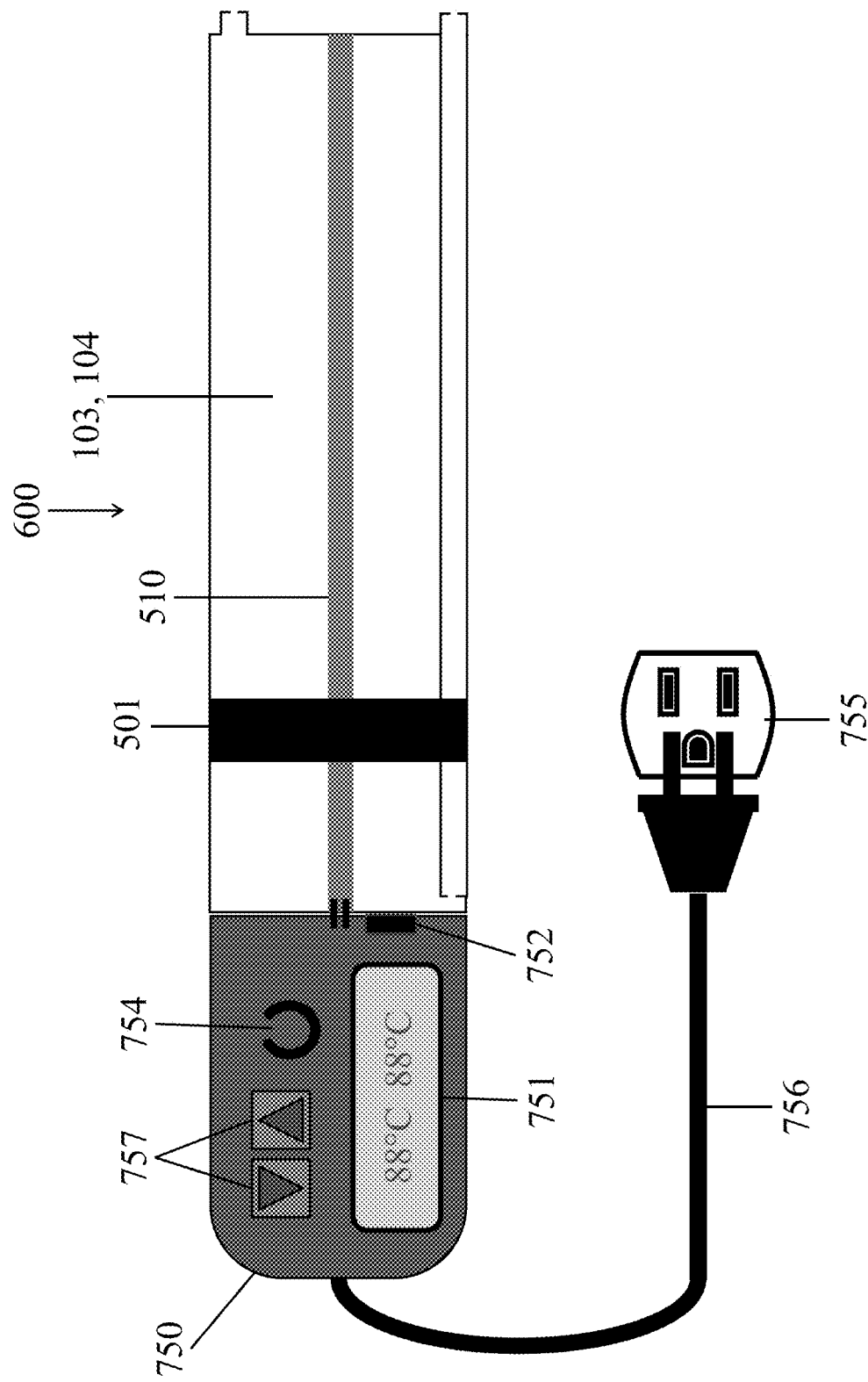

Referring now to FIGS. 6D and 6E, in some embodiments the heating element 510 may require some additional electrical circuitry to function. In some embodiments, the electrical circuitry may comprise an electrical power source 750, a control with a temperature sensor 752 and a display 751 which is configured to indicate that the target temperature has been reached. In some embodiments, the electrical power source 750 may comprise a disposable DC battery 753. In some embodiments, the electrical power source 750 may comprise AC power (as seen in FIG. 6E) supplied from a wall outlet 755 through a disposable sterilized power cord 756 passed off a sterile field. AC power, of course, would be able to provide more power, thereby decreasing the time required to achieve the target temperature and increasing the potential ablation time. The sensor/display 751, 752 may be a simple analog thermometer, in contact with the liquid or the chamber wall, without any electrical connection (e.g., a standard mercury or alcohol column or a thermochromatic film commonly used to measure skin temperature). In some embodiments, the sensor 752 may comprise an electrical thermocouple in electrical communication with a display 751. Many heating elements have built-in thermocouples. In some embodiments, the display 751 may be one or more binary optical indicators (e.g., an LED) that indicate that the temperature is in range. Alternatively, in some embodiments the display 751 may be a digital or analog display that shows the actual temperature. In some embodiments, the power source 750 may further comprise a manual on/off power switch 754. The operator may manually turn the switch 754 on to activate the heating element 510 and heat the liquid, and may turn the switch 754 off when the target temperature has been reached. Alternatively, the power source 750 may be controlled by a knob or pair of up/down buttons 757 to set the target temperature. In some embodiments, additional circuitry may be required to create a temperature feedback loop, automatically adjusting power to maintain the target temperature.

Referring now to FIG. 7, in some embodiments, the manual drive mechanism 600 comprises a cord or cable 800 attached to the exterior or interior surface of the piston 501 exiting the fluid chamber 103, 104 (through a gasketed port 601 in the latter case). The operator pulls the cable or cord 800, shortening it, drawing the piston 501 towards it and driving fluid out of or drawing fluid into the chamber 103, 104. In some embodiments, the cable or cord 800 may be attached to a ratcheting mechanism 801 which locks its position as its being withdrawn. In some embodiments, the ratcheting mechanism 801 may be reversible. The cable or cord 800 may also be engaged onto a pulley 803, which may be fixated on an outside of one end of the chamber 103, 104. The pulley 803 may have a crankshaft 804 or knob with or without a ratcheting lock mechanism. The operator turns the crankshaft 804 or knob, wrapping a length of the cable or cord 800 onto the pulley 803, shortening it, while drawing the piston 501 towards it and driving fluid out of or drawing fluid into the chamber 103, 104.

Figure 8:
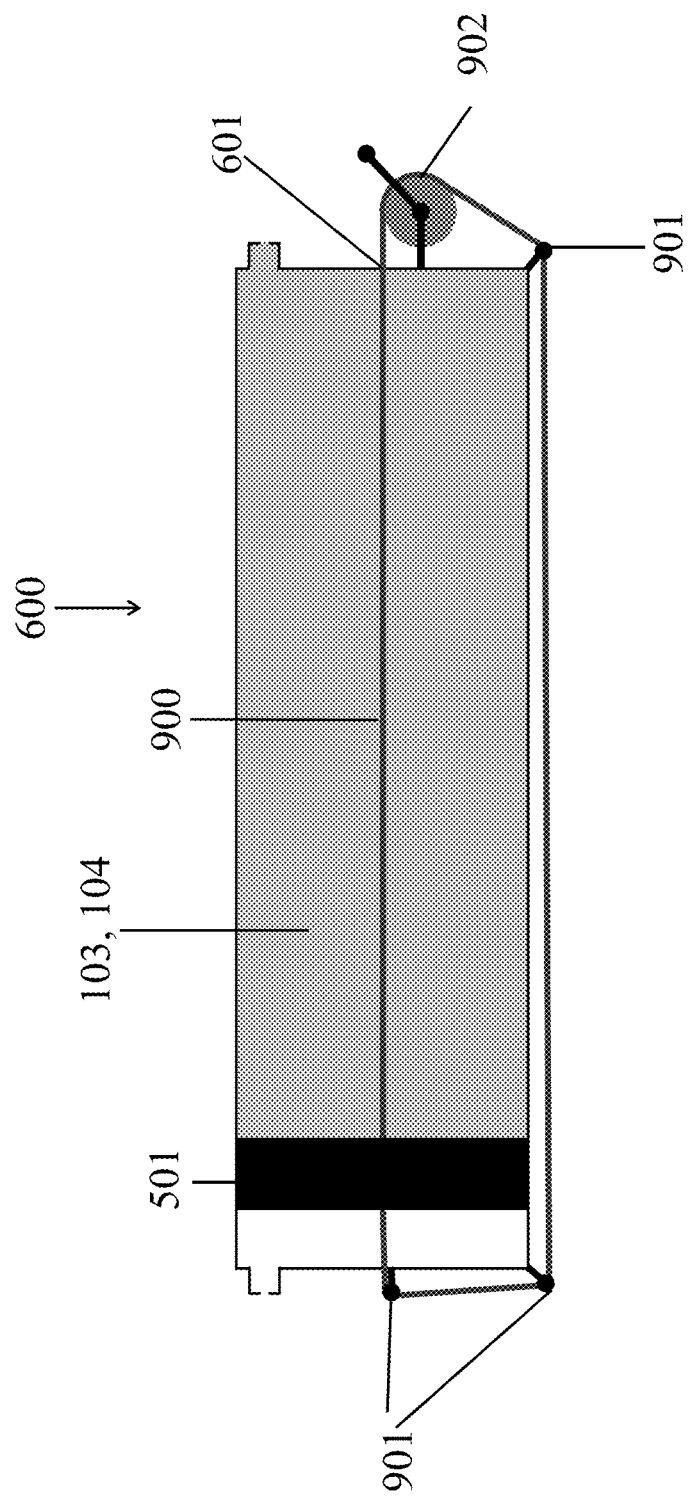

Referring now to FIG. 8, in some embodiments, the drive mechanism 600 may comprise a fixed length belt or chain 900. The belt or chain 900 may be attached to the interior surface of the piston 501, exiting the fluid sub-chamber 103, 104 and wrapping around the length of the chamber 103, 104 through a series of pulleys or gears 901, entering a sub-chamber and attaching to the exterior surface of the piston 501. In some embodiments, one of the pulleys/gears may further comprise a crankshaft or knob 902, with or without a ratcheting lock mechanism. The operator turns the crankshaft or knob 902, moving the belt or chain 900 clockwise or counterclockwise, drawing the piston 501 towards it and driving fluid out of or drawing fluid into the chamber 103, 104.

Figure 9B:
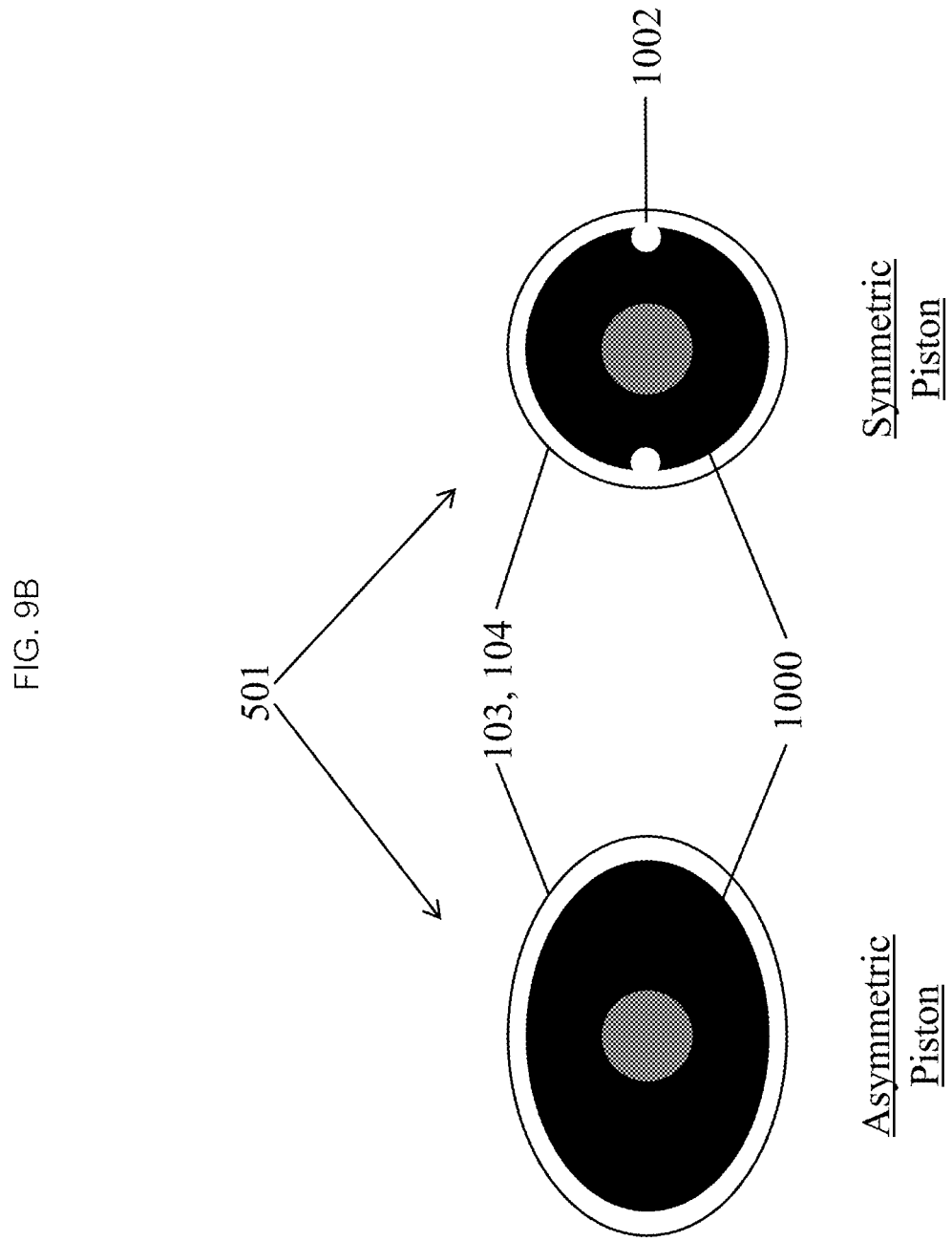

Referring now to FIG. 9A, in some embodiments the manual drive mechanism 600 may be a lead (translation) screw 1000. The screw 1000 can be positioned along the long axis of the chamber 103, 104 and anchored to one end of the chamber 103, 104 while maintaining a freedom of rotation. The screw 1000 may pass through the other end of the chamber 103, 104 through a hole in the piston 501 with a matching thread and finally through a hole in the chamber 103, 104 which may be gasketed if that portion of the screw 1000 is in contact with the fluid in the chamber. To prevent the screw 1000 from spinning, as seen in FIG. 9B, the piston 501 may be axially symmetric or asymmetric (e.g., an ellipse) or there may be one or more guide rails 1002 to keep the piston 501 from rotating. The external end of the screw 1000 can be attached to a crankshaft or knob 1001. In some embodiments, rotating the screw 1000 advances or withdraws the piston 501, driving fluid from or drawing fluid into the chamber 103, 104.

Figure 10:
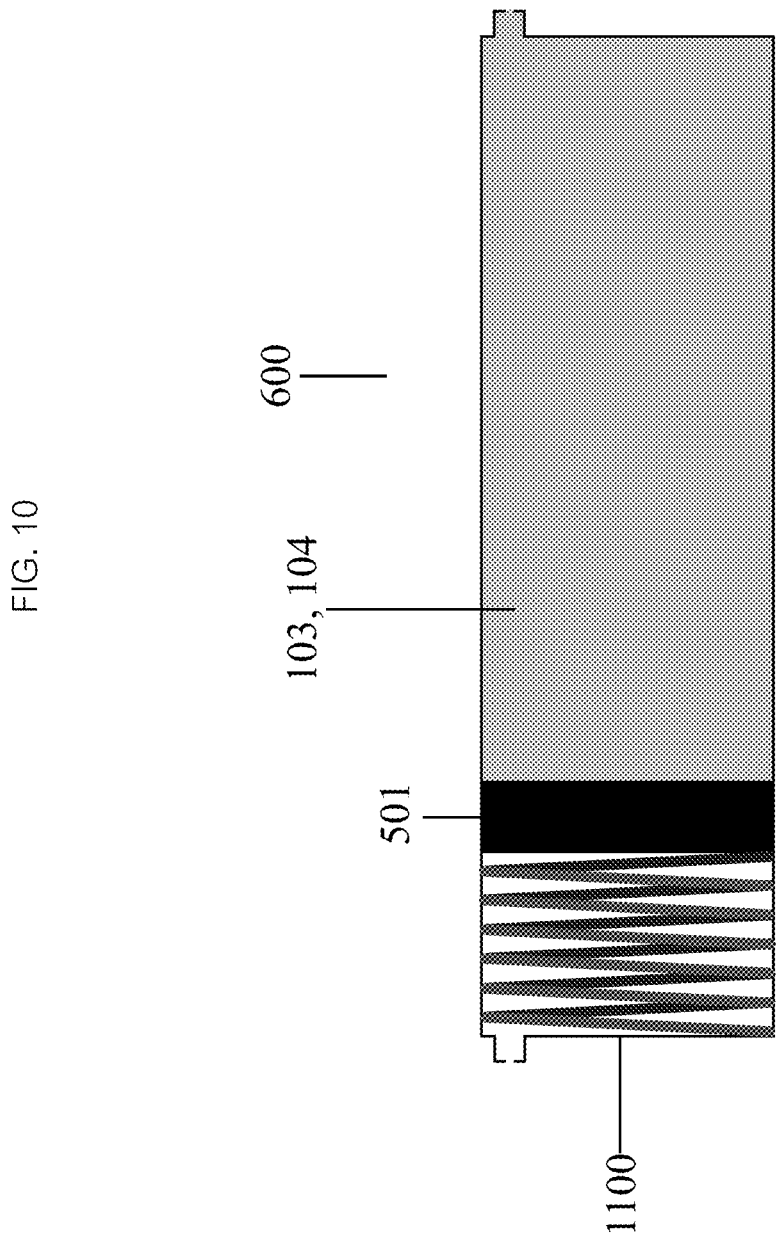
FIGS. 10 and 11A-B illustrate various automatic drive mechanisms for activating the infusion mechanism in accordance with the present disclosure.

The infusion device 10 may benefit from a passive or active autonomous powered drive mechanism 600, one that acts independent of the operator. Referring now to FIG. 10, the passive powered drive mechanism 600 may comprise a spring 1100. In some embodiments, the spring 1100 may be a compression spring, which can be positioned outside of the fluid chamber 103, 104 so that the spring 1100 is fully compressed when the chamber 103, 104 is full of fluid. When flow is initiated the spring 1100 exerts a force against the exterior surface of the piston 501, driving fluid out of the chamber 103, 104 as it expands. In some embodiments, the compression spring may be positioned in the fluid chamber 103, 104, exerting force against the interior surface of the piston 501, drawing fluid into the chamber 103, 104 as it expands. Other types of springs (e.g., extension, rotary) may also be used in additional configuration.

Figure 11A:
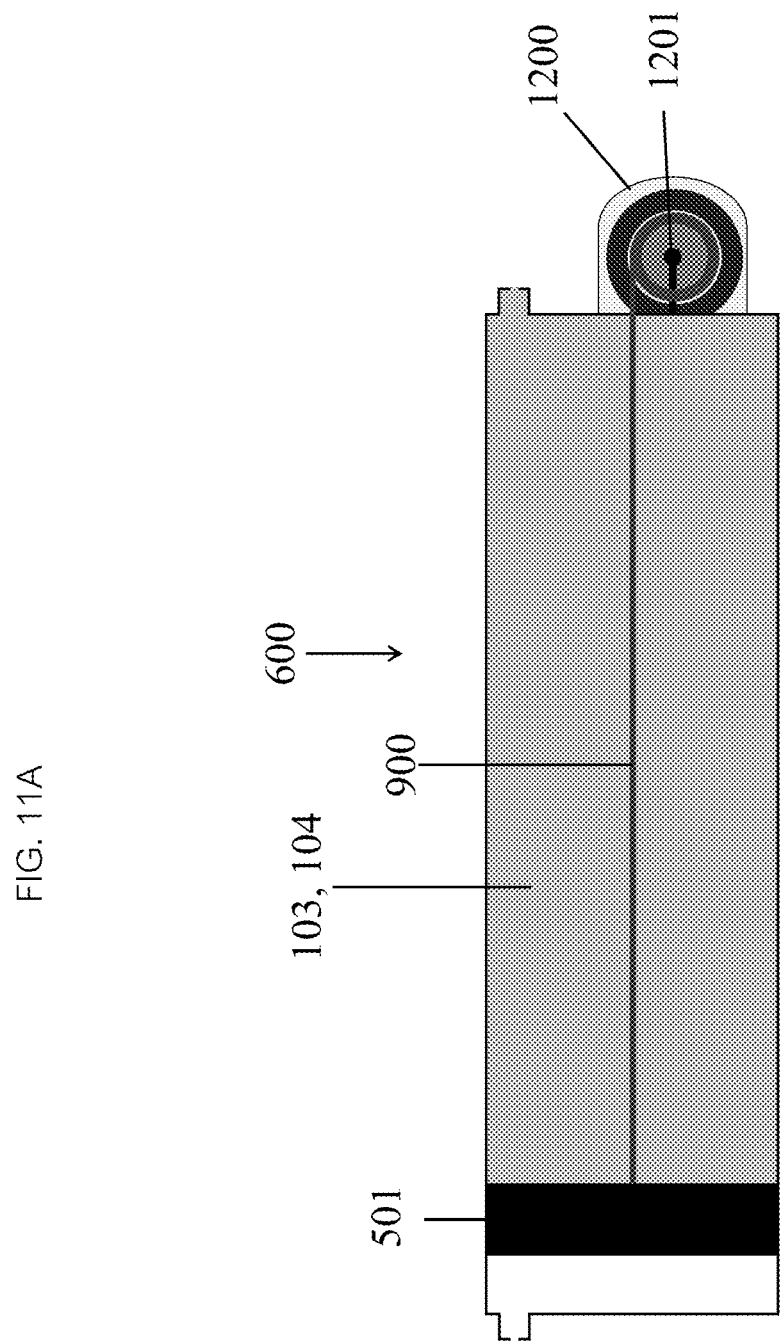
Figure 11B:
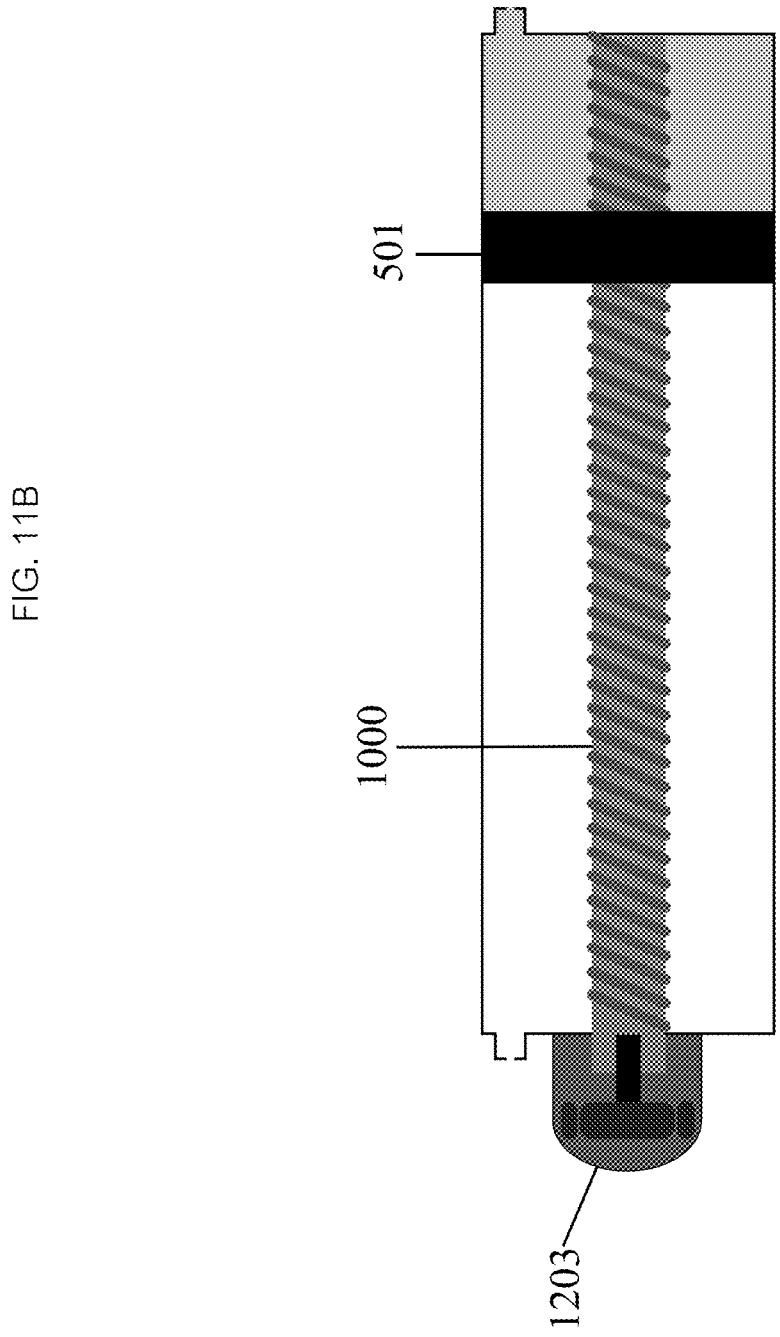

Referring now to FIG. 11, in some embodiments the active powered drive mechanism 600 may comprise an electric motor 1200. In some embodiments, the cable/pulley 900 (as seen in FIG. 11A) or lead screw drive mechanisms 1000 (as seen in FIG. 11B) may be connected, directly or through one or more gears 1201, to a small electric motor 1203, which may be powered by a battery or AC power. In some embodiments, appropriate electrical components and circuitry may include switches or dials to turn the device on/off, adjust flow, temperature, pressure, the volume to be infused, or other parameters may be included as needed.

Figure 12:
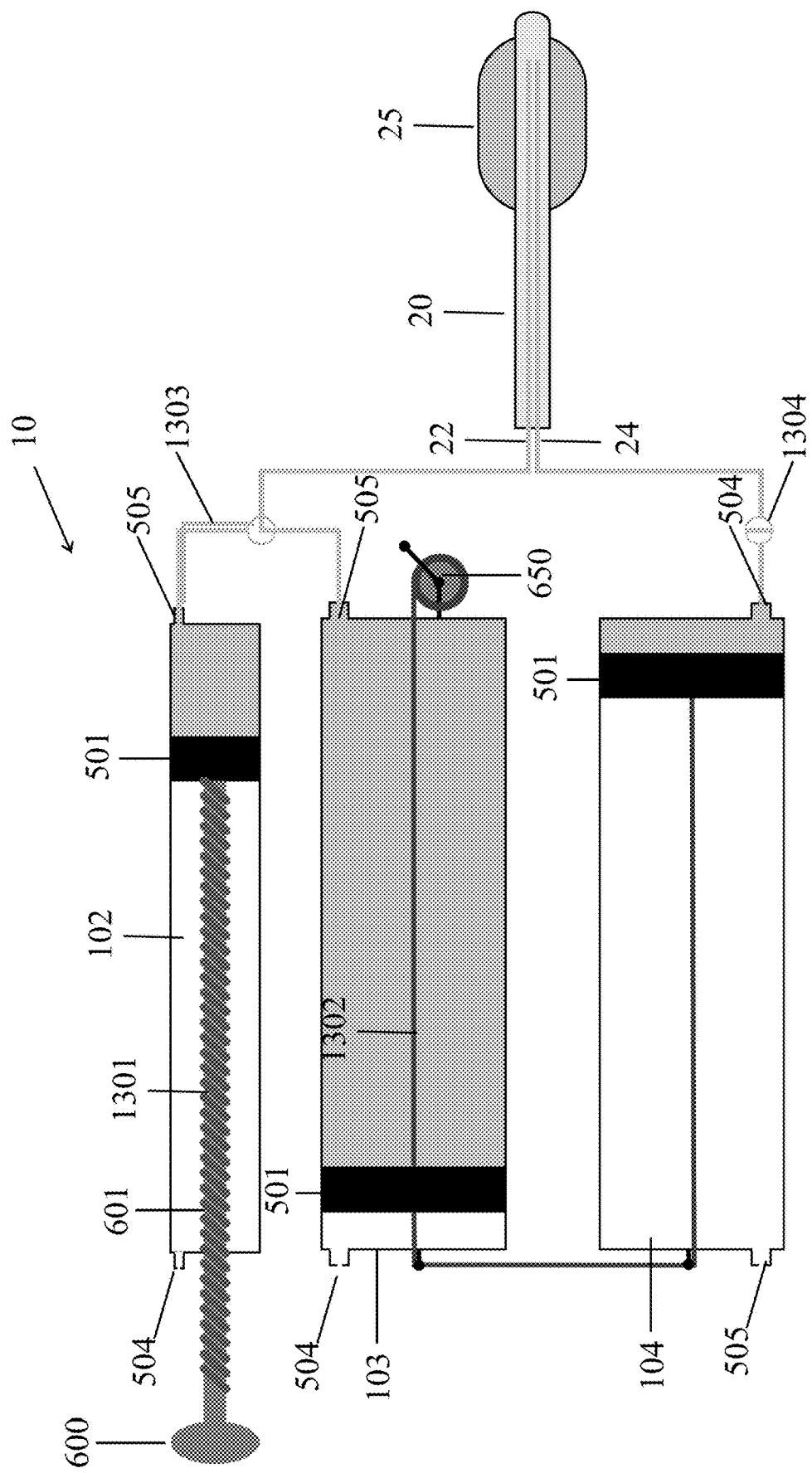
FIGS. 12, 13A-E, and 14 illustrate various embodiments of a continuous flow balloon catheter systems in accordance with the present disclosure.

In some embodiments, referring now to FIG. 12, the inflation 102, inflow 103 and outflow 104 chambers are distinct structures, each with its own piston 501, ports 504, 505 and valves (not pictured). The inflow chamber 103 comprises at least one outlet port 505 and the outflow chamber 104 comprises at least one inlet port 504. The inflow chamber 103 and outflow chamber 104 pistons 501 may be mechanically linked by a rigid rod 1301, cable 1302 or belt so that they move in opposite directions relative to their inlet/outlet port 504, 505, wherein the total volume in the two flow chambers 103, 104 may be constant and, as a result, the flow out of the outflow chamber 104 is the same as the flow back into the inflow chamber 103. These linked pistons 501 are controlled by a single inflow/outflow chamber drive mechanism. The inflation chamber 102 may have its own piston 501 and drive mechanism 600, which may be a manual mechanism. The drive mechanism 600 may be a rigid threaded plunger rod 601 with an analog or digital pressure gauge which functions just like a pressure syringe commonly used to inflate balloons in interventional procedures. In some embodiments, more complex manual and powered drive mechanisms may be used with the inflation chamber 102. In some embodiments, the inflation chamber 102 is activated once at the beginning of a procedure to inflate the balloon 25 to the desired volume and pressure, the inflation chamber 102 then remains in a fixed position during the infusion and is activated in the reverse direction once at the end of the procedure to deflate the balloon 25.

In some embodiments, the outlet ports 505 of the inflation chamber 102 and inflow chamber 103 can be connected to a three way inflow valve 1303 which in turn may be connected to the balloon catheter's inflow lumen 22 so it is in fluid communication with one or the other fluid chamber 103, 104. The inlet port 504 of the outflow chamber 104 can be connected to the outflow lumen 24 of the balloon catheter 20 through a separate outflow valve 1304. Once the connections between the infusion device 10 and balloon catheter 20 are complete, the inflation 102 and inflow chambers 103 can be filled with fluid, the outflow chamber 104 starts empty. The inflow valve 1303 may be positioned to establish fluid communication between the inflation chamber 102 and the balloon 25 through the catheter's 20 inflow lumen 22 while the outflow valve 1304 may be closed. In other words, in this initial state, neither flow chamber 103, 104 is in fluid communication with the balloon 25. The inflation chamber's 102 drive mechanism 600 is activated, inflating the balloon 25 to the desired volume and pressure. The inflow valve 1303 is then positioned to establish fluid communication between the inflow chamber 103 and the balloon 25 through the catheter's 20 inflow lumen 22. The outflow valve 1304 is then opened, establishing fluid communication between the outflow chamber 104 and the balloon 25 through the catheter's 20 outflow lumen 24. The infusion can be initiated by activating the inflow 103 and outflow 104 chamber drive mechanism 650 driving their pistons 501 in opposite directions, simultaneously driving fluid out of the inflow chamber 103 and drawing fluid back into the outflow chamber 104 at precisely the same rate, while maintaining balloon 25 volume and pressure. Once the infusion is completed, the outflow valve 1304 is turned off, the inflow valve 1303 is switched to the inflation chamber 102 and the inflation chamber's 102 drive mechanism 600 is activated in the reverse direction, drawing fluid into this chamber 102 from the balloon 25 causing it to deflate.

In another embodiment, the outlet port 505 of the inflation chamber 102 may connect directly to the distal end of the inflow chamber 103 while the outlet port 505 of the inflow chamber 103 may be connected to the inflow lumen 22 of the balloon catheter 20 through a simple inflow valve (not pictured). When the simple inflow valve is open, both the inflation 102 and inflow chambers 103 can be in fluid communication with the inflow lumen 22 of the balloon 25. The outflow valve 1304 is initially closed, allowing the drive mechanism 600 of the inflation chamber 102 to inflate the balloon 25 to the desired volume and pressure. Since the inflation 102 and inflow 103 chambers may be in fluid communication, the inflow chamber's 103 piston 501 must remain in a fixed position during this period so that the fluid from the inflation chamber 102 fills the balloon 25 and not the inflow chamber 103. Once the balloon 25 inflation is complete and the drive mechanism 600 of the inflation chamber 102 is deactivated, the outflow valve 1304 may be opened and the drive mechanism 650 of the inflow/outflow chambers 103, 104 can be activated to initiate the infusion. The inflation 102 and inflow 103 chambers remain in fluid communication, so the inflation chamber's 102 piston 501 must remain in a fixed position during this period so that the fluid from the inflow chamber 103 fills the balloon 25 and not the inflation chamber 103. When the infusion is complete, the outflow valve 1304 may be closed and the inflation chamber's 102 drive mechanism 600 can be activated in the reverse direction deflating the balloon.

Figure 13A:
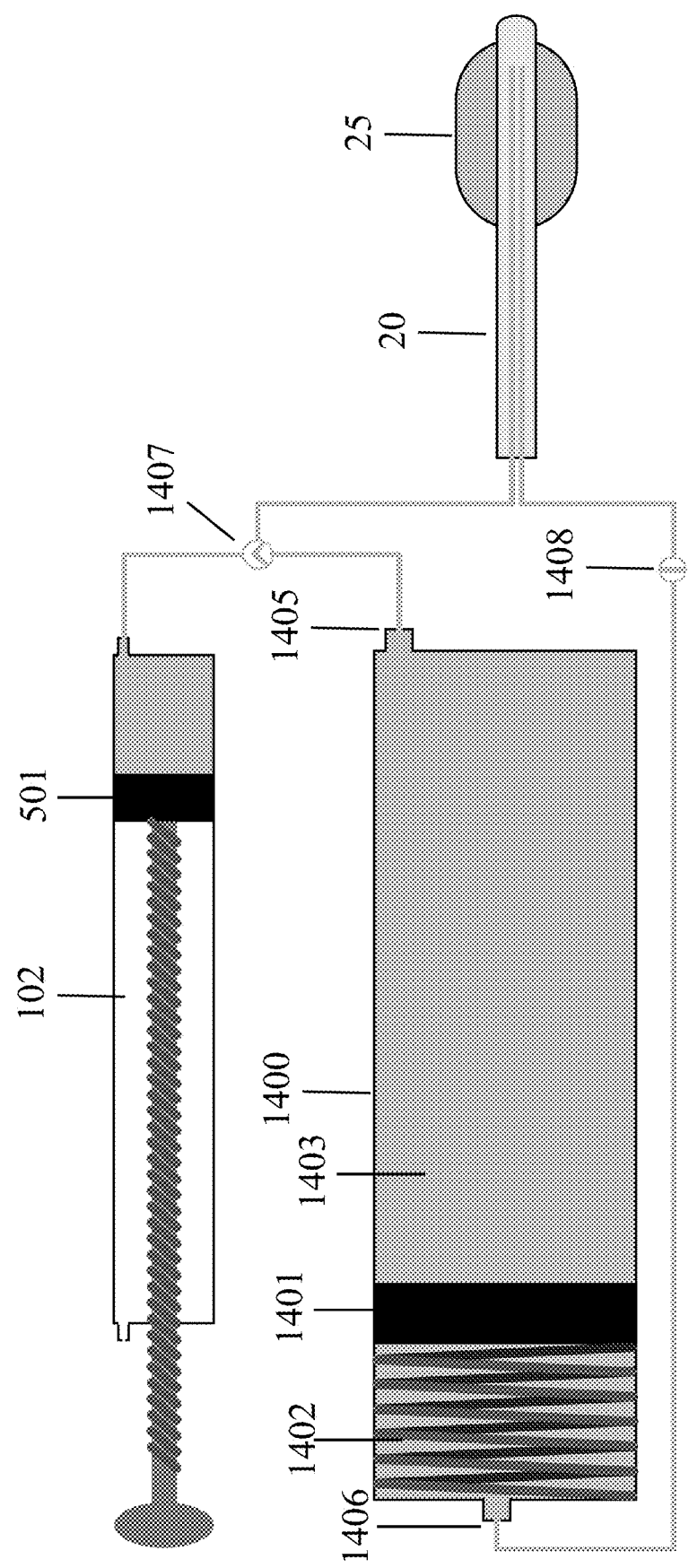
Figure 13B:
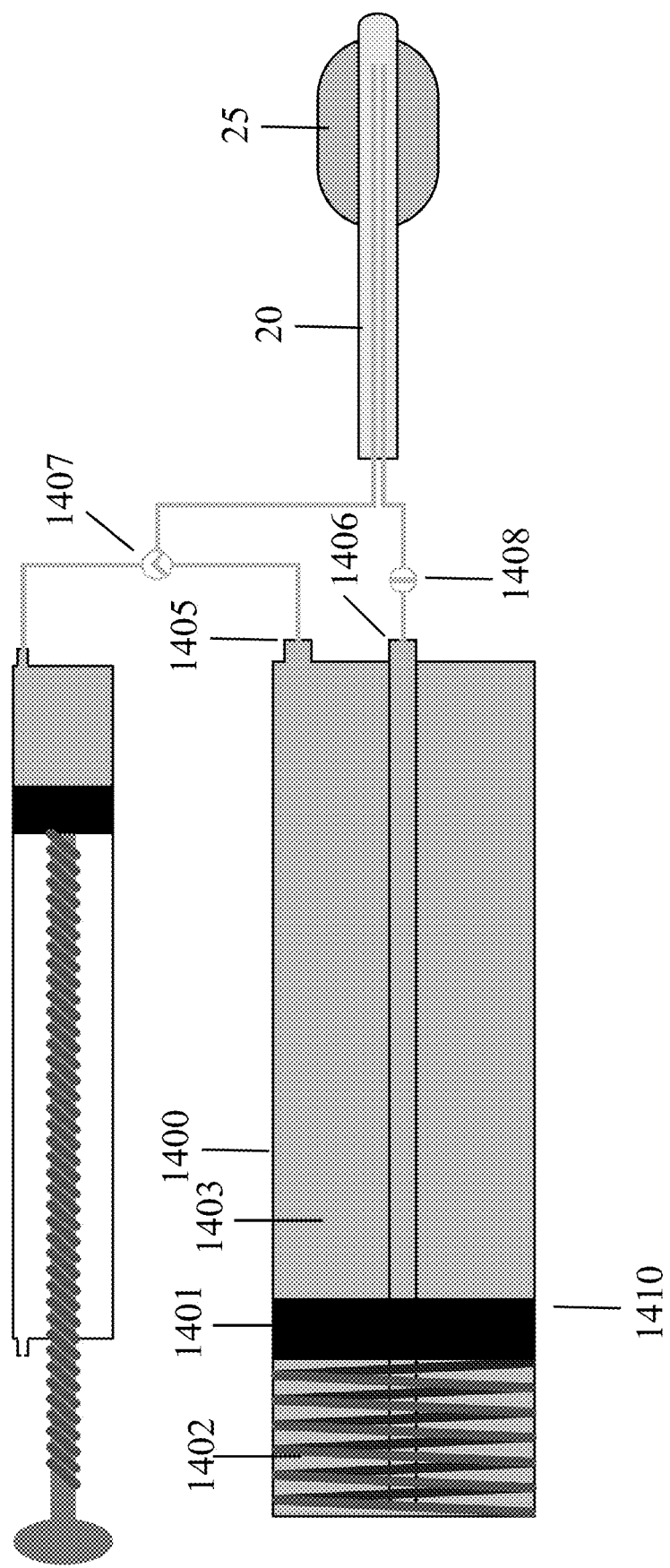
Figure 13C:
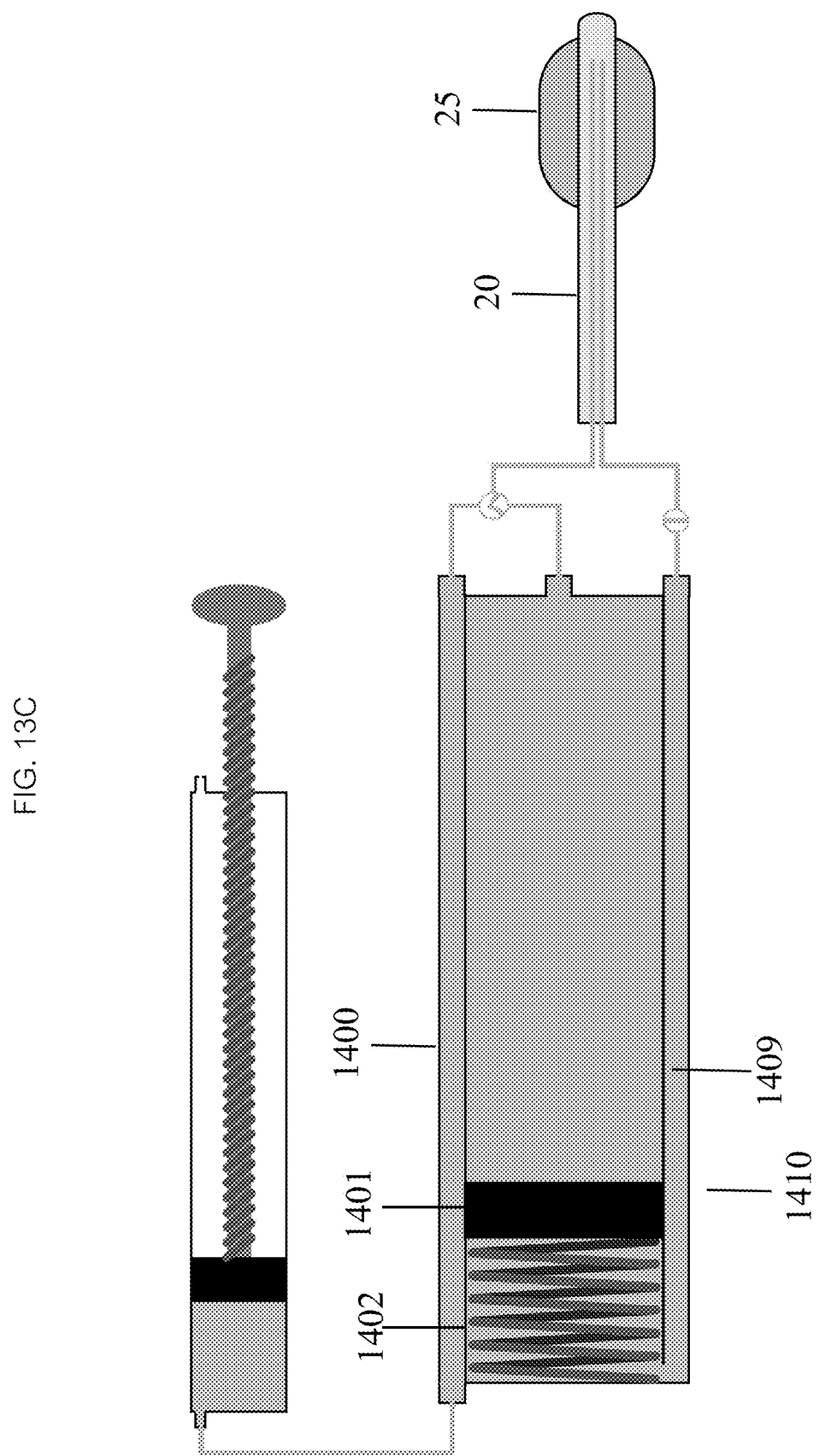
Figure 13D:
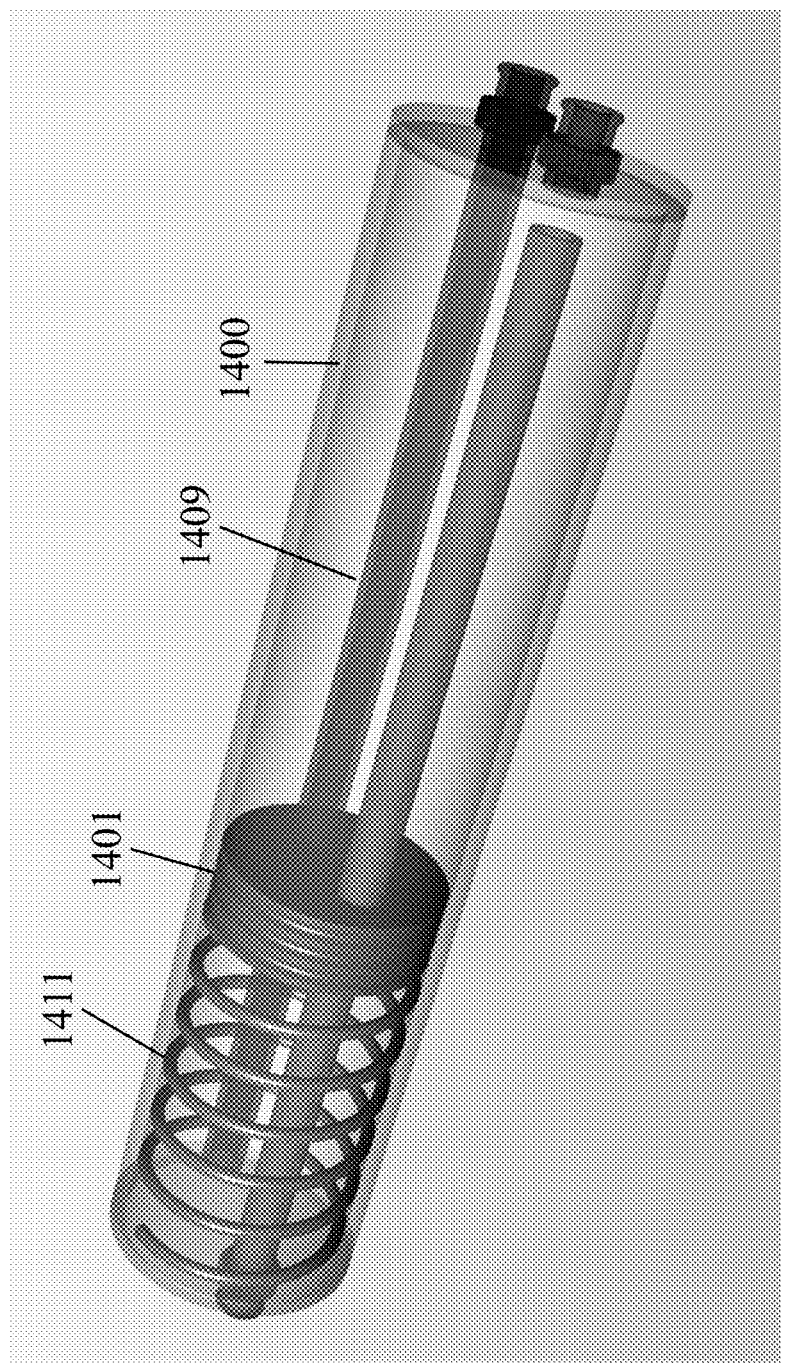
Figure 13E:
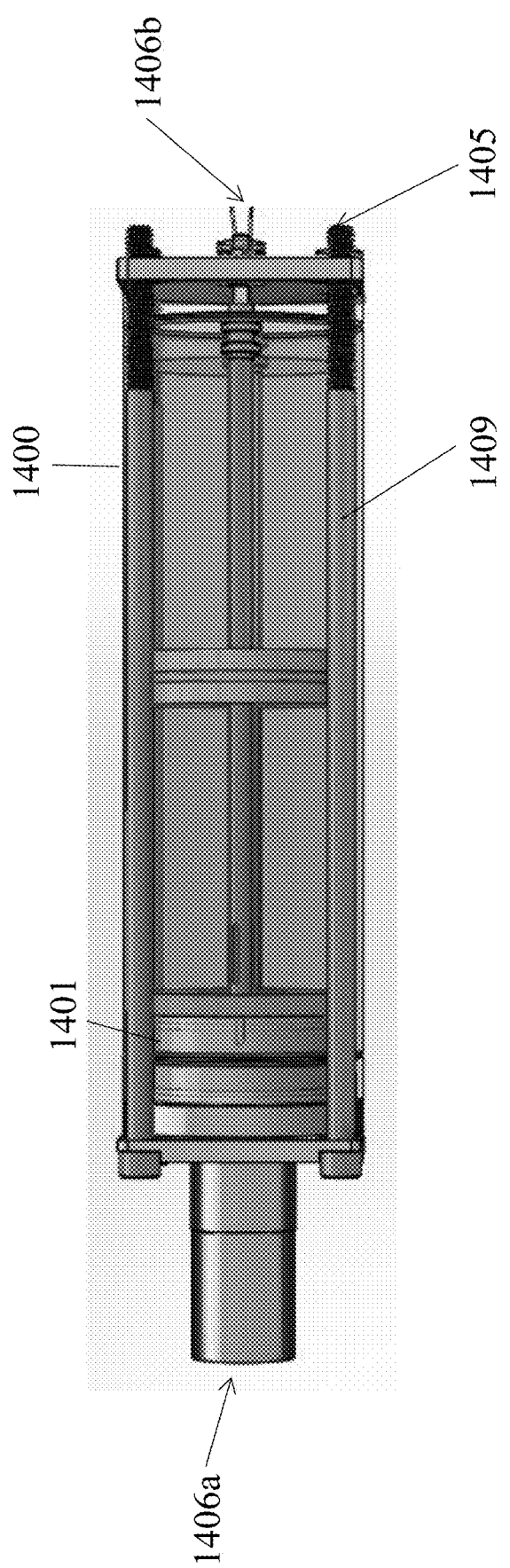

Now referencing FIG. 13A, in some embodiments, the inflation chamber 102 remains separate but the inflow and outflow chambers are combined into a single structure 1400 with a shared piston 1401. The piston 1401 partitions the combined chamber 1400 into inflow 1402 and outflow 1403 chambers. The outlet port 1405 of the inflow chamber 1403 and the inlet port 1406 (see also 1406a and 1406b in FIG. 13E) of the outflow chamber 1403 are located on opposite ends of the combined chamber 1400. Each port 1405, 1406 has its own valve 1407, 1408. In some embodiments, as seen in FIG. 13B both ports 1405, 1406 may be located on one end of the chamber 1400, with the outlet port 1406 communicating directly with the inflow chamber 1403 and the inlet port 1405 communicating with the outflow chamber 1402 through a central (as seen in FIG. 13D) or eccentric (as seen in FIG. 13C) outflow channel 1409 that passes through or adjacent to the piston 1401 and serves as a rail along which the piston 1401 rides. The channel 1409 may terminate close to the proximal end 1410 of the combined chamber 1400, communicating with the outflow chamber 1402 through an end hole. In some embodiments, the channel may extend all the way through the proximal end 1410 of the inflow chamber 1403, communicating with the outflow chamber 1402 through one or more side holes located near the proximal end 1410 of the inflow chamber 1403. As the piston 1401 moves, the volume in the inflow chamber 1403 decreases by precisely the same amount as the volume in the outflow chamber 1402 increases. The shared piston 1401 can be driven by any manual or powered drive mechanisms. Since both sides of the piston 1401 are in contact with a fluid filled chamber 1400, the mechanisms which feature external structures (e.g., rigid rod, cable/cord, lead screw) must have those structures exit the chamber through a gasketed port. A spring drive mechanism 1411 (as seen in FIG. 13D), in contrast, can be completely contained within the fluid filled chamber 1400.

Figure 14:
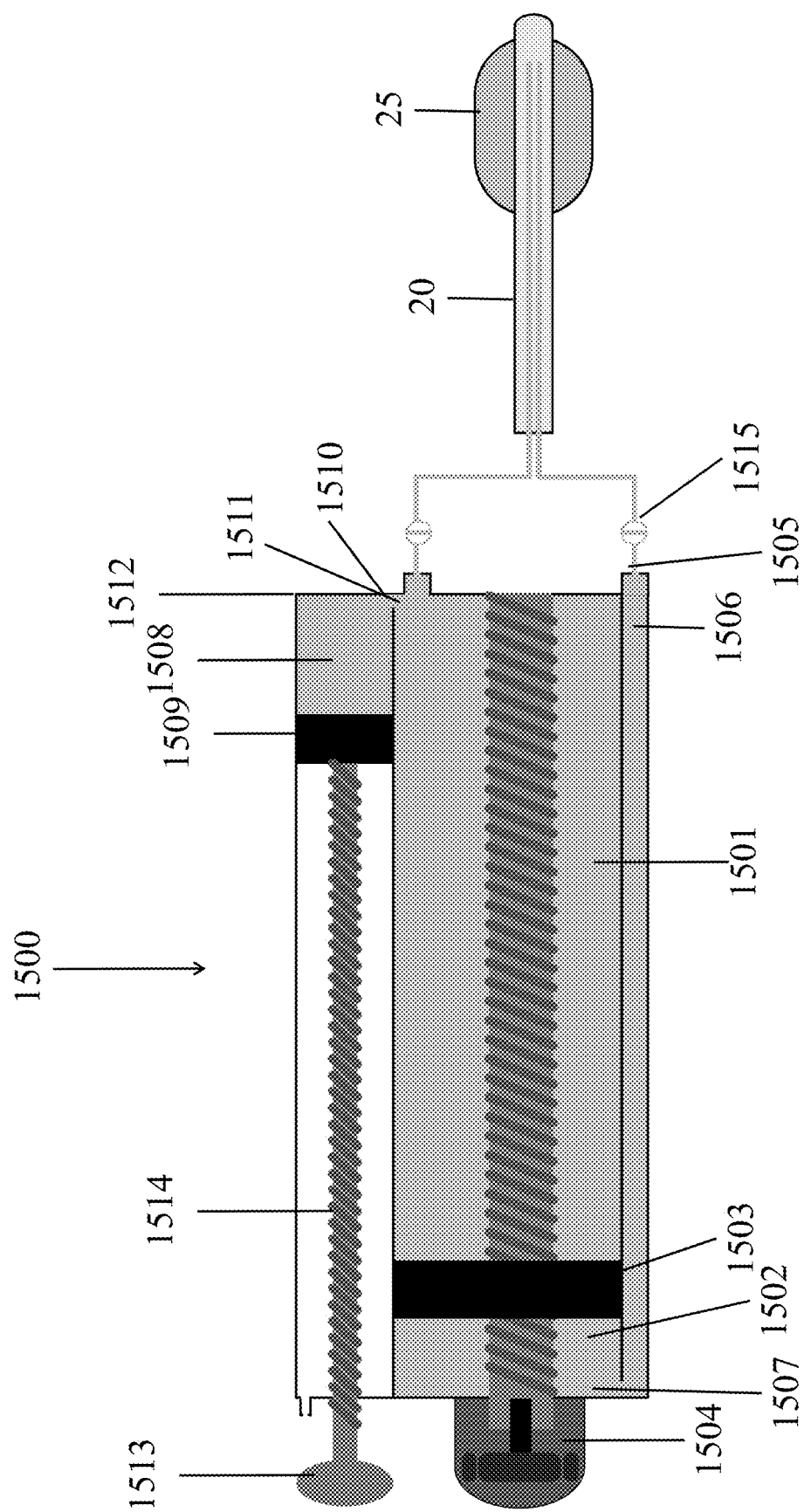

Now referencing FIG. 14, in some embodiments, all three chambers can be part of a single structure 1500. The inflow 1501 and outflow chambers 1502 share a common piston 1503 and drive mechanism 1504 while the outflow chamber 1502 communicates with its inlet port 1505 either directly or through a central or eccentric internal channel 1506 that passes through or adjacent to the piston 1503 and communicates with the outflow chamber 1502 through an end or side holes 1507. The inflation chamber 1508 can also be integrated into the structure 1500, as a central or eccentric channel with its own piston 1509. An inflation channel 1510 communicates with the inflow chamber 1501 near its distal end 1512, through an end hole or side holes 1511. The inflation chamber's 1508 drive mechanism 1513 may be a manual mechanism, such as a threaded rigid rod 1514 that functions like the plunger of a pressure regulated syringe. The inflation chamber 1508 drive mechanism 1513 can be activated, inflating the balloon 25 to the desired pressure and volume. The outflow chamber 1502 inlet valve 1515 may be opened and inflow chamber 1501 drive mechanism 1504 is activated, initiating the infusion. The outflow chamber 1502 inlet valve 1515 can be closed and the inflation chamber 1508 drive mechanism 1513 can be reversed, deflating the balloon 25.

Figure 15A:
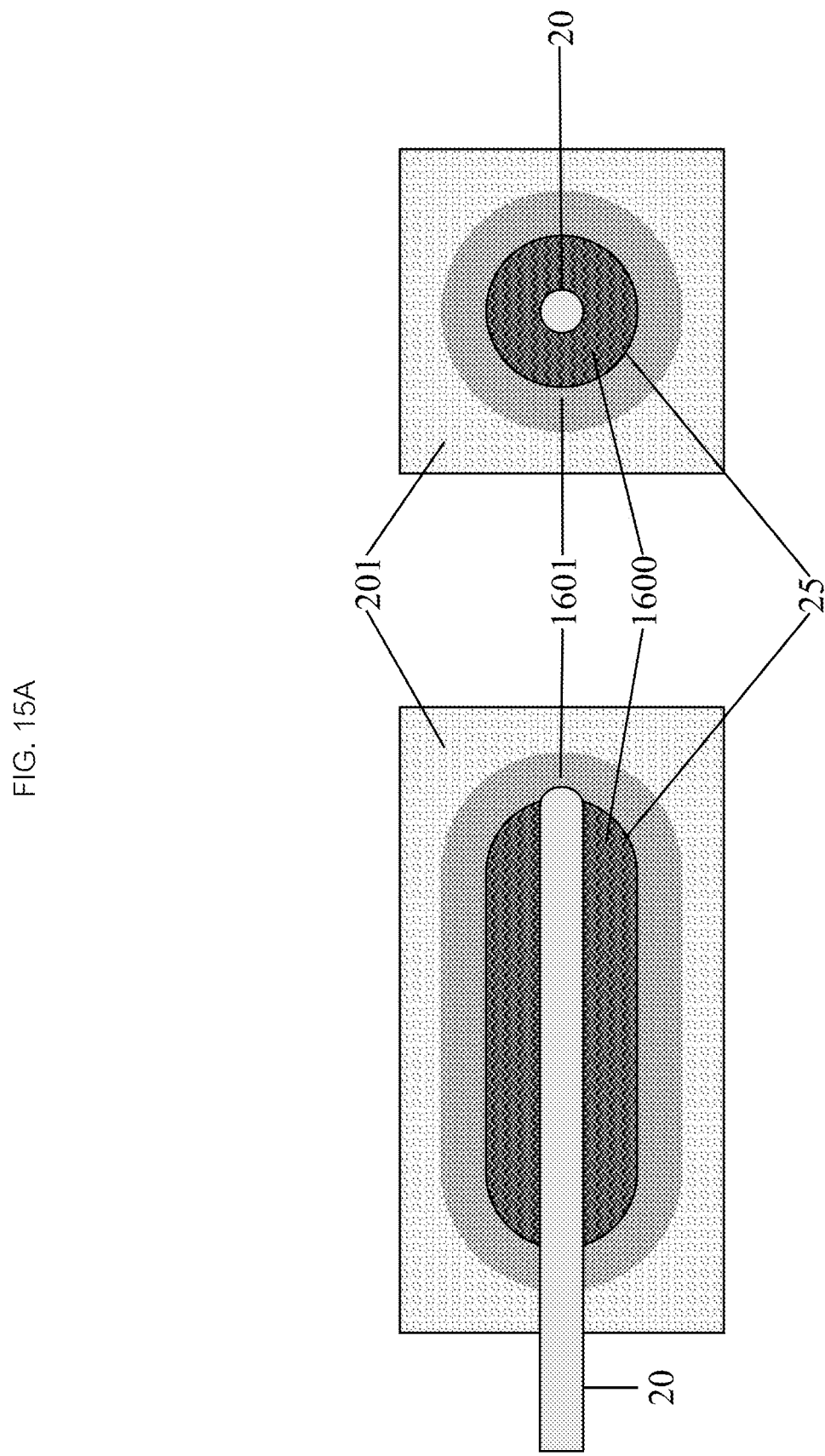
FIGS. 15A-C illustrate the placement of embodiments of a balloon relative to a target tissue, in accordance with various embodiments of the present disclosure.
Figure 15B:
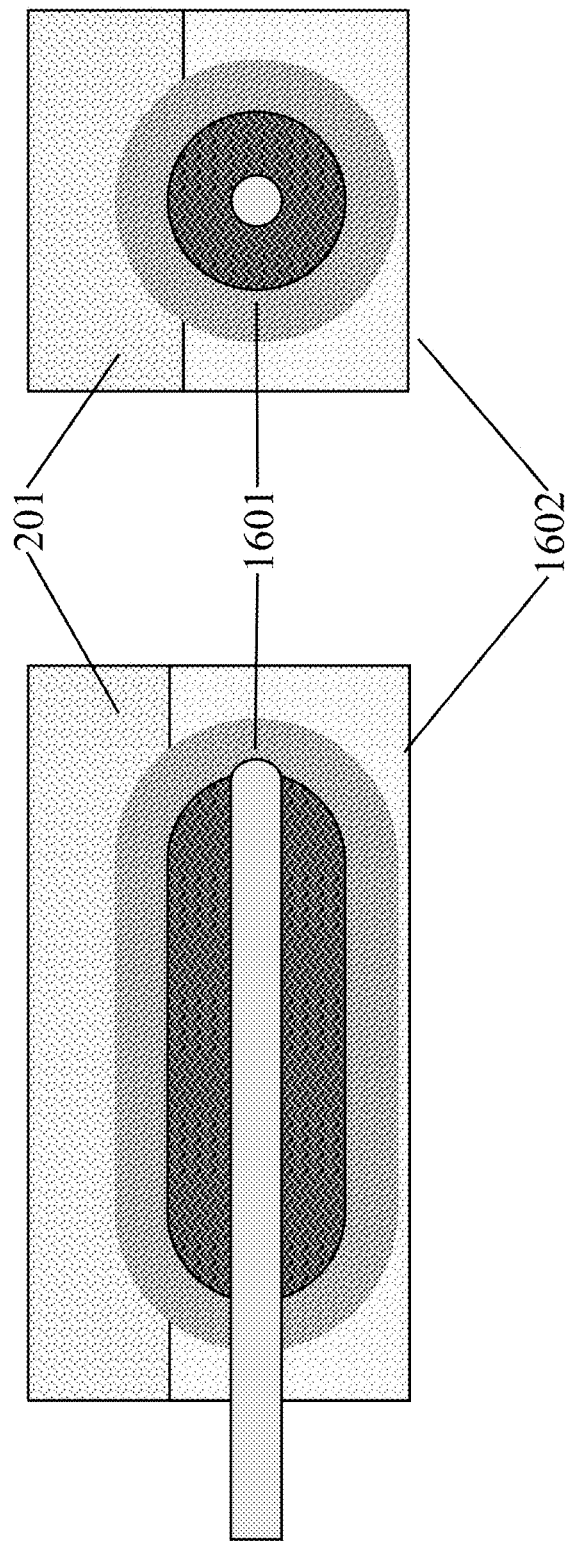
Figure 15C:
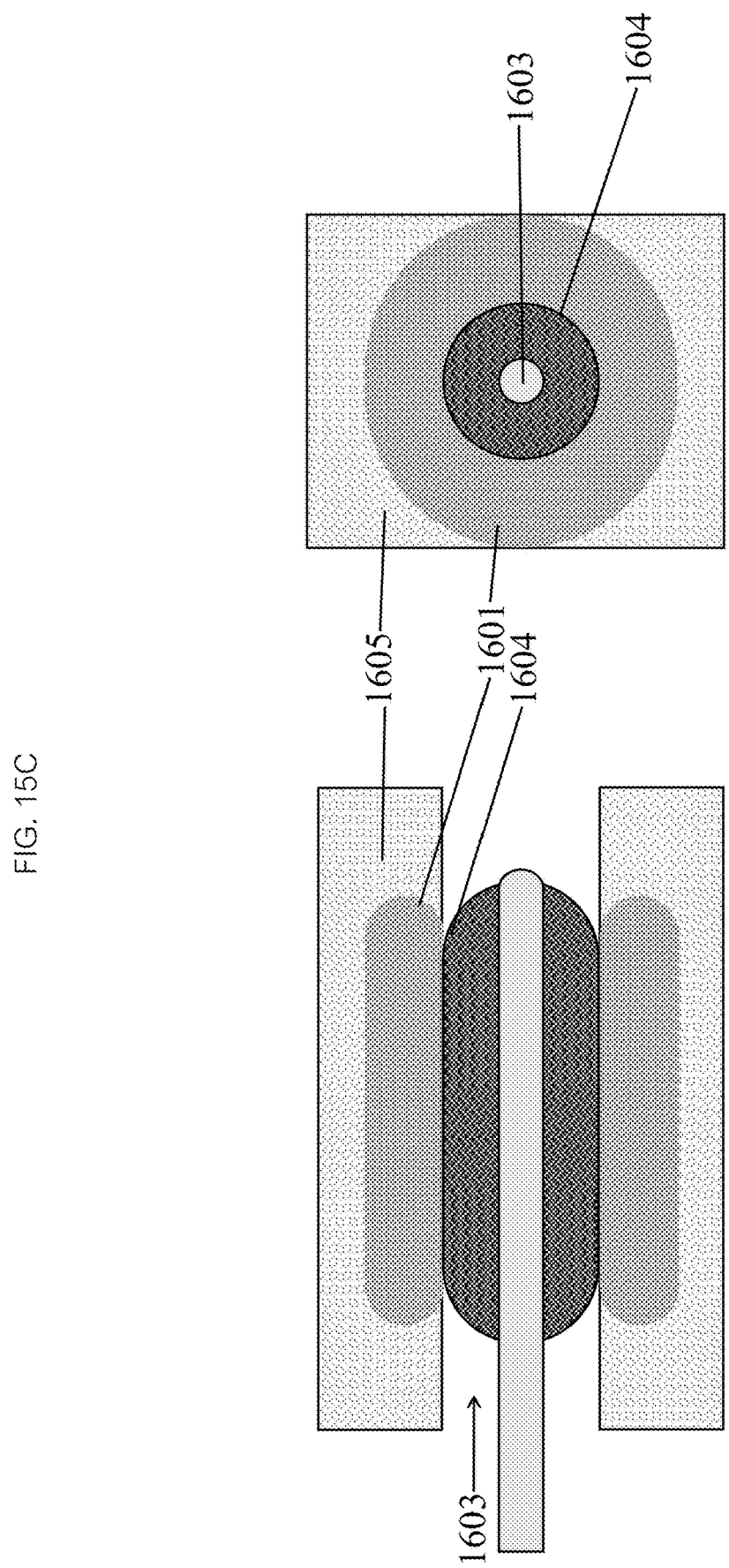

Referring now to FIG. 15A, in some embodiments a standard elliptical or spherical balloon 25 can uniformly transfer heat from the heated liquid 1600 in the balloon 25 to the surrounding tissue. In some embodiments, as seen in FIG. 15B, the target tissue 201 may be relatively symmetric and the balloon 25 can be inserted into the middle of the tissue 201. The balloon 25 may also be inserted adjacent to the target tissue 201 through other normal tissue 1602, whereby some normal tissue 1602 is ablated along with the target tissue 201 leading to an ablated tissue lesion 1601. In some embodiments, as seen in FIG. 15C, the balloon 25 may be inserted through the lumen 1603 of a hollow structure such as a blood vessel, airway, bone or gastrointestinal tract. In this case, the inflated balloon 25 makes contact with the inner wall of the lumen 1603, ablating through the wall 1604 of the structure and surrounding tissues 1605 in a uniform fashion.

Figure 16:
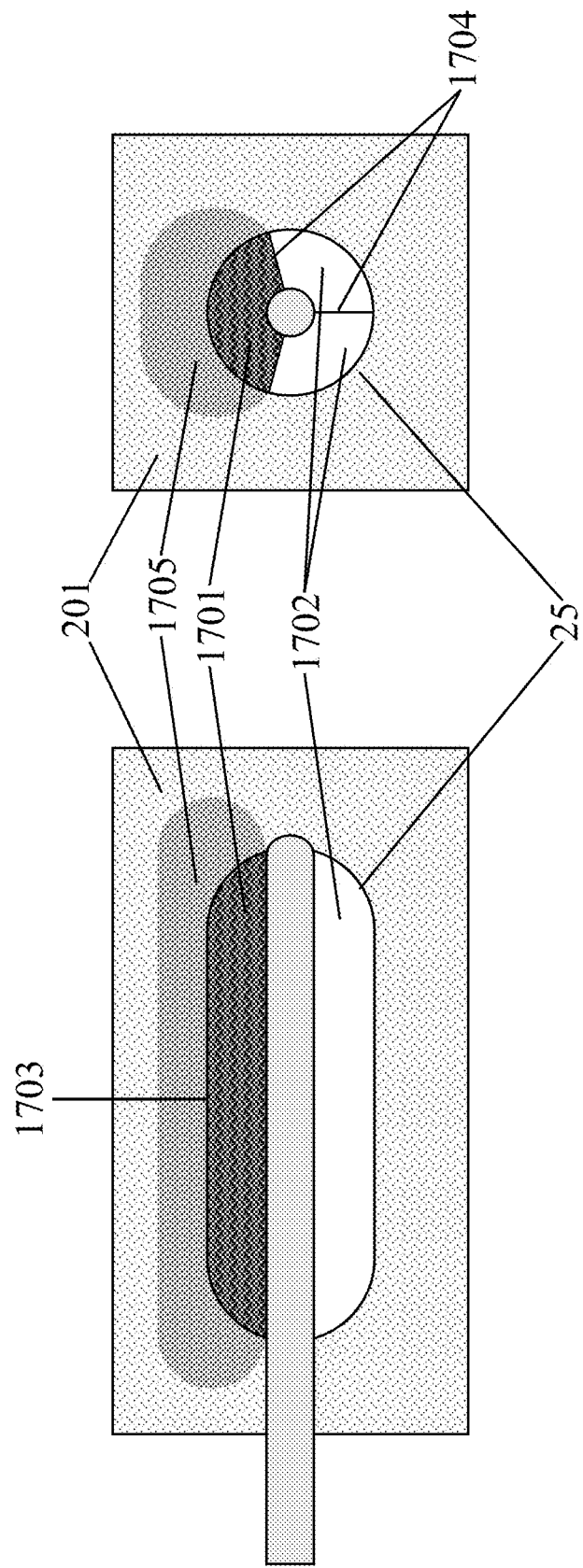
FIGS. 16, 17A-B illustrate various balloon designs in accordance with various embodiments of the present disclosure.

Now referencing FIG. 16, in some embodiments the local anatomy in the vicinity of the target tissue will be much more complex. A center of the target tissue 201 may not be directly accessible and the balloon 25 will be positioned adjacent to it through other tissue or a hollow structure. There may also be nearby critical structures that need to be protected from thermal damage. The balloon 25 may have a more complex structure to add directionality to the flow of heat towards the target tissue 201 but not to other tissues or structures. Specifically, when the balloon 25 is fully inflated, the heated liquid may be contained in a heated liquid compartment 1701, which may be limited to certain portions of the balloon 25 that are separated from the others which serve as insulators 1702. Such a structure may be used to create a pattern of "hot spots" 1703 and "cold spots" on the surface of the balloon resulting in a specific ablation pattern 1705.

In some embodiments, the heated compartment 1701 and an insulating substance may be configured such that the heat flows preferentially from the heated liquids into the target tissue 201 and not through the insulating portions 1702 of the balloon 25. Specifically, the volumetric heat capacity, specific heat capacity (Cv), and thermal conductivity of the insulating material must be significantly lower than that of the liquid to be heated and the surrounding tissues. Since the water content of most tissues are very high, their thermodynamic properties are similar to water. The insulating material could, for example, be a solid with low heat capacity and thermal conductivity such as a compressible foam. In some embodiments, gases may be used as insulators. The volumetric heat capacity of most commonly used gases is approximately 0.001 J m−3 K−1 compared to 4.2 J m−3 K−1 and 3.7 J m−3 K−1 for water and tissues respectively. The thermal conductivity of most commonly used gases is approximately 0.02 W m−1 K−1 compared to approximately 0.5 W m−1 K−1 for water and most tissues. Because Cv and thermal conductivity are orders of magnitude higher for the liquid in the balloon 25 and the surrounding tissues than the gas in the insulating portions 1702, the liquid will efficiently transfer its heat through the hot spots to the tissue without significantly heating the gas in the insulating portions allowing the latter to keep the tissues adjacent to them cool until the ablation is complete.

In some embodiments, the balloon has internal septae 1704 which divide the balloon 25 into separate compartments. Heated liquid can be infused into (and recycled through) the heated compartments 1701. In some embodiments, a gas (air, carbon dioxide, oxygen or any biocompatible gas) may be used to inflate the insulating compartments 1702. The balloon 25 surface overlying heated compartments 1701 serve as "hot spots" 1703, allowing heat to transfer to and ablate its adjacent tissue. The balloon 25 surface overlying insulated compartments 1702 serve as "cold spots", preventing heat from transferring to its adjacent tissue, protecting it from ablation.

Figure 17A:
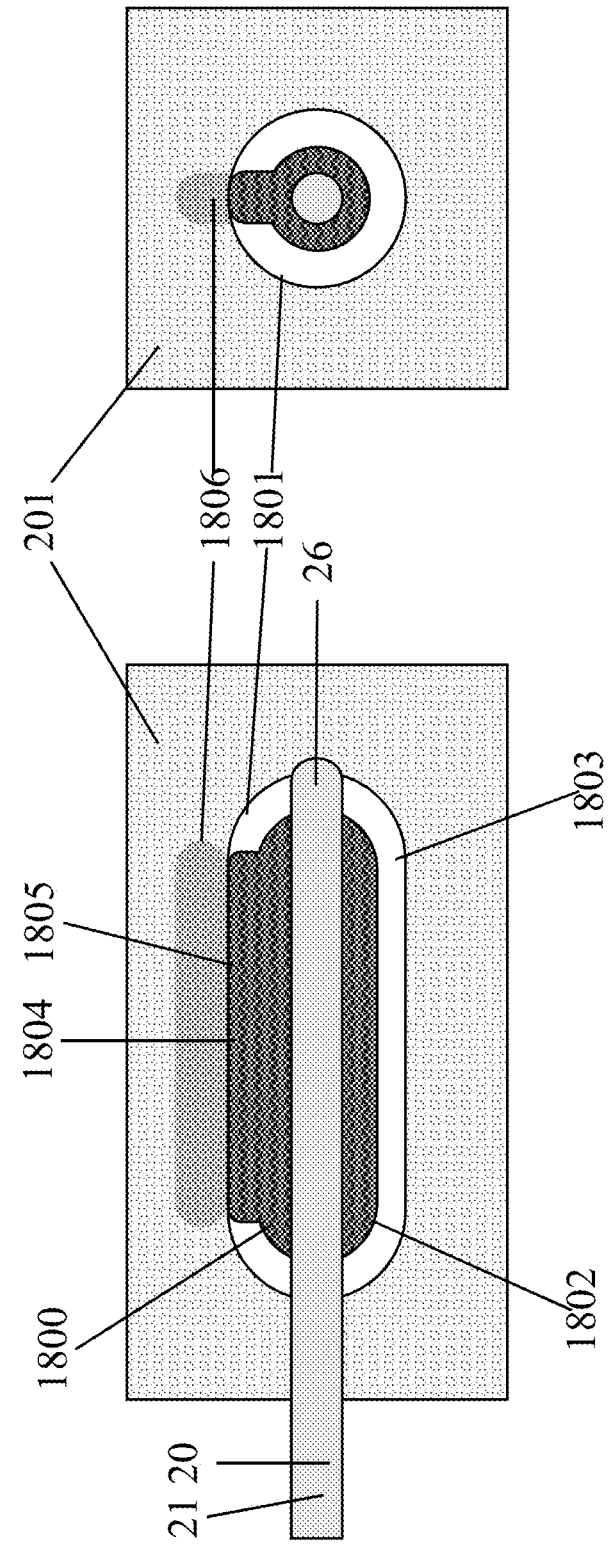
Figure 17B:
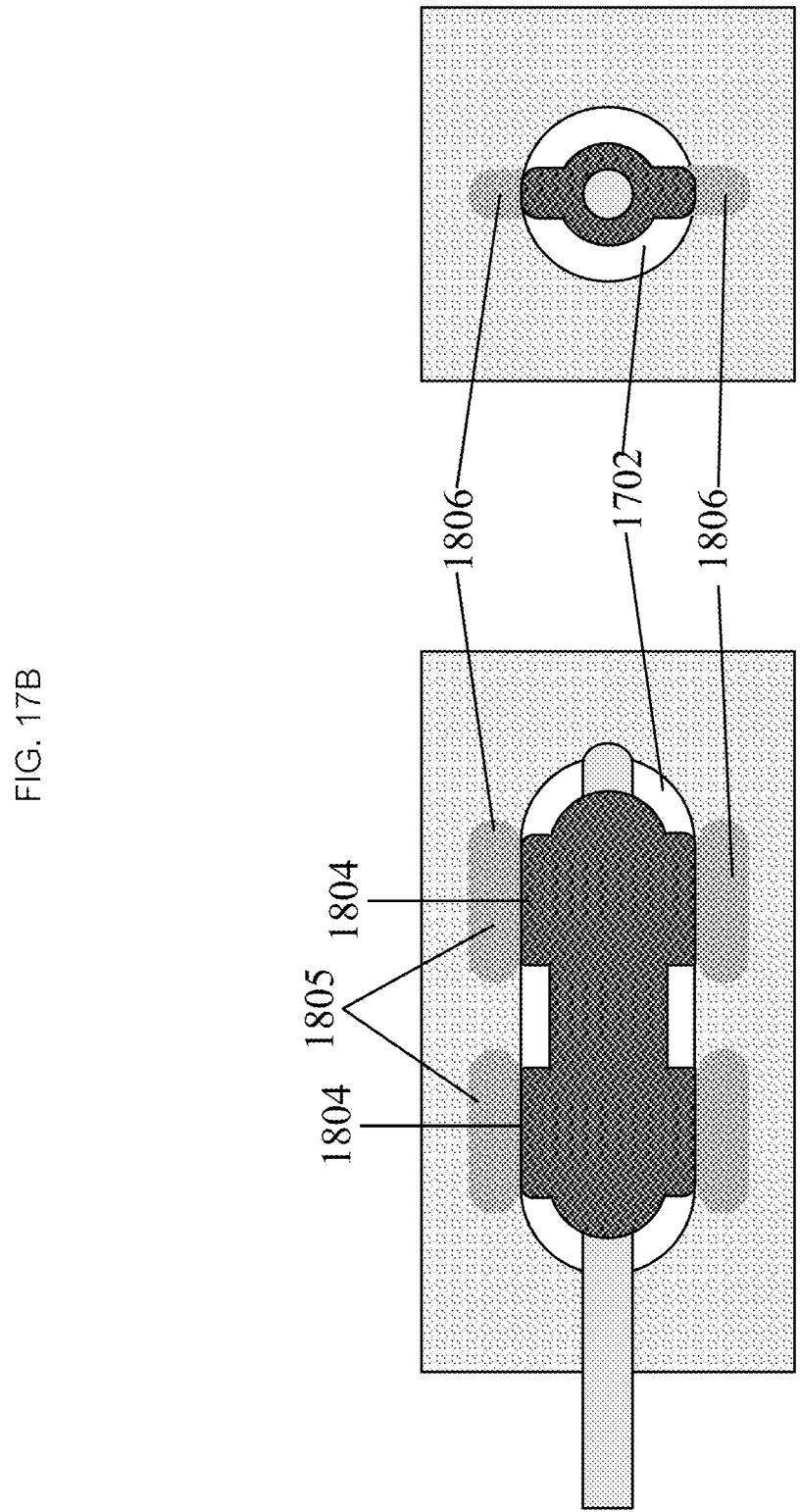
Figure 18A:
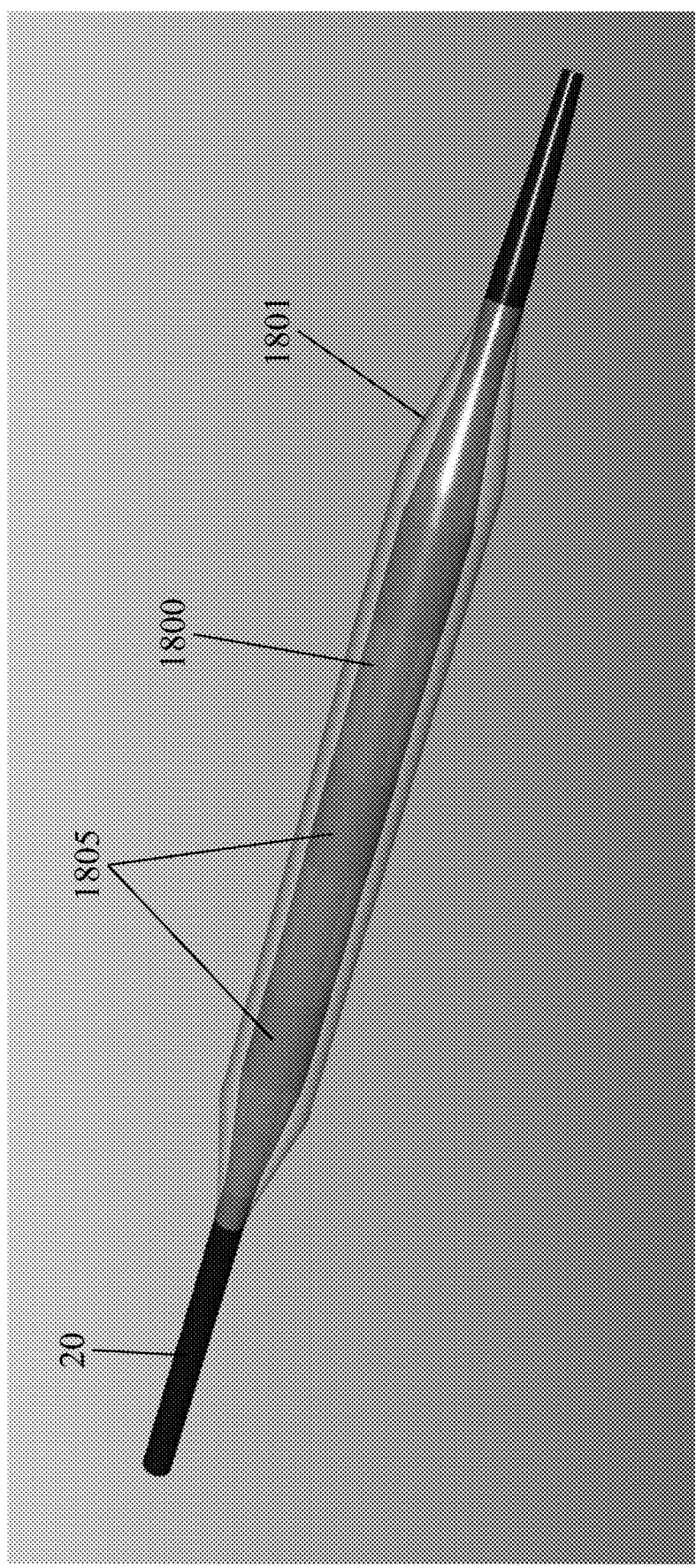
FIGS. 18A-D illustrate various "hot spot" designs for use in connection with an embodiment of a double balloon catheter in accordance with the present disclosure.
Figure 18B:
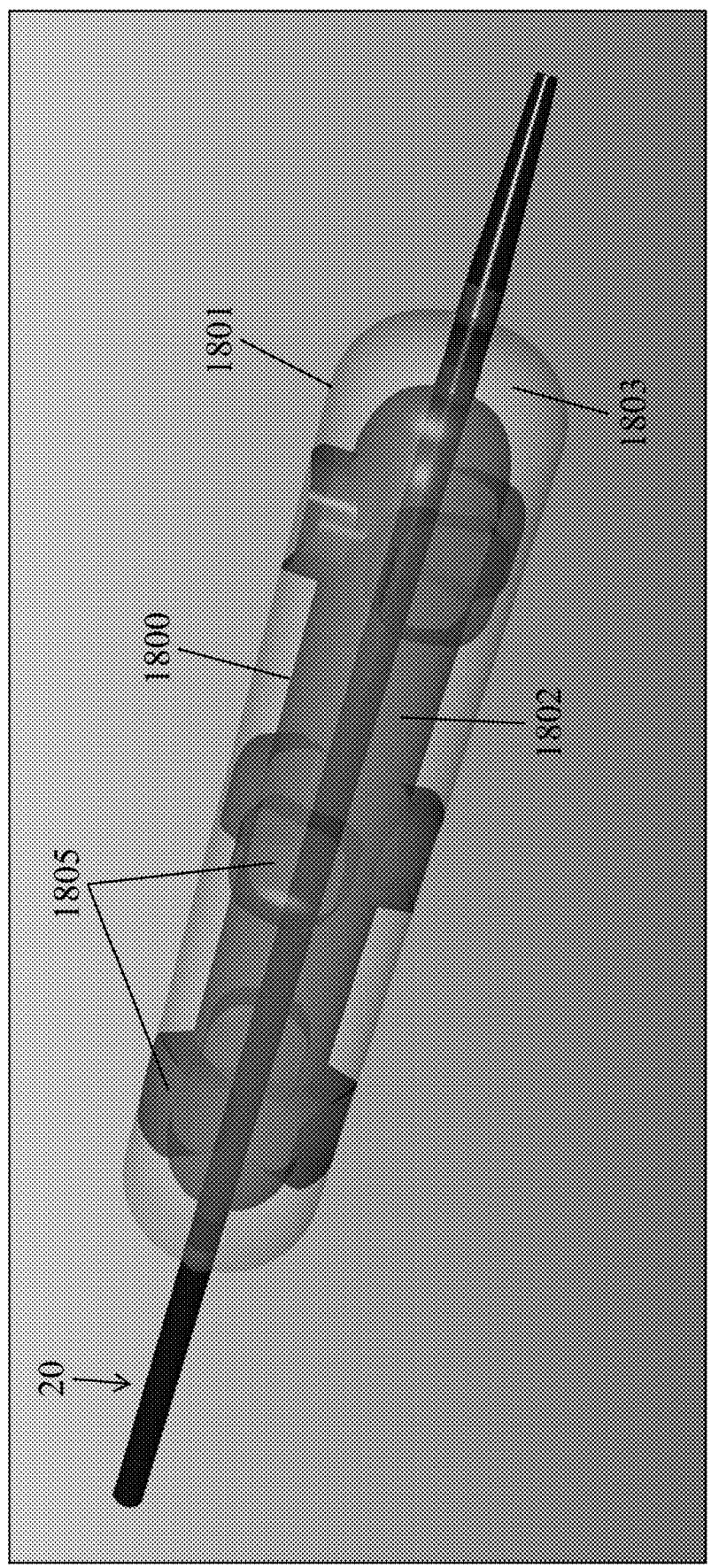
Figure 18C:
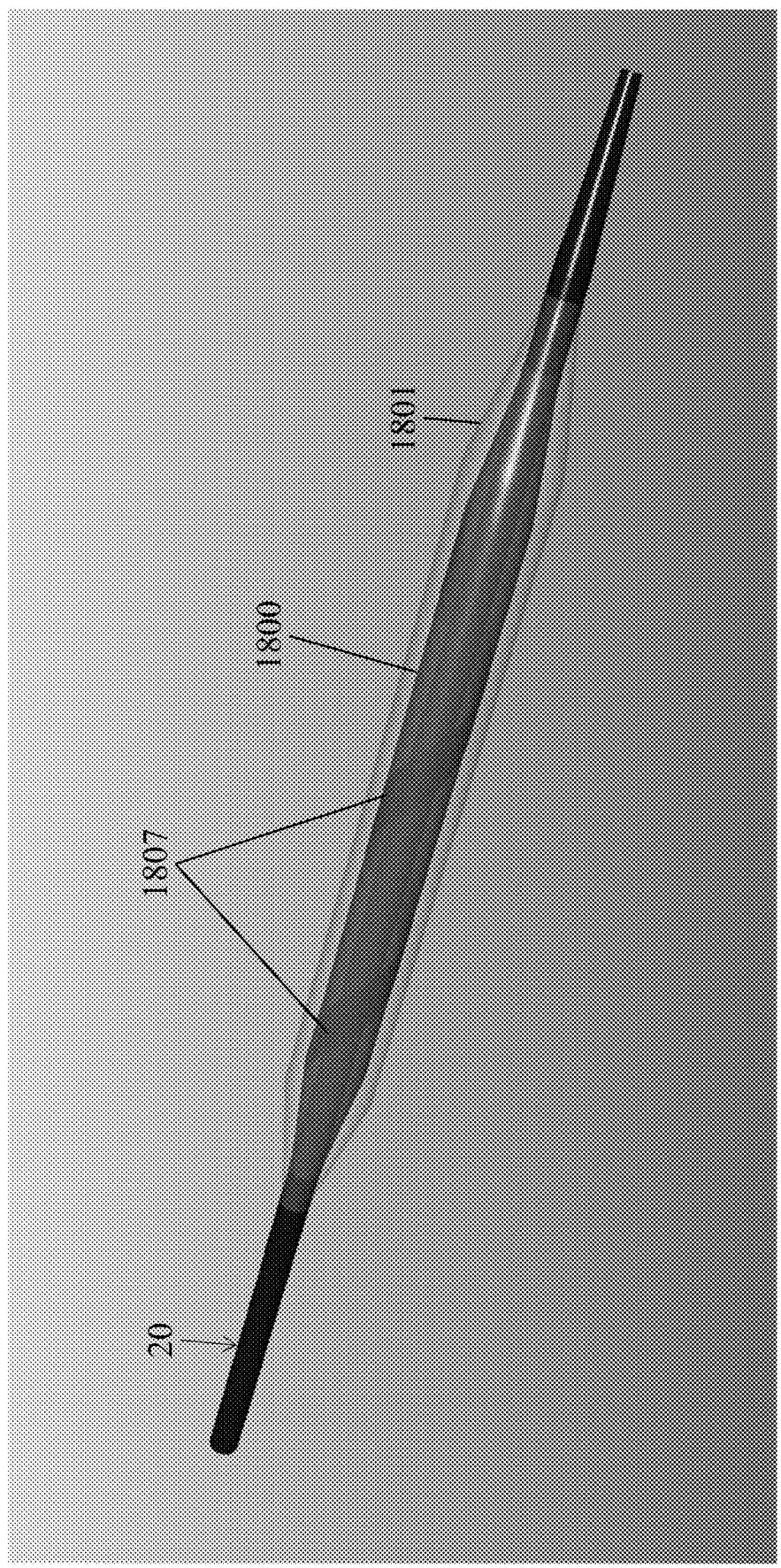
Figure 18D:
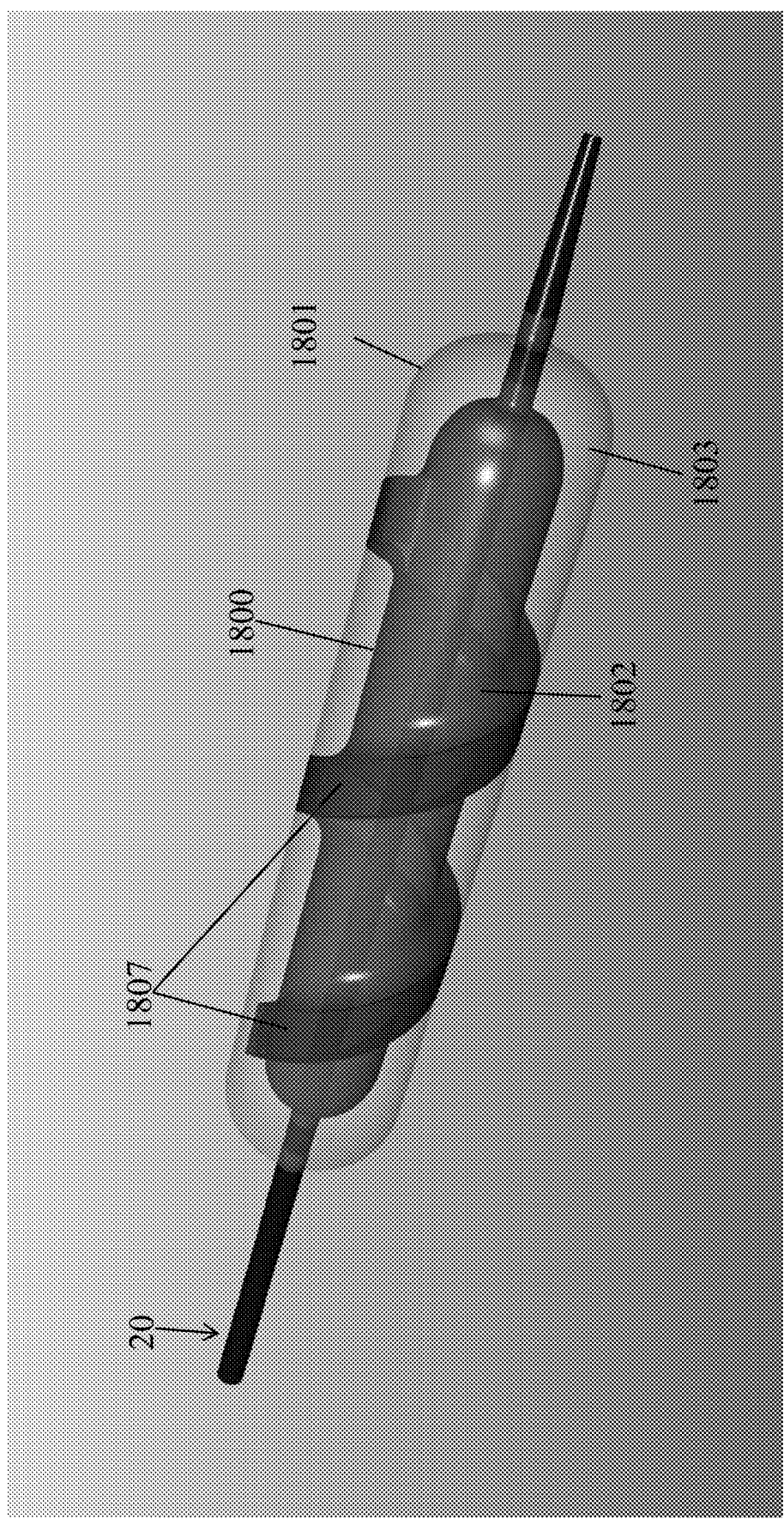

In reference to FIGS. 17A, 18A, and 18C in some embodiments, two concentric balloons 1800, 1801 with separate lumens are attached to the distal end 26 of the catheter 20. Referencing FIGS. 17A, 18B and 17B, the inner balloon 1800 when inflated has a smaller baseline radius than the outer balloon 1801. The inner balloon 1800 may have one or more areas along its length where it protrudes radially to make contact with the inner wall of the outer balloon 1801 yielding one or more areas of contact 1804. The areas of contact 1804 may be incidental to any relative geometries of the two balloons 1800, 1801, or the areas of contact 1804 can be forced by bonding or fusing the balloons 1800, 1801. The inner balloon 1800 may be inflated with a circulating heated liquid 1802 and the outer balloon may be inflated with a gas 1803. The areas of contact 1804 between the inner 1800 and outer 1801 balloons become hot spots 1805 (as seen in FIG. 18B) or strips 1807 (as seen in FIG. 18C and FIG. 18D) which ablate the tissue 201 in matching patterns 1806. The rest of the outer balloon 1801 remains cool because the gas 1803 within the outer balloon 1801 insulates the tissue 201 from the hot inner balloon 1800 in much the way a thermos insulates its content from the atmosphere.

In some embodiments, insulating compartments 1702 may be filled with an appropriate amount of gas 1803 prior to use of the device. The insulating compartments 1702 may be pre-filled with gas 1803 during manufacture and sealed so that only the heated liquid compartments are inflated during the procedure. In some embodiments, in order to maneuver the balloon catheter 20 within the patient, the distal tip may be enclosed in a sheath or other delivery mechanism, compressing the pre-filled gas compartments so that a cross sectional profile is acceptable. Once the catheter 20 is in position, the distal tip is unsheathed, allowing the gas compartments to expand to their neutral volume. After the ablation is completed and the heated liquid compartments are deflated, the distal tip must be re-sheathed and the gas compartments recompressed to decrease the cross sectional profile prior to repositioning or withdrawing the balloon catheter 20.

Figure 19:
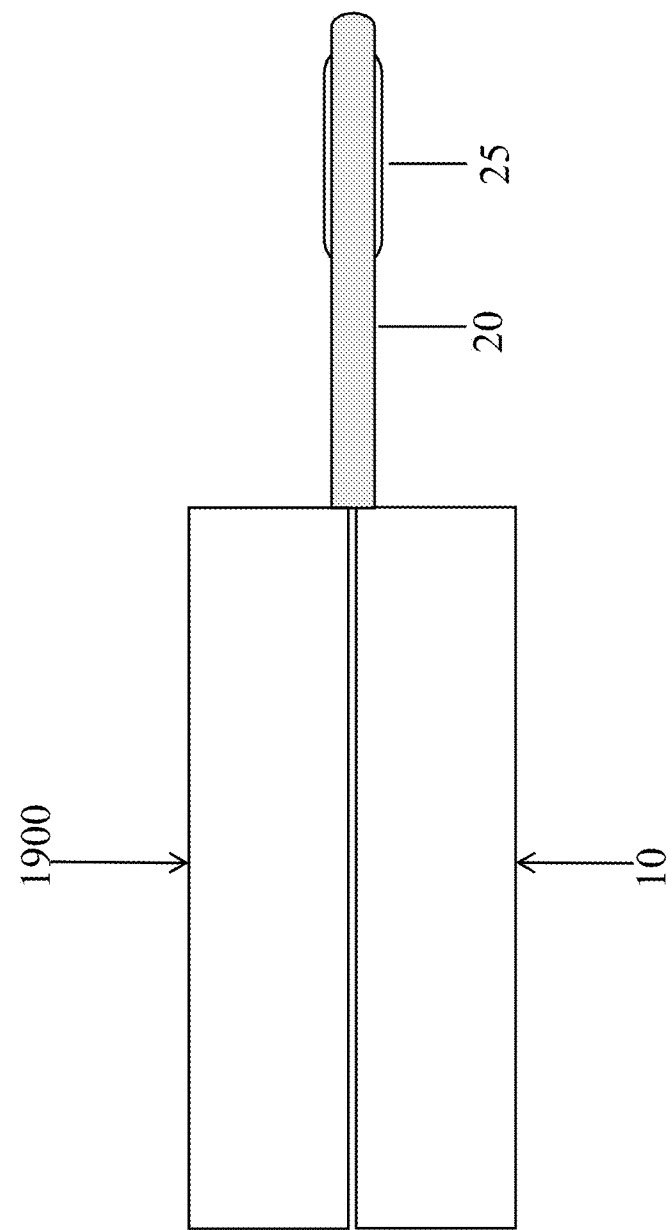
FIG. 19 illustrates components of a thermal ablation system in accordance with an embodiment of the present disclosure.

Now referring to FIG. 19, in some embodiments both the insulating compartments and the heated liquid compartments of the balloon 25 are initially empty and communicate with their respective gas and heated liquid inflation lumens. A gas inflation device 1900 is provided which delivers a volume of the appropriate gas (e.g., air, carbon dioxide, oxygen) through a gas inflation lumen into the insulating gas compartments so that they reach the appropriate volume or pressure. The device 1900 also allows the insulating gas compartments to be deflated after the ablation is completed prior to withdrawing or repositioning the catheter 20. The gas inflation device 1900 may be a syringe, with or without a pressure indicator or regulator. Other embodiments of the gas inflation device 1900 may utilize a cartridge filled with an appropriate gas (e.g., carbon dioxide) or a medical gas line available in an operating or procedure room (e.g., oxygen). The gas inflation device 1900 may be integrated with the infusion device 10. The insulating gas compartments may contain an effervescent powder such as calcium carbonate. The compartments may then be inflated by infusing a small volume of water into the compartments which reacts with the powder and releases a volume of gas, thereby inflating the compartments.

Figure 21A:
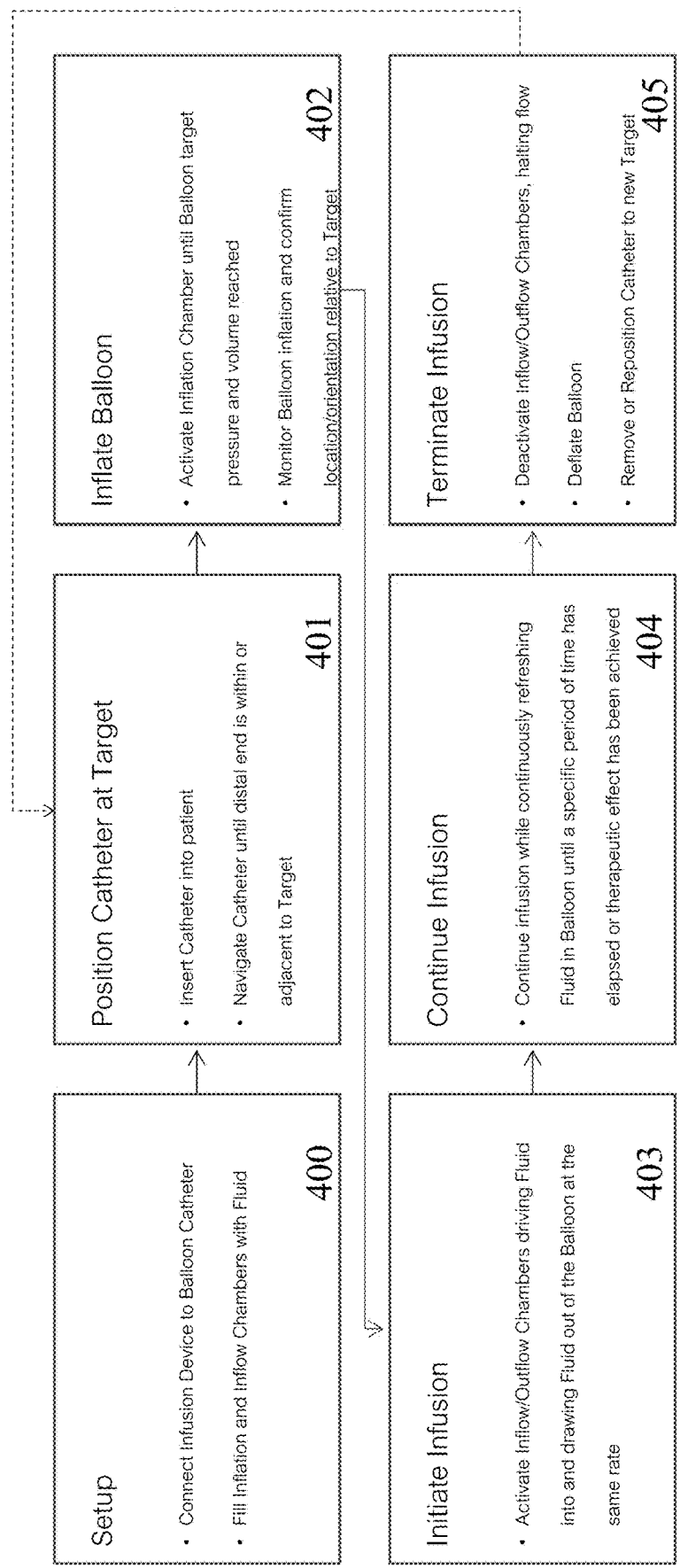
FIGS. 21A-H illustrate a method of operating an embodiment of a balloon catheter system in accordance with of the present disclosure.
Figure 21B:
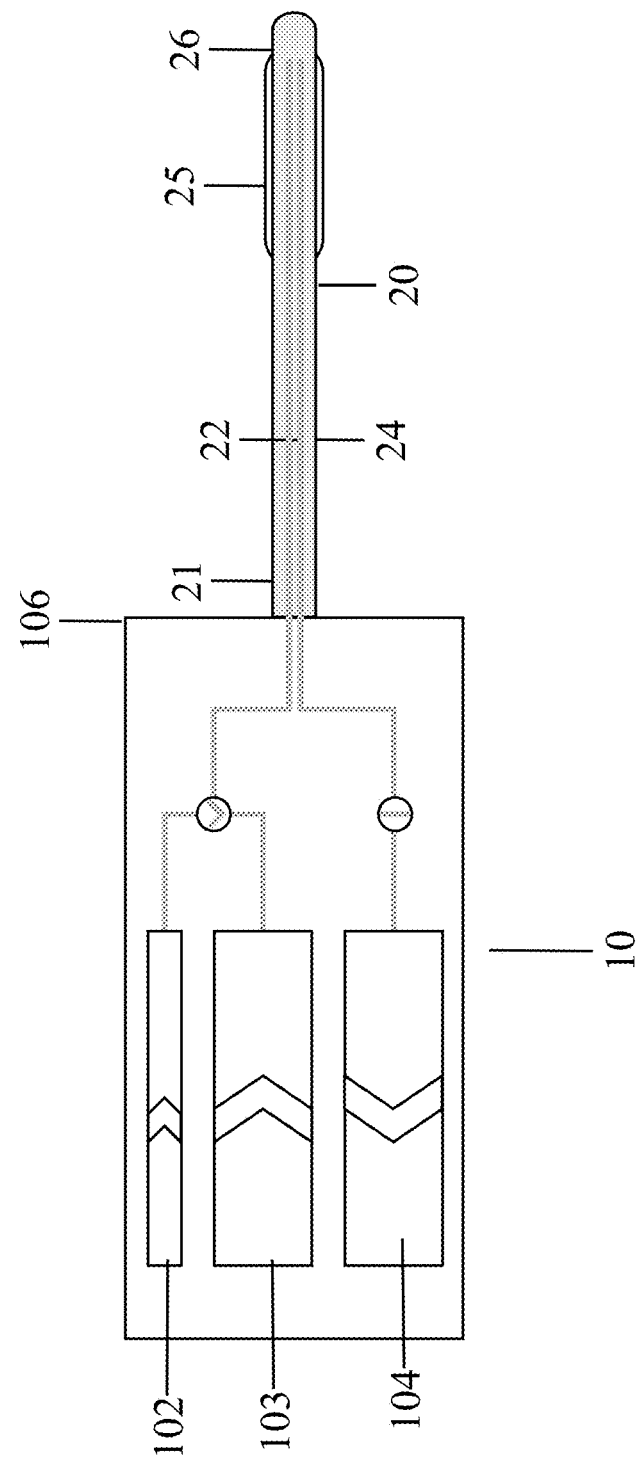

An embodiment of a method of operating a system in accordance with the present disclosure, as depicted in FIG. 21A, comprises: setting up the system 400, positioning a catheter 401, inflating a balloon 402, initiating an infusion 403, continuing the infusion 404, and terminating the infusion 405. In some embodiments, referencing FIG. 21B, setting up 400 comprises connecting a distal end 106 of an infusion device 10 to a proximal end 21 of the catheter 20 so that its chambers are in fluid communication with inflow 22 and outflow 24 lumens of the catheter 20 and a balloon 25. In some embodiments, an inflation chamber 102 and an inflow chamber 103 are then filled with the fluid.

In some embodiments, positioning 401 comprises inserting a distal end 26 of the catheter 20 into a patient. In some embodiments, positioning 401 further comprises navigating the distal end 26 to a desired therapeutic or target location in the patient.

Figure 21C:
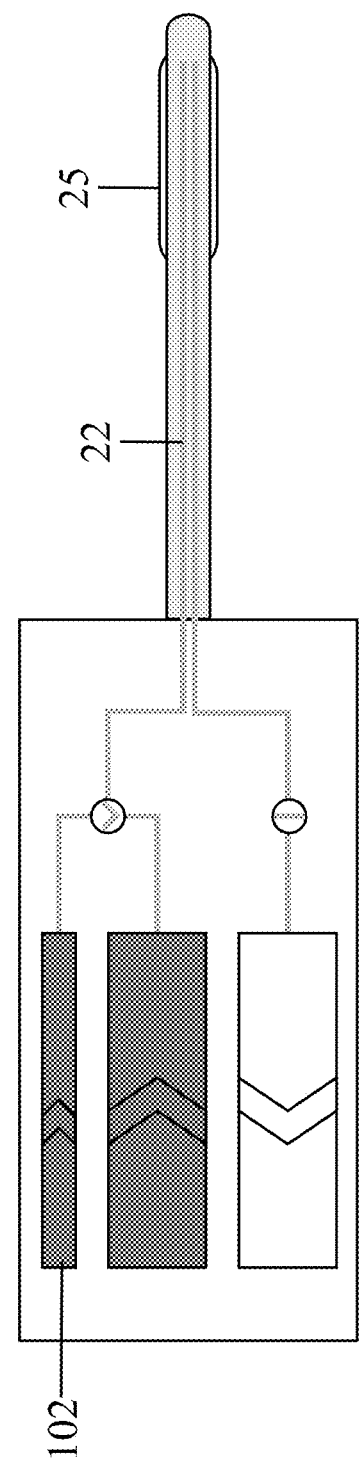
Figure 21D:
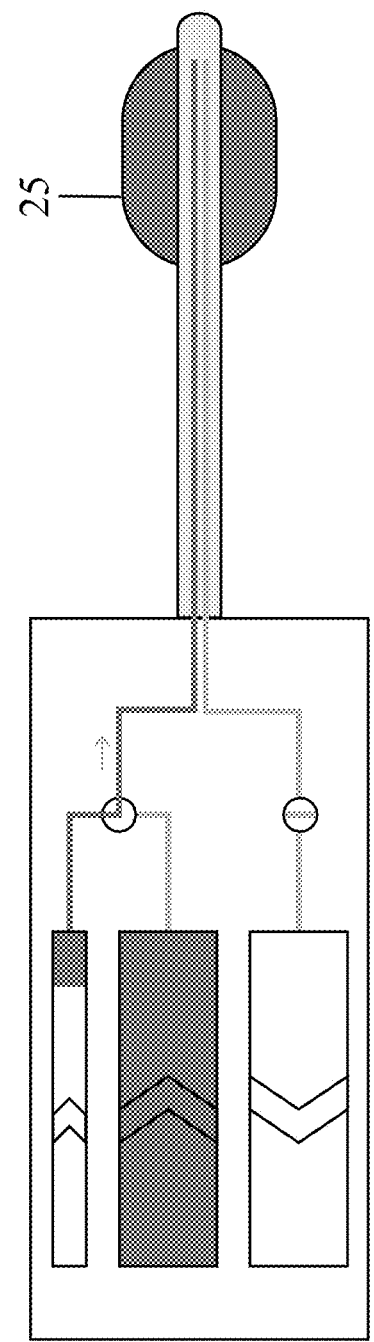

As seen in FIGS. 21C and 21D, in some embodiments, inflating 403 the balloon 25 comprises activating an inflation chamber mechanism 102, which may drive fluid into the inflow lumen 22 and inflate the balloon 25 (see FIG. 21D) to a desired volume and pressure. In some embodiments, the method further comprises monitoring inflation of the balloon 25, and monitoring the location and orientation of the balloon 25 relative to the target location.

Figure 21E:
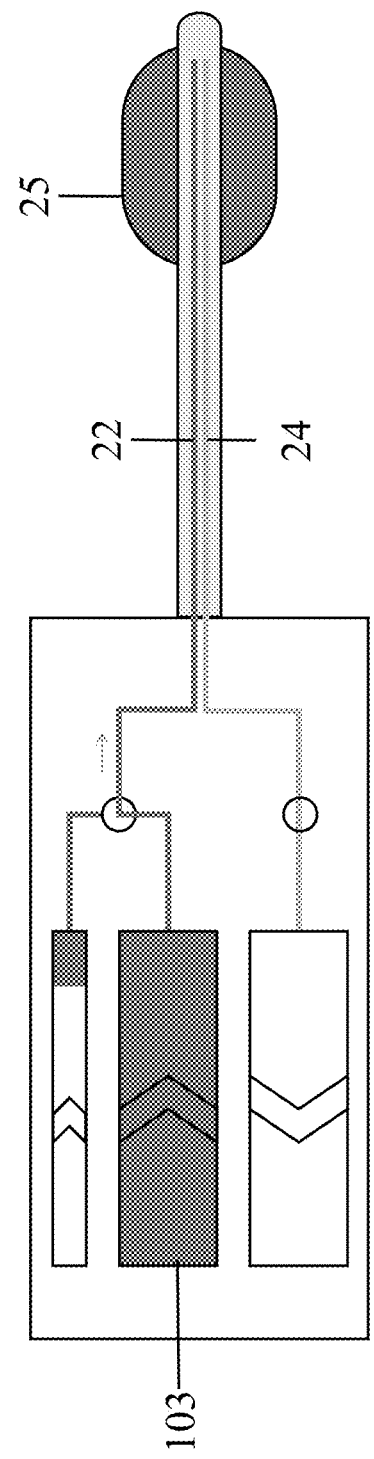
Figure 21F:
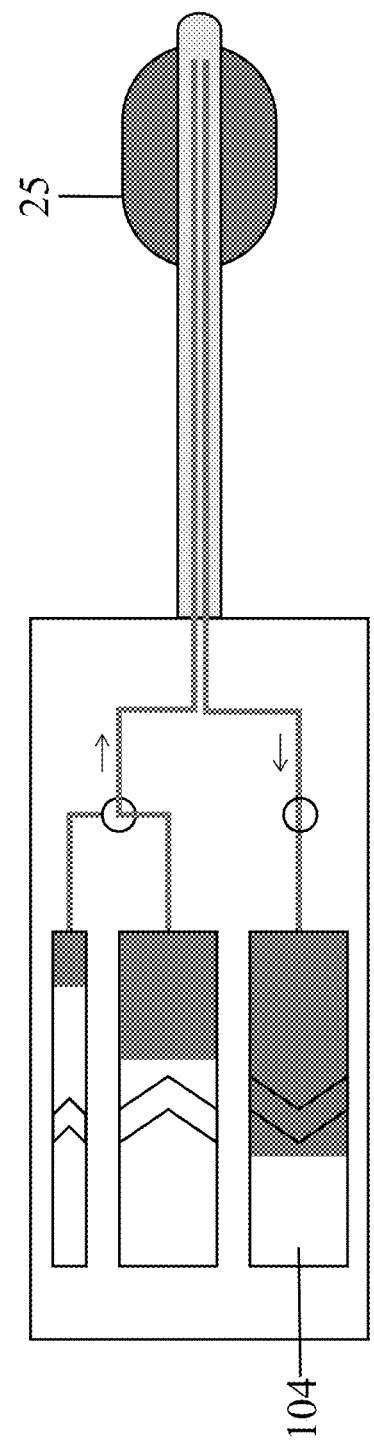

In some embodiments, as seen in FIG. 21E, initiation of infusion 403 may comprise activating the inflow chamber mechanism 103 which drives fluid into and draws fluid out of the balloon 25 through the inflow 22 and outflow 24 lumens at the substantially the same rate. As seen in FIG. 21F, the infusion continues 404 by continuously refreshing the fluid within the balloon 25 to achieve a desired therapeutic effect while maintaining balloon 25 volume and pressure.

Figure 21G:
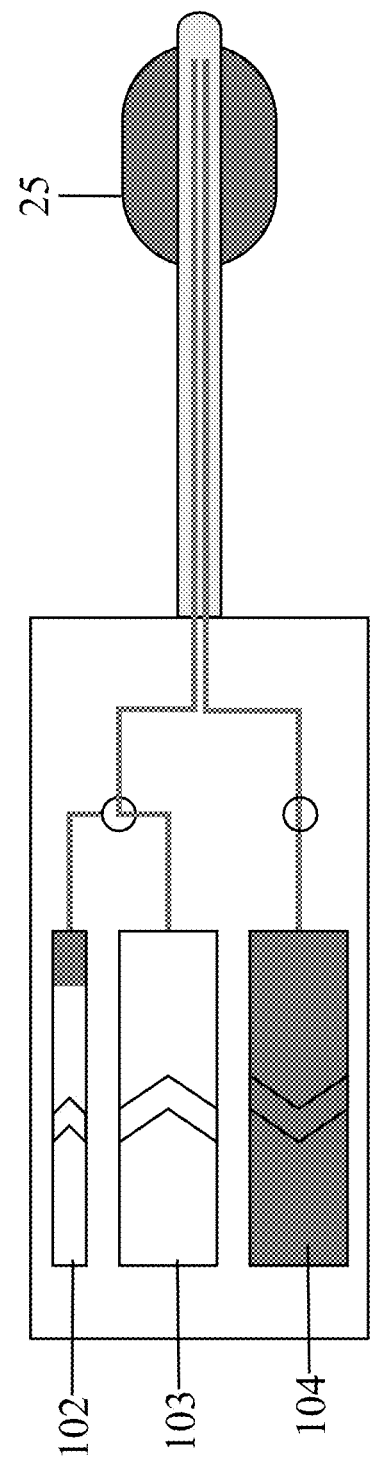
Figure 21H:
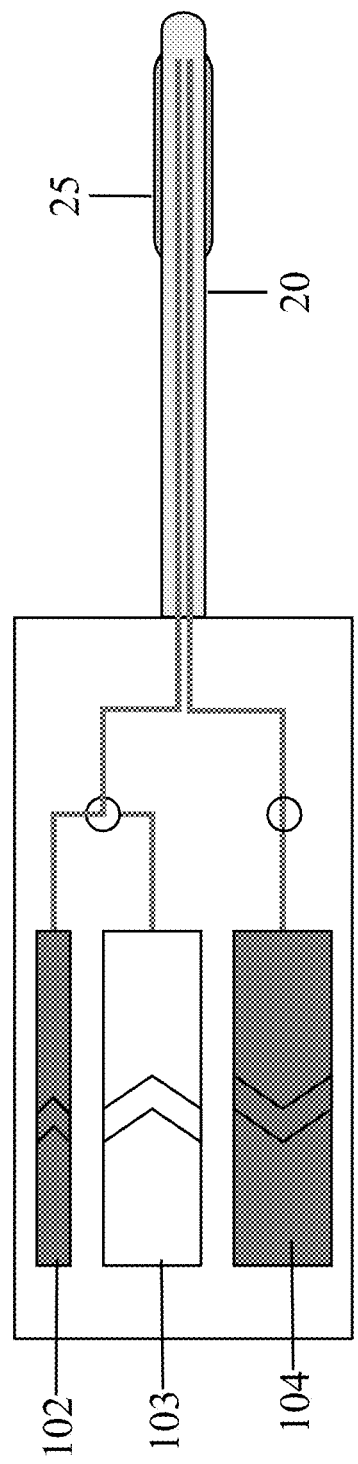

As seen in FIGS. 21G and 21H, terminating the infusion 405 may comprise deactivating the inflow chamber mechanism 103. The balloon 25 may be deflated by reversing the inflation chamber mechanism 103 to withdraw fluid from the balloon 25 back into the inflation chamber 102. The catheter 20 can then be withdrawn from the patient or navigated to a new therapeutic location.

In some embodiments, as depicted in FIG. 22, a method of inflating a balloon catheter comprises: connecting a balloon catheter to an infusion device and an inflation device 2000, filling an inflation chamber and an inflow chamber of the infusion device with a liquid 2010, inserting the balloon catheter into a patient and navigating the balloon to a target tissue (or in the vicinity) 2020, activating the inflation chamber to fill compartments in the catheter with the liquid until a target pressure and volume are reached 2030, activating an infusion mechanism 2040 of the inflow chamber to drive the liquid from the inflow chamber through an inflation lumen into the balloon while concomitantly drawing the liquid from the balloon through an outflow lumen into an outflow chamber of the infusion device, continuing the infusion 2050 until a desire effect is achieved, and terminating the infusion 2060 by deactivating the infusion mechanism. In some embodiments, the inflation device is filled with a gas or connected to a gas line if necessary. In some embodiments, the balloon may be first inflated with the gas by activating a gas inflation device until the target volume or pressure is reached.

Figure 21I:
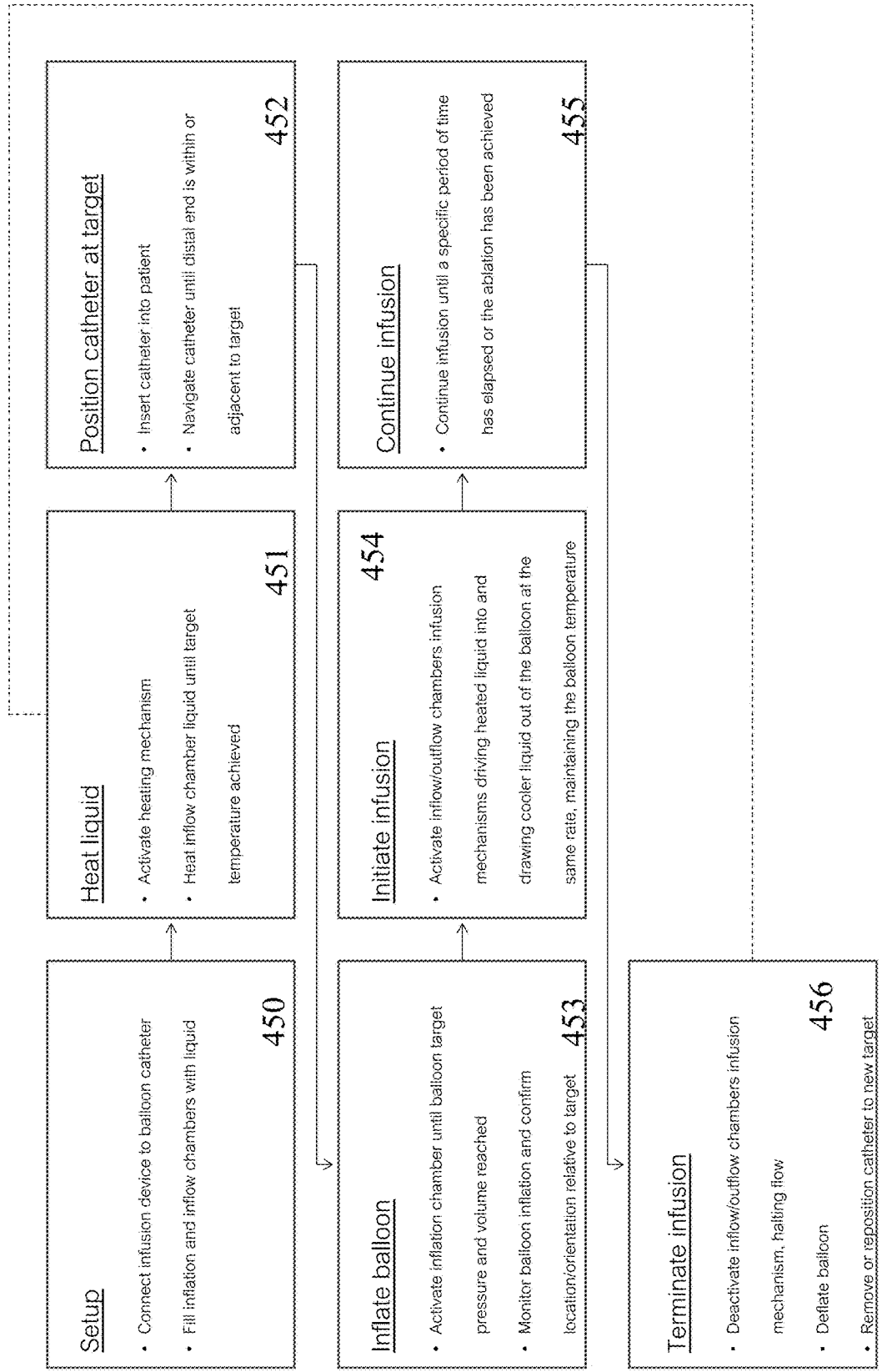

Another embodiment of a method of operating a system 1 to perform a thermal ablation, as depicted in FIG. 21I, comprises: setting up the system 450, heating a liquid 451, positioning a catheter 452, inflating a balloon 453, initiating an infusion 454, continuing the infusion 455, and terminating the infusion 456.

Figure 21J:
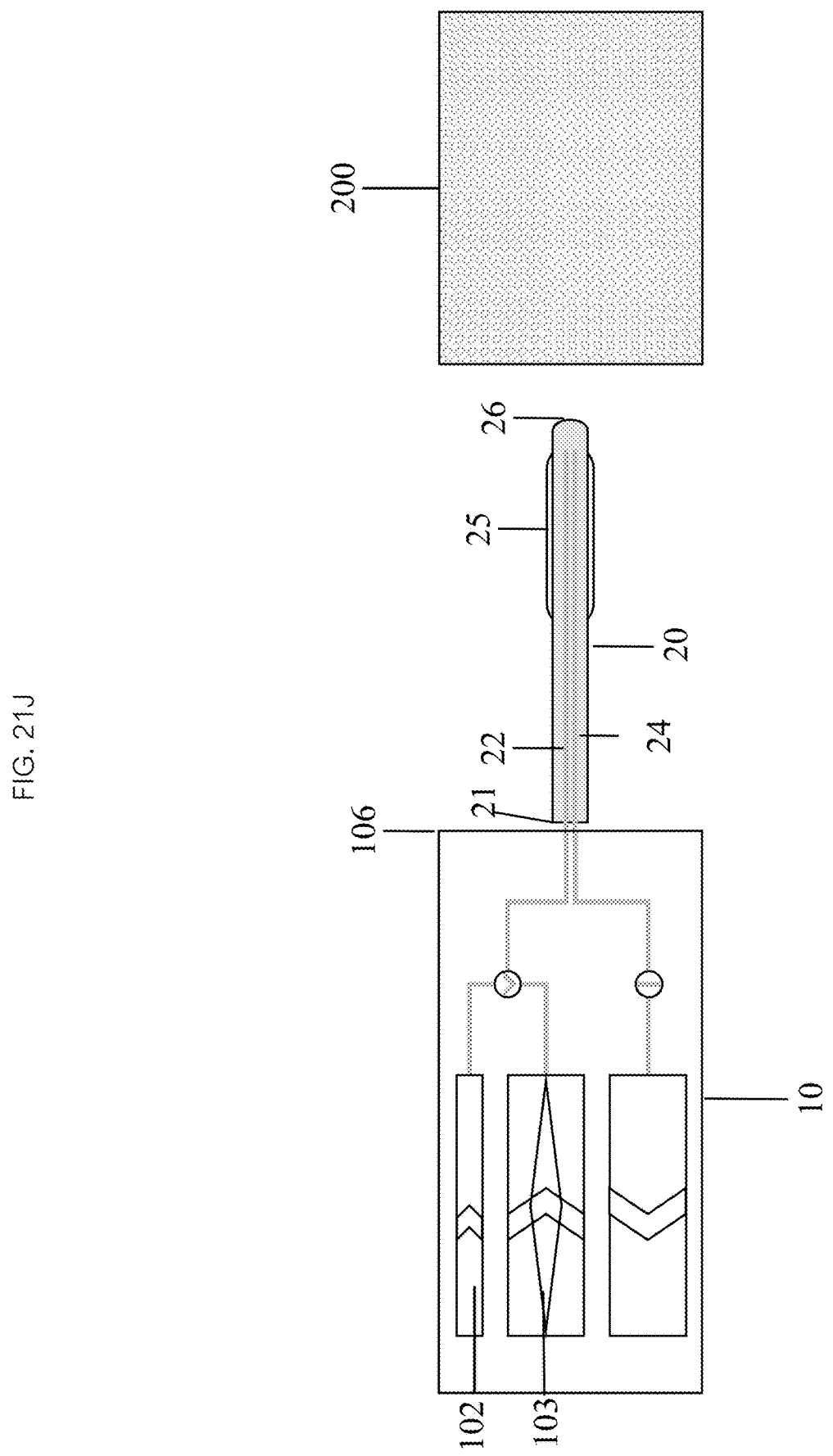
Figure 21K:
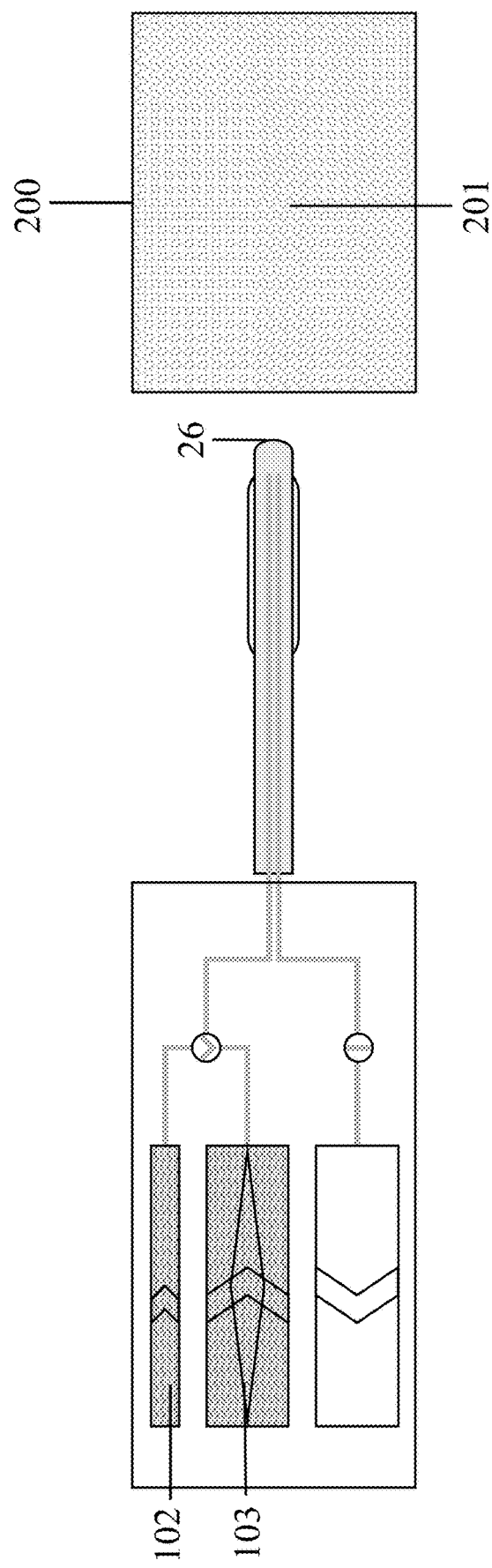
Figure 21L:
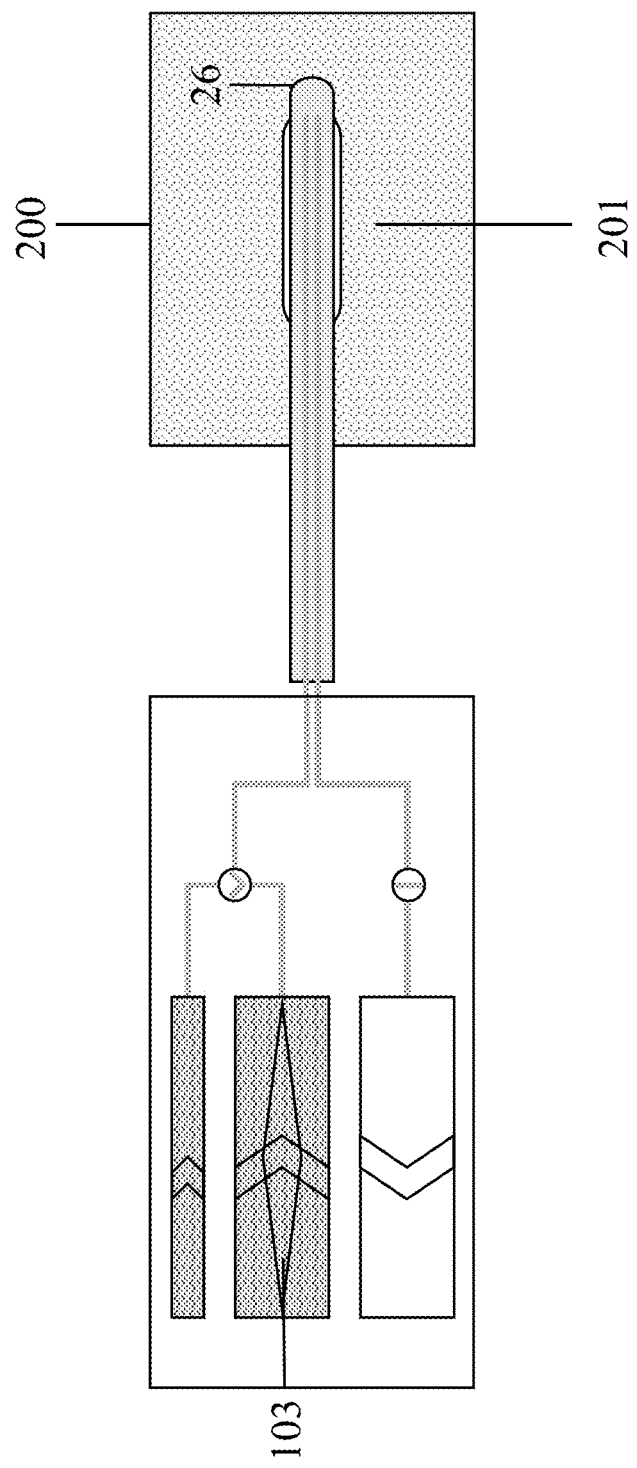
Figure 21M:
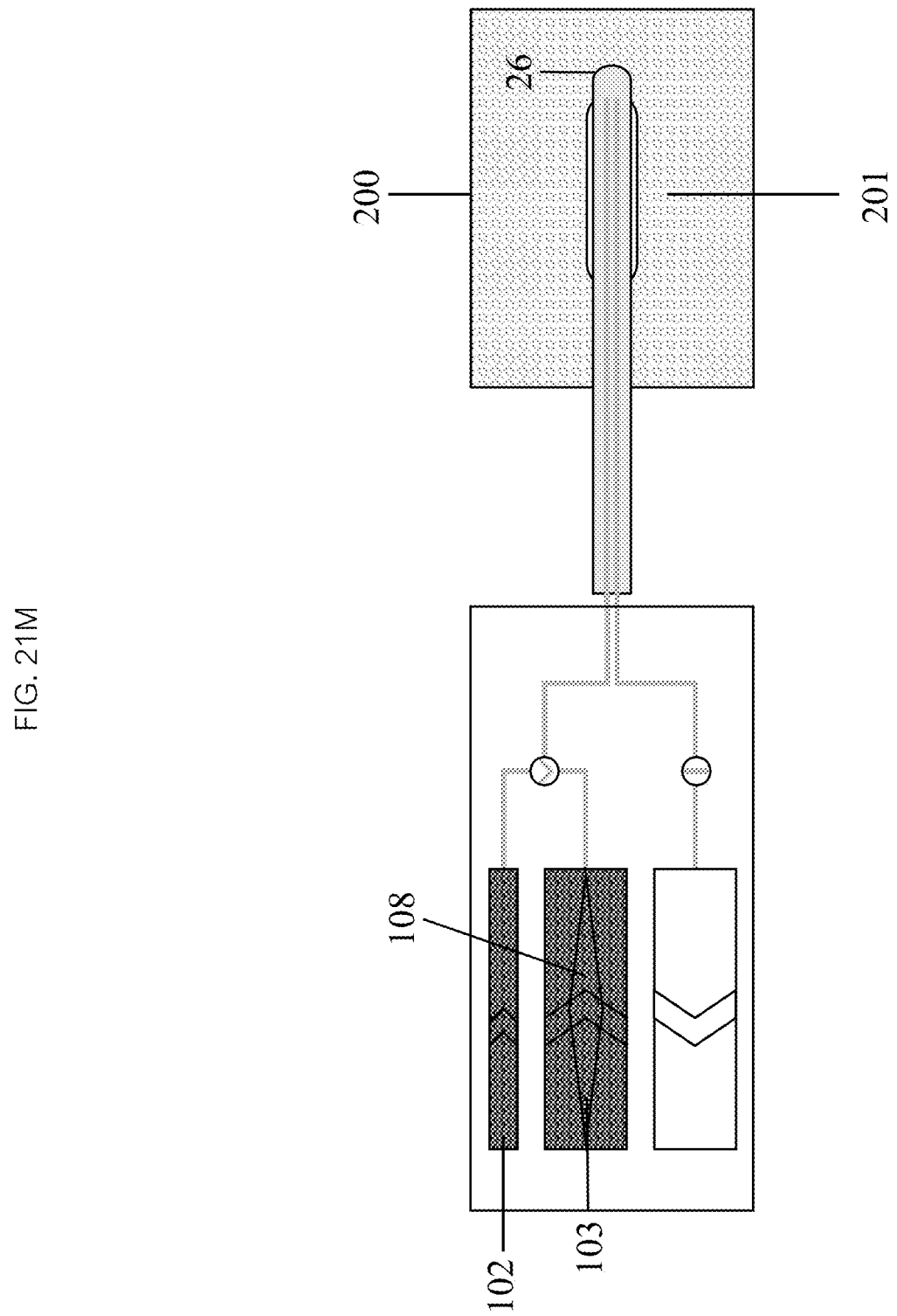
Figure 21N:
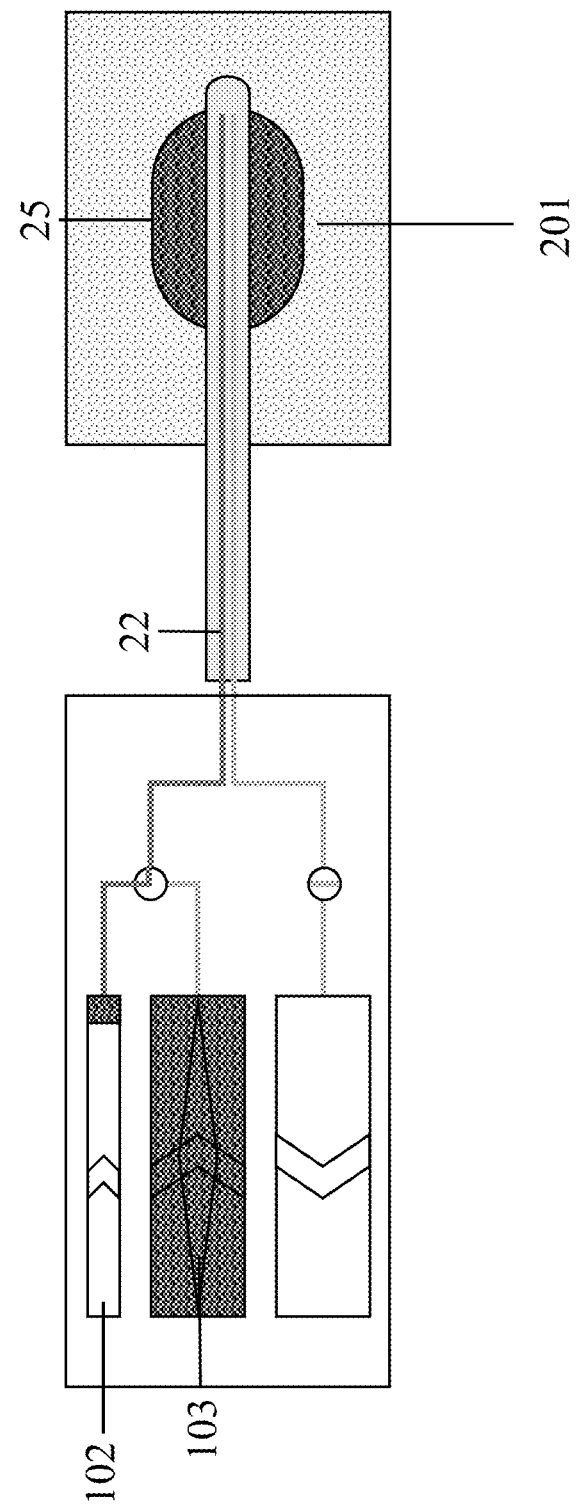
Figure 21P:
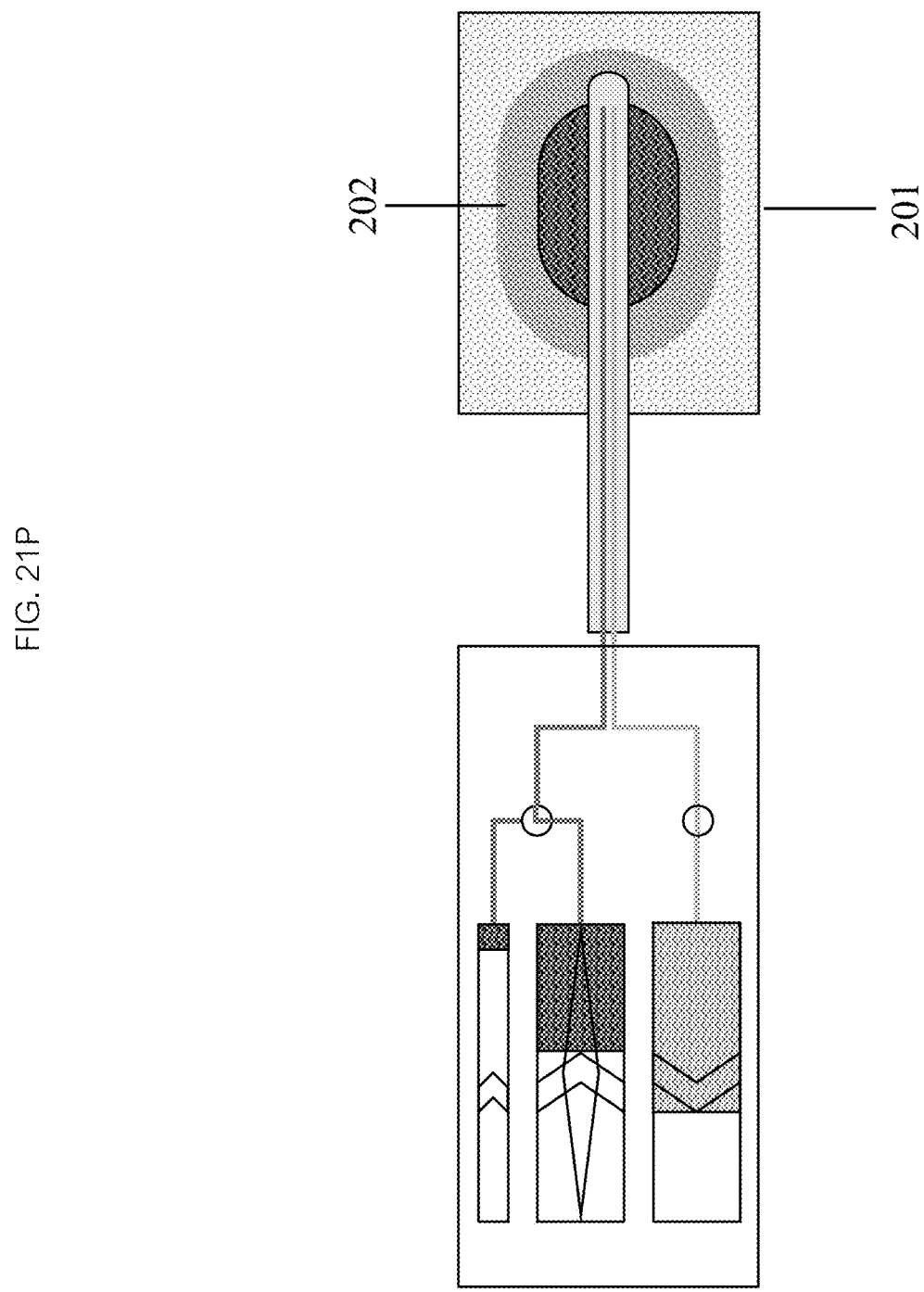
Figure 21Q:
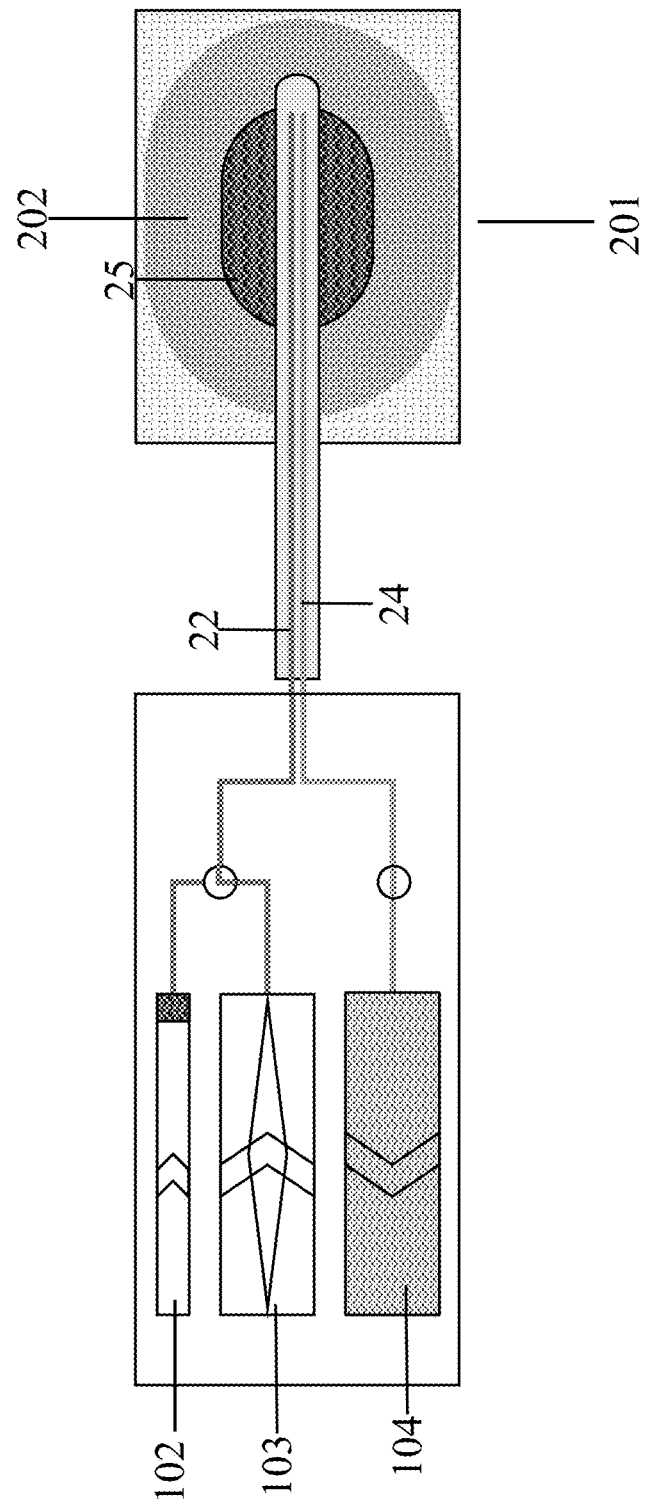
Figure 21R:
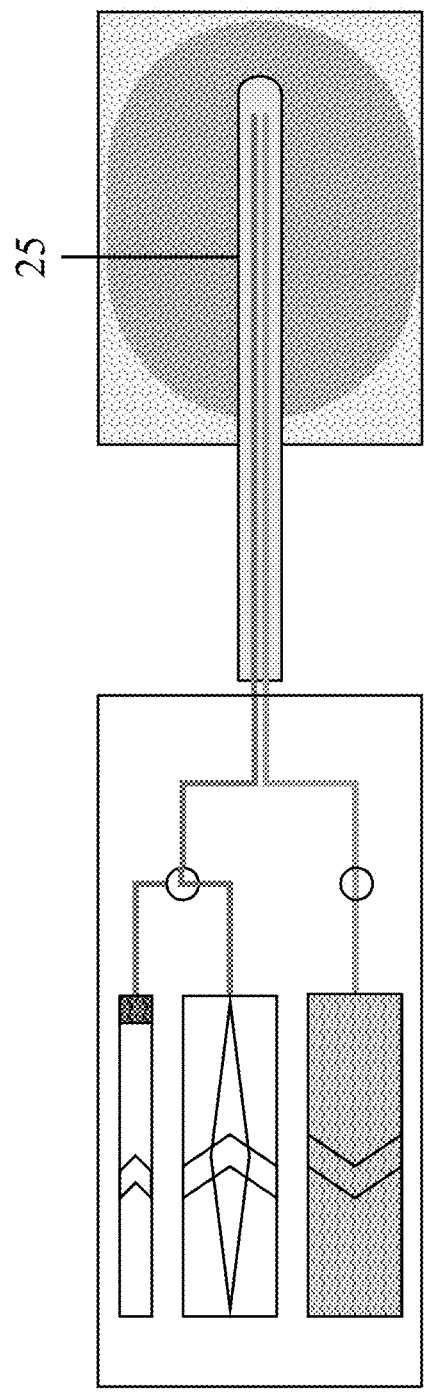

In some embodiments, as seen in FIG. 21J, setting up 450 comprises connecting the distal end 106 of the infusion device 10 to the proximal end 21 of the catheter 20 so that its chambers are in fluid communication with the inflow 22 and outflow 24 lumens of the catheter 20 and the balloon 25. The inflation 102 and inflow chambers 103 are then filled with liquid.

Referring now to FIGS. 21K through 21S, heating the liquid 451 may comprise activating a heating mechanism 108. A liquid in the inflow chamber 103, and optionally in the inflation chamber 102, may then be heated to a target temperature. Positioning 452 may, in some embodiments, comprise positioning the distal end 26 of the catheter 20 into a patient 200 and navigating to a target 201. Inflating the balloon 453 may comprise activating the inflation chamber mechanism 103, thereby driving liquid into the inflow lumen 22 and inflating the balloon 25 to the desired volume and pressure. In some embodiments, the balloon 25 location and orientation relative to the target 201 may be monitored.

In some embodiments, initiating an infusion comprises activating the inflow 103 and outflow chamber 104 infusion mechanisms which drives heated liquid into and draws cooler liquid out of the balloon 25 through the inflow 22 and outflow 24 lumens at substantially the same rate, maintaining the balloon 25 temperature above the target temperature to ablate the target tissue 201. In the continuing step 455, the infusion continues, continuously refreshing the heated liquid within the balloon 25, continuing the ablation process for a designated period of time or until a therapeutic effect is achieved. In some embodiments, the therapeutic effect is ablation, yielding an ablated tissue 202. The infusion can be terminated in the terminating step 456 by deactivating the inflow 103 and outflow chamber 104 infusion mechanisms. The balloon 25 may be deflated by reversing the inflation chamber 102 mechanism to withdraw liquid from it back into the inflation chamber 102. The catheter 20 can then be withdrawn from patient 200 or navigated to a new therapeutic location.

An alternative embodiment of a method of operation allows an operator to enhance efficiency of a system while maintaining efficacy of the system. The infusion device 10 and balloon catheter 20 may be provided separately. Once the inflation 102 and inflow chambers 103 can be filled, the infusion device 10 heats the liquid while the operator positions the balloon catheter 20 at the therapeutic target 201. Once the liquid has reached the target temperature and the catheter 20 is positioned at the target 201, the infusion device 10 and balloon catheter 20 are connected. The remainder of the operation proceeds as above with balloon 25 inflation followed by continuous infusion followed by balloon 25 deflation.

Another embodiment of the method allows multiple infusion cycles by taking advantage of an infusion device 10 which allows the inflow 103 and outflow chambers 104 and lumens 22, 24 to be reversed and heats both the inflow 103 and outflow chambers 104. The initial steps proceed as above. The infusion device 10 is set up, the catheter 20 is positioned, the liquid is heated, the balloon 25 is inflated and the infusion is initiated. As the infusion is proceeding, the liquid in the outflow chamber 104 can be being continuously reheated by the infusion device 10. Once the inflow chamber 103 is empty, the operator adjusts the valves 101 so that the inflow 103 and outflow 104 chambers (and their respective balloon lumens) may be switched and reverses the direction of a manual or automatic drive mechanism 600 (see FIG. 5A). Reversing the direction of flow can be accomplished manually (operator adjusts valves 101 and reverses the drive mechanism 600) or automatically (device detects completion of infusion and electrically adjusts valves 101 and reverses drive mechanism 600). Reversing flow initiates another infusion cycle where the reheated liquid from the original outflow chamber 104 (now the inflow chamber) can be infused back though the balloon 25 into the original inflow chamber 103 (now the outflow chamber). This process can be continued indefinitely over multiple infusion cycles until the ablation has been completed.

In some embodiments the balloon 25 may be designed so that it delivers the thermal ablation energy according to a specified pattern. The balloon 25 can have a simple or a complex shape and structure to address a specific tissue ablation requirement. The target tissue 201 type, location, size, shape and adjacent structures may dictate the ideal balloon 25 shape and structure.

Figure 23:
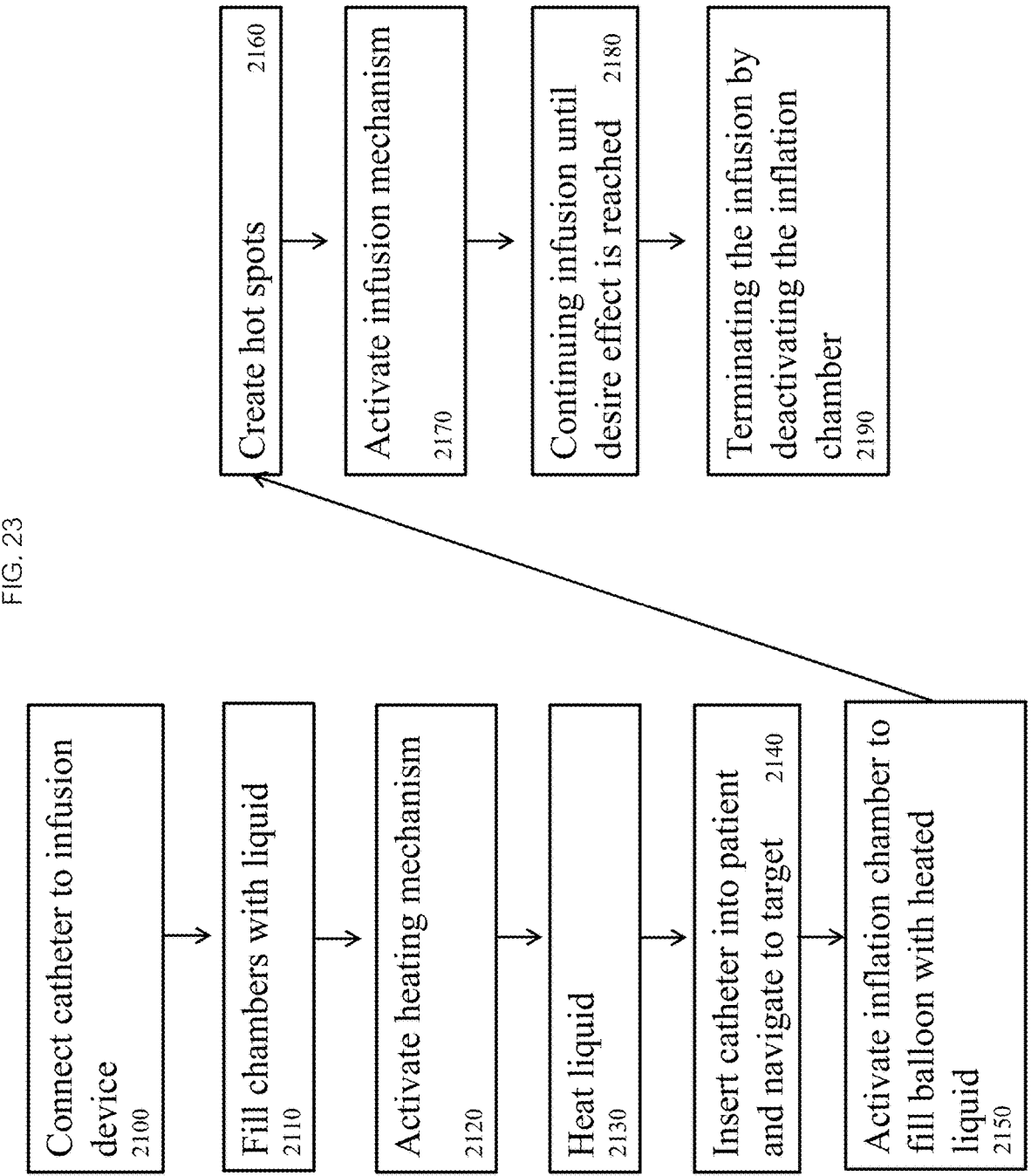
FIG. 23 depicts a flow chart of a thermal ablation method in accordance with the present disclosure.

In some embodiments, as demonstrated in FIG. 23, a method of thermal ablation comprises: connecting a balloon catheter to an infusion device and a gas inflation device 2100, filling an inflation chamber and an inflow chamber of the infusion device with a liquid 2110, activating a heating mechanism of the infusion device 2120 and heating a liquid 2130 in the inflow chamber until a target temperature is achieved, inserting the balloon catheter into a patient and navigating the balloon to a target tissue (or in the vicinity) 2140, activating the inflation chamber to fill compartments in the catheter with a heated liquid until a target pressure and volume are reached 2150, creating an appropriate pattern of hot and cool spots on a surface of the balloon 2160, activating an infusion mechanism 2170 of the inflow chamber to drive the heated liquid from the inflow chamber through an inflation lumen into the heated compartments while concomitantly drawing a cooled liquid from the compartments through an outflow lumen into an outflow chamber of the infusion device, continuing the infusion until an ablation is confirmed by some measure 2180, and terminating the infusion by deactivating the infusion mechanism 2190. In some embodiments, the inflation device is filled with a gas or connected to a gas line if necessary. In some embodiments, the insulating compartments are inflated with the gas first by activating a gas inflation device until the target volume or pressure is reached. In some embodiments, the terminating comprising first deflating the heated compartments and then deflating the insulating compartments. In some embodiments, the balloon catheter may be repositioned to a different target tissue or removed from the patient.

EXAMPLES

Example 1

A thermal fine element analysis (FIGS. 20A1-3 and FIG. 20B1-3) shows that successful ablation of target tissue requires that the temperature in the inner balloon must be maintained above an ablation temperature. This in turn requires that the heated liquid is continuously recycled through the balloon while maintaining its pressure and volume. A single inflation of a balloon with heated liquid, as seen in FIG. 20A3, will not accomplish the desired effect even if the liquid is heated to a very high temperature. The heat sink effect of the tissue will quickly cool the liquid below the ablation temperature before the balloon heats the tissue, which is shown in FIG. 20A where over time (as seen between FIGS. 20A1 and 20A3) the ablation goes away as the inner balloon cools. Ablating while maintaining the temperature of the liquid in the inner balloon above the ablation temperature quickly heats the tissue adjacent to the "hot spot" leading to a successful ablation, as seen in FIG. 20B3. The continuous flow balloon catheter feature of the device of the current invention allows the liquid in the heated liquid compartments to constantly be replenished with heated liquid, maintaining the liquid temperature while keeping the balloon volume and pressure constant.

Example 2

Figure 20C:
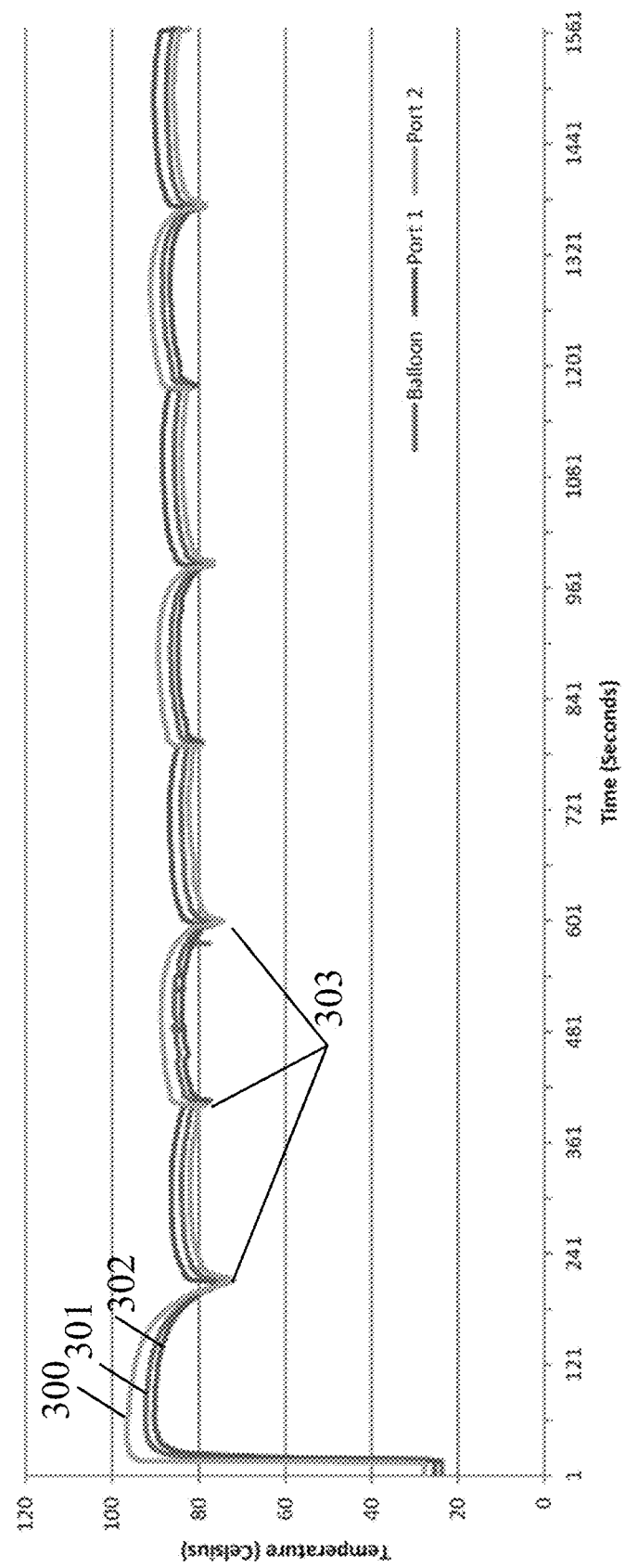

The operation of the continuous flow balloon catheter system over multiple cycles is demonstrated in FIG. 20C. The temperature of the fluid in the balloon 301 and each port 300, 302 of the infusion device is tracked. The ports function as both inflow and outflow ports during alternating cycles 303. The balloon temperature 301 remains very stable through the infusion period. The gradient between the inflow and outflow ports 300, 302 is relatively constant at ~5 C. Finally, switching the direction of the flow between cycles 303 happens rapidly enough that the balloon temperature remains within the target range.

What is claimed is:
1. A system for balloon inflation, the system comprising:
a catheter having an inflow lumen and an outflow lumen;
a balloon positioned at a distal end of the catheter, the balloon being in fluid communication with the inflow and the outflow lumen; and
an infusion device including:

a chamber having a first port in fluid communication with the inflow lumen and a second port in fluid communication with the outflow lumen, and a piston dividing the chamber and configured to move axially within the chamber between the first port and the second port, wherein axial movement of the piston towards the first port drives a fluid out of the chamber through the first port and into the balloon via the inflow lumen and draws the fluid into the chamber through the second port from the balloon via the outflow lumen, thereby circulating the fluid into and out of the balloon while maintaining the balloon at a constant pressure and volume during an entire infusion.

2. The system of claim 1, wherein the infusion device further comprises a heating mechanism to heat the fluid to generate a heated fluid in order to maintain a constant temperature in the balloon via the heated fluid.

3. The system of claim 2, wherein the balloon is divided into multiple compartments, the multiple compartments comprising a mixture of heated compartments and insulating compartments, the heated compartments configured to contain the heated fluid and the insulating compartments configured to contain an insulating fluid.

4. The system of claim 3, wherein a surface of the balloon overlying one or more of the heated compartments allows heat from the heated fluid to transfer to and ablate a target tissue adjacent to the surface of the one or more heated compartments, and a surface overlying one or more of the insulating compartments prevents heat from transferring to a tissue adjacent to the one or more insulating compartments, thereby protecting the tissue adjacent to the one or more insulating compartments from ablation.

5. The system of claim 1, wherein the infusion device further comprises a drive mechanism coupled to the piston for moving the piston axially within the chamber.

6. The system of claim 5, wherein the drive mechanism is manually powered.

7. The system of claim 5, wherein the drive mechanism includes at least one of a plunger, a cable or cord attached to a crankshaft or knob-driven pulley, a fixed length belt or chain attached to a crankshaft or know-driven pulley or gears, or a lead screw.

8. A system for balloon inflation, the system comprising:
a catheter having an inflow lumen and an outflow lumen;
a balloon positioned at a distal end of the catheter, the balloon being in fluid communication with the inflow and the outflow lumen;

a chamber having a first port in fluid communication with the inflow lumen and a second port in fluid communication with the outflow lumen; and a piston dividing the chamber and configured to move axially within the chamber between the first port and the second port, wherein axial movement of the piston towards the first port drives a fluid out of the chamber through the first port and into the balloon via the inflow lumen and draws the fluid into the chamber through the second port from the balloon via the outflow lumen, thereby simultaneously circulating the fluid into and out of the balloon at matching flow rates while maintaining the balloon at a constant pressure and volume during an entire infusion.

9. The system of claim 8, further comprising a heating mechanism internal or external to the chamber to heat the fluid to generate a heated fluid in order to maintain a constant temperature in the balloon via the heated fluid.

10. The system of claim 9, wherein the balloon is divided into multiple compartments, the multiple compartments comprising a mixture of heated compartments and insulating compartments, the heated compartments configured to contain the heated fluid and the insulating compartments configured to contain an insulating fluid.

11. The system of claim 10, wherein a surface of the balloon overlying one or more of the heated compartments allows heat from the heated fluid to transfer to and ablate a target tissue adjacent to the surface of the one or more heated compartments, and a surface overlying one or more of the insulating compartments prevents heat from transferring to a tissue adjacent to the one or more insulating compartments, thereby protecting the tissue adjacent to the one or more insulating compartments from ablation.

12. The system of claim 8, further comprising a drive mechanism coupled to the piston for moving the piston axially within the chamber.

13. The system of claim 12, wherein the drive mechanism is manually powered.

14. The system of claim 12, wherein the drive mechanism includes at least one of a plunger, a cable or cord attached to a crankshaft or knob-driven pulley, a fixed length belt or chain attached to a crankshaft or know-driven pulley or gears, or a lead screw.

* * * * *